(12) United States Patent
Michels et al.

(10) Patent No.: US 8,551,989 B2
(45) Date of Patent: Oct. 8, 2013

(54) SUBSTITUTED 4-(INDAZOLYL)-1,4-DIHYDROPYRIDINES AND METHODS OF USE THEREOF

(75) Inventors: Martin Michels, Köln (DE); Markus Follmann, Wülfrath (DE); Alexandros Vakalopoulos, Hilden (DE); Katja Zimmermann, Düsseldorf (DE); Nicole Teusch, Wülfrath (DE); Karen Engel, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 101 days.

(21) Appl. No.: 12/996,465

(22) PCT Filed: May 29, 2009

(86) PCT No.: PCT/EP2009/003838
§ 371 (c)(1),
(2), (4) Date: May 16, 2011

(87) PCT Pub. No.: WO2009/149837
PCT Pub. Date: Dec. 17, 2009

(65) Prior Publication Data
US 2011/0207731 A1     Aug. 25, 2011

(30) Foreign Application Priority Data
Jun. 9, 2008    (EP) .................................... 08010422

(51) Int. Cl.
*C07D 401/10*    (2006.01)
*A61K 31/4439*   (2006.01)

(52) U.S. Cl.
USPC ........ 514/234.5; 514/318; 514/338; 544/124; 546/194; 546/275.7

(58) Field of Classification Search
None
See application file for complete search history.

(56) References Cited

U.S. PATENT DOCUMENTS

| | | | |
|---|---|---|---|
| 5,200,420 | A | 4/1993 | Goldmann et al. |
| 5,364,855 | A | 11/1994 | Straub et al. |
| 5,508,406 | A | 4/1996 | Stoltefuss et al. |
| 5,545,646 | A | 8/1996 | Straub et al. |
| 2005/0208582 | A1 | 9/2005 | Ohi et al. |
| 2005/0227968 | A1 | 10/2005 | Lustenberger et al. |
| 2007/0238726 | A1 | 10/2007 | Blake et al. |

FOREIGN PATENT DOCUMENTS

| | | |
|---|---|---|
| WO | 2004033444 A1 | 4/2004 |
| WO | 2005016885 A2 | 2/2005 |
| WO | 2005056550 A1 | 6/2005 |
| WO | 2006066011 A2 | 6/2006 |
| WO | 2007051062 A2 | 5/2007 |
| WO | 2007124288 A1 | 11/2007 |
| WO | 2008071451 A1 | 6/2008 |

OTHER PUBLICATIONS

Cooper, C.S. et al., Nature, 1984, 311: 29-33.
Rodrigues, G.A., et al., Mol. Cell. Biol., 1991, 11: 2962-70.
Ponzetto, C., et al., Cell, 1994, 77: 261-71.
Tomita, N., et al. Circulation, 2003, 107: 1411-1417.
Ding, S., et al., Blood, 2003, 101: 4816-4822.
Zeng, Q., et al., J. Biol. Chem., 2002, 277: 25203-25208.
Horiguchi, N., et al. Oncogene 2002, 21: 1791-1799.
Bardelli, A., et al., Embo. J., 1996, 15: 6205-6212.
Longati, P., et al., Cell Death Differ., 1996, 3: 23-28.
Rosen, E. M., Symp. Soc. Exp. Biol., 1993, 47: 227-234.
Schmidt, L., et al., Nat. Genet., 1997, 16:68-73.
Zbar, B, et al., Adv. Cancer Res., 1998, 75: 163-201.
Kong-Beltran, M., et al., Caner Res., 2006, 66: 283-9.
Taher, T.E., et al., J. Immunol., 2002, 169: 3793-800.
Peschard, P., et al., 2001, Mol. Cell, 8:995-1004.
Engelmann, J.A., et al., Science, 2007, 316: 1039-1043.
Christensen, J.G., et al., Cancer Lett., 2005, 225: 1-26.
Birchmeier, C., et al., Nat. Rev. Mol. Cell Biol., 2003, 4: 915-25.
Cui, J.J., Expert Opin. Ther. Patents, 2007, 17: 1035-45.
S.M. Berge et al., "Pharmaceutical Salts," J. Pharm. Sci. 1977, 66, 1-19.
D.M. Stout, A.I. Meyers, Chem. Rev. 1982, 82, 223-243.
H. Meier et al., Liebigs Ann. Chem. 1977, 1888-1894.
H. Meier et al., Liebigs Ann. Chem. 1977, 1895-1908.
H. Meier et al., Liebigs Ann. Chem. 1976, 1762-1766.
F. Bossert, et al., Angew. Chem. 1981, 93, 755-763.
G. Luo et al., J. Org. Chem. 2006, 71, 5392-5395.
J. Hassan et al., Chem. Rev. 2002, 102, 1359-1469.
L. Naldini et al., Oncogene 6: 501-4 (1991).

*Primary Examiner* — Zinna Northington Davis

(57) ABSTRACT

This invention relates to novel 4-(indazolyl)-1,4-dihydropyridine of the following formula (I) derivatives having protein tyrosine kinase inhibitory activity, to a process for the manufacture thereof and to the use thereof for the treatment of c-Met-mediated diseases or c-Met-mediated conditions, particularly cancer and other proliferative disorders.

20 Claims, No Drawings

SUBSTITUTED 4-(INDAZOLYL)-1,4-DIHYDROPYRIDINES AND METHODS OF USE THEREOF

This application is a 371 of PCT/EP09/03838 filed May 29, 2009.

This invention relates to novel 4-(indazolyl)-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

Cancer is one of the most common widespread diseases. Over 4.4 million people worldwide were diagnosed with breast, colon, ovarian, lung or prostate cancer in 2002, and over 2.5 million people died of these devastating diseases (Globocan 2002 Report, http://www-dep.iarc.fr/globocan/down-loads.htm). In the United States alone, over 1.25 million new cases and over 500 000 deaths from cancer were predicted in 2005. The majority of these new cases were expected to be cancers of the colon (~100 000), lung (~170 000), breast (~210 000) and prostate (~230 000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

There are many ways how cancers can arise, which is one of the reasons why their therapy is difficult. One way is the transformation of cells by oncoproteins, which arise from normal cellular proteins by genetic mutations, which results in a non-physiological activation of these proteins. One family of proteins from which a number of oncoproteins derive are tyrosine kinases (e.g. src kinase) and in particular receptor tyrosine kinases (RTKs). In the past two decades, numerous avenues of research have demonstrated the importance of receptor tyrosine kinase (RTK)-mediated signalling in the regulation of mammalian cell growth. Recently, results have been achieved in the clinic with selective small-molecule inhibitors of tyrosine kinases as anti-tumourigenic agents.

The c-Met receptor also is a receptor tyrosine kinase. Its oncogenic potential was identified in the early 1980s, when a mutated Met was isolated from a chemically induced human osteosarcoma cell line which contained the kinase domain of the Met gene fused to a dimerization domain at its N-terminus [C. S. Cooper et al., *Nature* 311: 29-33 (1984)].

The cellular Met protein is a heterodimeric transmembrane protein synthesized as a single chain 190 kd precursor [G. A. Rodrigues et al., *Mol. Cell. Biol.* 11: 2962-70 (1991)]. The precursor is cleaved intracellularly after amino acid residue 307 to form the 50 kd α-chain and the 145 kd β-chain, which are connected by disulfide bridges. The α-chain is entirely extracellular, whereas the β-chain spans the plasma membrane. The β-chain is composed of an N-terminal sema domain, which together with the α-chain mediates ligand binding. The remainder of the ectodomain of the β-chain is composed of a cysteine-rich domain and four immunoglobulin domains and is followed by the transmembrane region and the intracellular domain. The intracellular domain contains a juxtamembrane domain, the kinase domain and a C-terminal domain, which mediates the down-stream signalling. Upon ligand binding, a dimerization of the receptor is induced, and the kinase domain is activated by a cascade of tyrosine auto-phosphorylation steps in the juxtamembrane region (Y1003), the activation loop of the kinase (Y1234 and Y1235) and the carboxy-terminal domain (Y1349 and Y1356). Phosphorylated Y1349 and Y1356 comprise the multi-substrate docking site for binding adapter proteins necessary for downstream c-Met signalling [C. Ponzetto et al., *Cell* 77: 261-71 (1994)]. One of the most crucial substrates for c-Met signalling is the scaffolding adaptor protein Gab1, which binds to either Y1349 or Y1356 via an unusual phospho-tyrosine binding site (termed mbs: met binding site) which causes a unique prolonged intracellular signal. Another important substrate is the adaptor protein Grb2. Depending on the cellular context, these adaptors mediate the activation of various intracellular signal pathways like the ones signalling via ERK/MAPK, PI3K/Akt, Ras, JNK, STAT, NFκβ and β-catenin.

c-Met is uniquely activated by hepatocyte growth factor (HGF), also known as scatter factor, and its splice variants, which is its only known biologically active ligand [L. Naldini et al., *Oncogene* 6: 501-4 (1991)]. HGF has a distinct structure which reveals similarities to proteinases of the plasminogen family. It is composed of an amino-terminal domain followed by four kringle domains and a serine protease homology domain, which is not enzymatically active. Similar to c-Met, HGF is synthesized as an inactive single chain precursor (pro-HGF), which is extracellularly cleaved by serine proteases (e.g. plasminogen activators and coagulation factors) and converted into a disulfide-linked active α- and β-chain heterodimer. HGF binds heparan sulfate proteoglycans with high affinity, which keeps it mainly associated with the extracellular matrix and limits its diffusion. Crystal structure analyses indicate that HGF forms a dimer, which upon binding to c-Met induces dimerization of the receptor.

HGF is expressed by mesenchymal cells, and its binding to c-Met, which is widely expressed in particular in epithelial cells, results in pleiotropic effects in a variety of tissues including epithelial, endothelial, neuronal and hematopoetic cells. The effects generally include one or all of the following phenomena: i) stimulation of mitogenesis; HGF was identified by its mitogenic activity on hepatocytes; ii) stimulation of invasion and migration; in an independent experimental approach, HGF was identified as scatter factor based on its induction of cell motility ("scattering"); and iii) stimulation of morphogenesis (tubulogenesis). HGF induces the formation of branched tubules from canine kidney cells in a collagen matrix. Furthermore, evidence from genetically modified mice and from cell culture experiments indicate that c-Met acts as a survival receptor and protects cells from apoptosis [N. Tomita et al., *Circulation* 107: 1411-1417 (2003); S. Ding et al., *Blood* 101: 4816-4822 (2003); Q. Zeng et al., *J. Biol. Chem.* 277: 25203-25208 (2002); N. Horiguchi et al., *Oncogene* 21: 1791-1799 (2002); A. Bardelli et al., *Embo J.* 15: 6205-6212 (1996); P. Longati et al., *Cell Death Differ.* 3: 23-28 (1996); E. M. Rosen, *Symp. Soc. Exp. Biol.* 47: 227-234 (1993)]. The coordinated execution of these biological processes by HGF results in a specific genetic program which is termed as "invasive growth".

Under normal conditions, c-Met and HGF are essential for embryonic development in mice, in particular for the development of the placenta and the liver and for the directional migration of myoblasts from the somites of the limbs. Genetic disruption of the c-Met or HGF genes results in identical phenotypes which shows their unique interaction. The physiological role of c-Met/HGF in the adult organism is less well understood, but experimental evidence suggests that they are involved in wound healing, tissue regeneration, hemopoiesis and tissue homeostasis.

The identification of the oncoprotein TPR-MET was a first hint that c-Met may play a role in tumourigenesis. Additional substantial evidence is derived from a number of different experimental approaches. Overexpression of c-Met or HGF in human and murine cell lines induces tumouri-genicity and a metastatic phenotype when expressed in nude mice. Transgenic overexpression of c-Met or HGF induces tumourigenesis in mice.

Most intriguingly, missense mutations of c-Met or mutations which activate the receptor have been identified in sporadic and hereditary papillary kidney carcinomas (HPRC) as well as in other cancer types like lung, gastric, liver, head and neck, ovarian and brain cancers. Significantly, specific c-Met mutations in HPRC families segregate with disease, forming a causal link between c-Met activation and human cancer [L. Schmidt et al., *Nat. Genet.* 16: 68-73 (1997); B. Zbar et al., *Adv. Cancer Res.* 75: 163-201 (1998)]. Activation mutations with the strongest transforming activities are located in the activation loop (D1228N/H and Y1230H/D/C) and in the adjacent P+1 loop (M1250T). Additional weaker mutations have been found near the catalytic loop and within the A lobe of the kinase domain. Furthermore, some mutations in the juxtamembrane domain of c-Met have been observed in lung tumours which do not directly activate the kinase, but rather stabilize the protein by rendering it resistant to ubiquitination and subsequent degradation [M. Kong-Beltran et al., *Cancer Res.* 66: 283-9 (2006); T. E. Taher et al., *J. Immunol.* 169: 3793-800 (2002); P. Peschard et al., *Mol. Cell.* 8: 995-1004 (2001)]. Interestingly, somatic mutations of c-Met are associated with increased aggressiveness and extensive metastases in various cancers. While the frequency of germ line and somatic mutations is low (below 5%), other major mechanisms have been observed leading to a deregulation of the c-Met signalling, in the absence of mutations, by paracrine or autocrine mechanisms. Paracrine activation has been observed in tumours which are derived from mesenchymal cells, like osteosarcomas or rhabdomyosarcomas, which physiologically produce HGF, and in glioblastomas and mamma carcinomas which are of ectodermal origin.

However, the most frequent cases are carcinomas where c-Met is overexpressed as observed in carcinomas of the colon, pancreas, stomach, breast, prostate, ovary and liver. Overexpression may arise, for example, by gene amplification as observed in gastric and lung tumour cell lines. Very recently, overexpression of c-Met was detected in lung tumour cell lines which acquired resistance to EGF receptor inhibition [J. A. Engelmann et al., *Science* 316: 1039-1043 (2007)]. Some epithelial tumours that overexpress c-Met also co-express HGF, resulting in an autocrine c-Met/HGF stimulatory loop and thereby circumventing the need for stromal cell-derived HGF.

In general, it has been found that aberrant activation of c-Met in human cancer is typically associated with a poor prognosis, regardless of the specific mechanism [J. G. Christensen et al., *Cancer Lett.* 225: 1-26 (2005)].

In summary, a great number of in vitro and in vivo studies have been performed that validate c-Met as an important cancer target, and a comprehensive list can be viewed at http://www.vai.org/met [C. Birchmeier et al., *Nat. Rev. Mol. Cell. Biol.* 4: 915-25 (2003)]. Several strategies have been followed to attenuate aberrant Met signalling in human tumours including HPF antagonists and small molecule inhibitors, amongst others. A number of small molecule inhibitors are currently in clinical development, such as ARQ-197 (Arqule), XL-880 (Exelixis), and PH-2341066 (Pfizer); they have recently been reviewed [J. J. Cui, *Expert Opin. Ther. Patents* 17: 1035-45 (2007)].

The technical problem to be solved according to the present invention may therefore be seen in providing alternative compounds having an inhibitory activity on the c-Met kinase, thus offering new therapeutic options for the treatment of c-Met-mediated diseases, particularly cancer and other proliferative disorders.

1,4-Dihydropyridine derivatives having a bicyclic heteroaryl substituent in 4-position and the use thereof for the treatment of cardiovascular diseases have been described in EP 0 450 420-A2, EP 0 555 657-A1, EP 0 622 368-A1 and EP 0 630 895-A1. Other 4-heteroaryl-1,4-dihydropyridine derivatives for the treatment of diseases have been disclosed more recently in WO 2004/033444-A1, WO 2005/016885-A2, WO 2006/066011-A2 and WO 2007/051062-A2. In the interim, 1,4-dihydropyridine-type compounds with c-Met kinase inhibitory activity have been described in WO 2008/071451-A1.

In one aspect, the present invention relates to 4-(indazolyl)-1,4-dihydropyridine derivatives of the general formula (I)

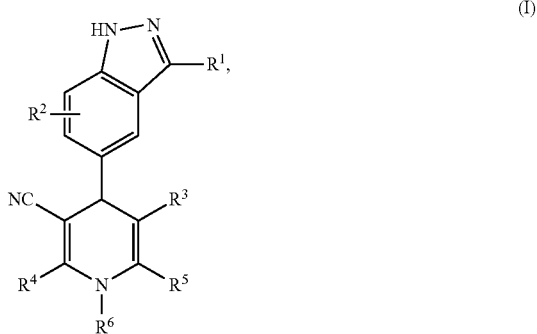

wherein $R^1$ is a group of the formula $-NR^7R^8$, $-NR^9-C(=O)-R^{10}$, $-NR^{11}-SO_2-R^{12}$, $-OR^{13}$, $-S(=O)_n-R^{14}$ or $-SO_2-NR^{15}R^{16}$, wherein n is 0, 1 or 2, $R^7$, $R^8$, $R^{10}$, $R^{12}$, $R^{13}$ and $R^{14}$ are independently selected from the group consisting of $(C_1-C_6)$-alkyl, $(C_3-C_7)$-cycloalkyl, phenyl, 4- to 7-membered heterocycloalkyl and 5- to 10-membered heteroaryl, wherein (i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, $R^9$ is $(C_1-C_6)$-alkyl, $R^{11}$ is hydrogen or $(C_1-C_6)$-alkyl, or $R^{11}$ and $R^{12}$ are joined and, taken together with the nitrogen atom and $SO_2$ group to which they are attached, form a heterocyclic moiety of the formula

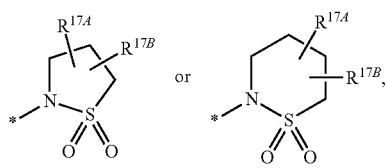

wherein * denotes the point of attachment to the indazole moiety, and $R^{17A}$ and $R^{17B}$ are independently selected from the group consisting of hydrogen, fluoro and $(C_1-C_4)$-alkyl, $R^{15}$ and $R^{16}$ are independently selected from the group consisting of hydrogen, $(C_1-C_6)$-alkyl, $(C_3-C_7)$-cycloalkyl, phenyl, 4- to 7-membered heterocycloalkyl and 5- to 10-membered heteroaryl, wherein (i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^{15}$ and $R^{16}$ are joined and, taken together with the nitrogen atom to which they are attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^2$ is hydrogen, fluoro, chloro or methyl, $R^3$ is cyano or a group of the formula —C(=O)—O$R^{18}$ or —C(=O)—N$R^{19}R^{20}$, wherein $R^{18}$ is $(C_1-C_6)$-alkyl optionally substituted with $(C_3-C_7)$-cycloalkyl, or is $(C_4-C_7)$-cycloalkyl, and $R^{19}$ and $R^{20}$ are independently selected from the group consisting of hydrogen, $(C_1-C_6)$-alkyl and $(C_3-C_7)$-cycloalkyl, wherein said $(C_1-C_6)$-alkyl is optionally substituted with $(C_3-C_7)$-cycloalkyl, $R^4$ is $(C_1-C_4)$-alkyl optionally substituted with up to three fluoro atoms, or is cyclopropyl or amino, $R^5$ is $(C_1-C_6)$-alkyl optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocycloalkyl, wherein (i) said $(C_1-C_4)$-alkoxy substituent is optionally further substituted with a residue selected from the group consisting of hydroxy, $(C_1-C_4)$-alkoxy, amino, mono-$(C_1-C_4)$-alkyl-amino, di-$(C_1-C_4)$-alkylamino and 4- to 7-membered heterocycloalkyl, and (ii) said mono-$(C_1-C_4)$-alkylamino and di-$(C_1-C_4)$-alkylamino substituents are optionally further substituted with one or two residues selected from the group consisting of hydroxy and $(C_1-C_4)$-alkoxy, or $R^5$ is selected from the group consisting of $(C_3-C_7)$-cycloalkyl, phenyl and 5- or 6-membered heteroaryl each of which is optionally substituted with one or two substituents independently selected from the group consisting of fluoro, chloro, difluoromethyl, trifluoromethyl, $(C_1-C_4)$-alkyl, hydroxy, difluoromethoxy, trifluoromethoxy, $(C_1-C_4)$-alkoxy, amino, mono-$(C_1-C_4)$-alkylamino and di-$(C_1-C_4)$-alkylamino, and $R^6$ is hydrogen, $(C_1-C_4)$-alkyl or cyclopropyl.

The compounds according to this invention can also be present in the form of their salts, hydrates and/or solvates.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19).

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, and ethylenediamine.

Hydrates of the compounds of the invention or their salts are stoichiometric compositions of the compounds with water, such as, for example, hemi-, mono-, or dihydrates.

Solvates of the compounds of the invention or their salts are stoichiometric compositions of the compounds with solvents.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

Alkyl in general represents a straight-chain or branched saturated hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, neopentyl, hexyl, isohexyl. The same applies to radicals such as alkoxy, alkylamino, and the like.

Alkoxy illustratively and preferably represents methoxy, ethoxy, n-propoxy, isopropoxy, n-butoxy and tert.-butoxy. The same applies to radicals such as alkoxycarbonyl.

Alkoxycarbonyl illustratively and preferably represents methoxycarbonyl, ethoxycarbonyl, n-propoxycarbonyl, isopropoxycarbonyl, n-butoxycarbonyl and tert.-butoxycarbonyl.

Monoalkylamino in general represents an amino radical having one alkyl residue attached to the nitrogen atom. Non-limiting examples include methylamino, ethylamino, n-propylamino, isopropylamino, n-butylamino, tert.-butylamino. The same applies to radicals such as monoalkyl-aminocarbonyl.

Dialkylamino in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-isopropyl-N-n-propylamino, N-tert.-butyl-N-methylamino. The same applies to radicals such as dialkylaminocarbonyl.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert.-butylaminocarbonyl.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert-butyl-N-methyl-aminocarbonyl.

Cycloalkyl in general represents a mono- or bicyclic saturated hydrocarbon radical having 3 to 7, preferably 3 to 6 carbon atoms. Preference is given to monocyclic cycloalkyl radicals. Non-limiting examples include cyclopropyl, cyclobutyl, cyclopentyl, cyclohexyl, cycloheptyl, bicyclo-[2.2.1]heptyl.

Heterocycloalkyl in general represents a mono- or bicyclic, saturated heterocyclic radical having a total number of 4 to 7, preferably 4 to 6 ring atoms, including 3 to 6, preferably 3 to 5 carbon atoms and up to 2 heteroatoms and/or hetero-groups independently selected from the group consisting of N, O, S, SO and $SO_2$, which ring system can be bonded via a ring carbon atom or, if possible, via a ring nitrogen atom. Non-limiting examples include azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomorpholinyl, perhydroazepinyl, perhydro-1,4-diazepinyl, perhydro-1,4-oxazepinyl, 7-azabicyclo[2.2.1]heptyl, 3-azabicyclo-[3.2.0]heptyl, 7-azabicyclo[4.1.0]heptyl, 2,5-diazabicyclo[2.2.1]heptyl, 2-oxa-5-azabicyclo[2.2.1]-heptyl. Particular preference is given to 5- or 6-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, and thiomorpholinyl.

Heteroaryl in general represents a mono- or bicyclic, aromatic heterocyclic radical having a total number of 5 to 10 ring atoms, including 2 to 9 carbon atoms and up to 3 heteroatoms independently selected from the group consisting of N, O and S, which ring system can be bonded via a ring carbon atom or, if possible, via a ring nitrogen atom. Non-limiting examples include furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, benzothiadiazolyl, indolyl, isoindolyl, indazolyl, quinolinyl, isoquinolinyl, naphthyridinyl, quinazolinyl, quinoxalinyl, phthalazinyl, imidazopyridinyl, pyrazolopyridinyl, pyrrolopyrimidinyl. Preference is given to 6-membered heteroaryl radicals having up to 2 nitrogen atoms, such as pyridyl, pyrimidyl, pyridazinyl and pyrazinyl, and to 5-membered heteroaryl radicals having up to 2 heteroatoms selected from the group consisting of N, O and S, such as illustratively and preferably thienyl, furyl, pyrrolyl, pyrazolyl, imidazolyl, thiazolyl, oxazolyl, isothiazolyl, and isoxazolyl.

Halogen represents radicals of fluorine, chlorine, bromine and iodine. Preference is given to radicals of fluorine and chlorine.

Oxo represents a doubly bonded oxygen atom.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein $R^1$ is a group of the formula —$NR^7R^8$, —$NR^9$—C(=O)—$R^{10}$, —$NR^{11}$—$SO_2$—$R^{12}$, —$OR^{13}$, —S(=O)$_n$—$R^{14}$ or —$SO_2$—$NR^{15}R^{16}$, wherein n is 0 or 2, $R^7$ is ($C_1$-$C_4$)-alkyl optionally substituted with one or two substituents independently selected from the group consisting of hydroxy, ($C_1$-$C_4$)-alkoxy, amino, mono-($C_1$-$C_4$)-alkylamino and di-($C_1$-$C_4$)-alkylamino, $R^8$, $R^{10}$, $R^{12}$, $R^{13}$ and $R^{14}$ are each selected from the group consisting of ($C_1$-$C_6$)-alkyl, ($C_3$-$C_6$)-cycloalkyl, phenyl, 4- to 6-membered heterocycloalkyl and 5- or 6-membered heteroaryl, wherein (i) said ($C_3$-$C_6$)-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, and (ii) said ($C_1$-$C_6$)-alkyl is optionally substituted with one or two substituents independently selected from the group consisting of fluoro, trifluoromethyl, hydroxy, ($C_1$-$C_4$)-alkoxy, amino, mono-($C_1$-$C_4$)-alkylamino, di-($C_1$-$C_4$)-alkyl-amino, mono-($C_1$-$C_4$)-alkylaminocarbonyl, di-($C_1$-$C_4$)-alkylaminocarbonyl, ($C_3$-$C_6$)-cycloalkyl, phenyl, 4- to 6-membered heterocycloalkyl and 5- or 6-membered heteroaryl, wherein said ($C_3$-$C_6$)-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, $R^9$ is ($C_1$-$C_4$)-alkyl, $R^{11}$ is hydrogen or ($C_1$-$C_4$)-alkyl, or $R^{11}$ and $R^{12}$ are joined and, taken together with the nitrogen atom and $SO_2$ group to which they are attached, form a heterocyclic moiety of the formula

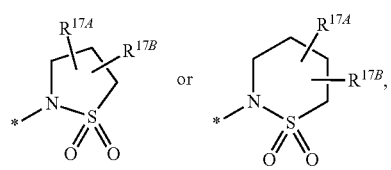

wherein * denotes the point of attachment to the indazole moiety, and $R^{17A}$ and $R^{17B}$ are independently hydrogen or methyl, $R^{15}$ is hydrogen or ($C_1$-$C_4$)-alkyl optionally substituted with one or two substituents independently selected from the group consisting of hydroxy, ($C_1$-$C_4$)-alkoxy, amino, mono-($C_1$-$C_4$)-alkylamino and di-($C_1$-$C_4$)-alkylamino, $R^{16}$ is selected from the group consisting of hydrogen, ($C_1$-$C_6$)-alkyl, ($C_3$-$C_6$)-cycloalkyl, phenyl, 4- to 6-membered heterocycloalkyl and 5- or 6-membered heteroaryl, wherein (i) said ($C_3$-$C_6$)-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, and (ii) said ($C_1$-$C_6$)-alkyl is optionally substituted with one or two substituents independently selected from the group consisting of fluoro, trifluoromethyl, hydroxy, ($C_1$-$C_4$)-alkoxy, amino, mono-($C_1$-$C_4$)-alkylamino, di-($C_1$-$C_4$)-alkyl-($C_3$-$C_6$)-cycloalkyl, phenyl, 4- to 6-membered heterocycloalkyl and 5- or 6-membered heteroaryl, wherein said ($C_3$-$C_6$)-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, ($C_1$-$C_4$)-alkyl, oxo, hydroxy, ($C_1$-$C_4$)-alkoxy, amino, mono-($C_1$-$C_4$)-alkylamino and di-($C_1$-$C_4$)-alkylamino, or $R^{15}$ and $R^{16}$ are joined and, taken together with the nitrogen atom to which they are attached, form a 4- to 6-membered heterocycloalkyl ring, which may contain a second ring heteroatom selected from N, O and S, and which is optionally substituted with one or two substituents independently selected from the group consisting of ($C_1$-$C_4$)-alkyl, oxo, hydroxy, ($C_1$-$C_4$)-alkoxy, amino, mono-($C_1$-$C_4$)-alkyl-amino and di-($C_1$-$C_4$)-alkylamino, $R^2$ is hydrogen, fluoro or chloro, $R^3$ is cyano or a group of the formula —C(=O)—$OR^{18}$ or —C(=O)—$NR^{19}R^{20}$, wherein $R^{18}$ is ($C_1$-$C_4$)-alkyl, and $R^{19}$ and $R^{20}$ are independently selected from the group consisting of hydrogen and ($C_1$-$C_4$)-alkyl, $R^4$ is ($C_1$-$C_4$)-alkyl optionally substituted with up to three fluoro atoms, or is amino, $R^5$ is ($C_1$-$C_6$)-alkyl optionally substituted with up to three fluoro atoms or with one or two substituents independently selected from the group consisting of hydroxy, ($C_1$-$C_4$)-alkoxy, amino, mono-($C_1$-$C_4$)-alkylamino, di-($C_1$-$C_4$)-alkylamino, ($C_3$-$C_6$)-cycloalkyl and 4- to 6-membered heterocycloalkyl, wherein (i) said ($C_1$-$C_4$)-alkoxy substituent is optionally further substituted with a residue selected from the group consisting of hydroxy, ($C_1$-$C_4$)-alkoxy, amino, mono-($C_1$-$C_4$)-alkyl-amino, di-($C_1$-$C_4$)-alkylamino and 4- to 6-membered heterocycloalkyl, and (ii) said mono-($C_1$-$C_4$)-alkylamino and di-($C_1$-$C_4$)-alkylamino substituents are optionally further substituted with one or two residues selected from the group consisting of hydroxy and ($C_1$-$C_4$)-alkoxy, or R$^5$ is selected from the group consisting of $(C_3-C_6)$-cycloalkyl, phenyl and 5- or 6-membered heteroaryl each of which is optionally substituted with one or two substituents independently selected from the group consisting of fluoro, chloro, difluoromethyl, trifluoromethyl, $(C_1-C_4)$-alkyl, hydroxy, $(C_1-C_4)$-alkoxy, mono-$(C_1-C_4)$-alkylamino and di-$(C_1-C_4)$-alkylamino, and R$^6$ is hydrogen or $(C_1-C_4)$-alkyl.

In a further preferred embodiment, the present invention relates to compounds of general formula (I), wherein R$^2$ is hydrogen or fluoro.

In another preferred embodiment, the present invention relates to compounds of general formula (I), wherein R$^3$ is cyano.

In another likewise preferred embodiment, the present invention relates to compounds of general formula (I), wherein R$^4$ is methyl, difluoromethyl, trifluoromethyl or amino.

In another likewise preferred embodiment, the present invention relates to compounds of general formula (I), wherein R$^6$ is hydrogen or methyl.

In a particularly preferred embodiment, the present invention relates to compounds of general formula (I), wherein R$^1$ is a group of the formula —NR$^7$R$^8$, —NR$^9$—C(=O)—R$^{10}$, —NR$^{11}$—SO$_2$—R$^{12}$, —OR$^{13}$, —S(=O)$_n$—R$^{14}$ or —SO$_2$—NR$^{15}$R$^{16}$, wherein n is 0 or 2, R$^7$ is $(C_1-C_4)$-alkyl optionally substituted with hydroxy, methoxy, ethoxy, amino, methylamino, ethylamino, dimethylamino or diethylamino, R$^8$, R$^{10}$, R$^{12}$, R$^{13}$ and R$^{14}$ are each selected from the group consisting of $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, R$^9$ is methyl or ethyl, R$^{11}$ is hydrogen, methyl or ethyl, or R$^{11}$ and R$^{12}$ are joined and, taken together with the nitrogen atom and SO$_2$ group to which they are attached, form a heterocyclic moiety of the formula

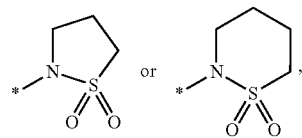 [SMILES: *N1CCCS1(=O)=O ; "or" ; *N1CCCCS1(=O)=O ; ","]

wherein * denotes the point of attachment to the indazole moiety,

R$^{15}$ is hydrogen or $(C_1-C_4)$-alkyl optionally substituted with hydroxy, methoxy, ethoxy, amino, methylamino, ethylamino, dimethylamino or diethylamino, R$^{16}$ is selected from the group consisting of hydrogen, $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or R$^{15}$ and R$^{16}$ are joined and, taken together with the nitrogen atom to which they are attached, form a 5- or 6-membered heterocycloalkyl ring, which may contain a second ring heteroatom selected from N and O, and which is optionally substituted with one or two substituents independently selected from the group consisting of methyl, ethyl, oxo, hydroxy, methoxy, ethoxy, amino, methylamino, ethylamino, dimethylamino and diethylamino, R$^2$ is hydrogen or fluoro, R$^3$ is cyano, R$^4$ is methyl, trifluoromethyl or amino, R$^5$ is $(C_1-C_4)$-alkyl optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino and 5- or 6-membered heterocycloalkyl, wherein (i) said $(C_1-C_4)$-alkoxy substituent is optionally further substituted with a residue selected from the group consisting of methoxy, ethoxy, amino, methylamino, ethylamino, dimethylamino and diethylamino, and (ii) said mono-$(C_1-C_4)$-alkylamino and di-$(C_1-C_4)$-alkylamino substituents are optionally further substituted with one or two residues selected from the group consisting of hydroxy, methoxy and ethoxy, or R$^5$ is $(C_3-C_6)$-cycloalkyl or 5- or 6-membered heteroaryl each of which is optionally substituted with one or two substituents independently selected from the group consisting of fluoro, methyl, ethyl, methylamino, ethylamino, dimethylamino and diethylamino,
and
$R^6$ is hydrogen or methyl.

In a further distinct embodiment, the present invention relates to compounds of general formula (I), wherein
$R^1$ is a group of the formula —$NR^7R^8$, —$NR^{11}$—$SO_2$—$R^{12}$, $OR^{13}$ or —$S(=O)_n$—$R^{14}$, wherein
n is 0 or 2,
$R^7$ is $(C_1$-$C_4)$-alkyl optionally substituted with hydroxy, methoxy, ethoxy, amino, methylamino, ethylamino, dimethylamino or diethylamino,
$R^8$, $R^{12}$, $R^{13}$ and $R^{14}$ are each selected from the group consisting of $(C_1$-$C_4)$-alkyl, $(C_3$-$C_6)$-cycloalkyl and 5- or 6-membered heterocycloalkyl, wherein
(i) said $(C_3$-$C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
and
(ii) said $(C_1$-$C_4)$-alkyl is optionally substituted with one or two substituents independently selected from the group consisting of fluoro, trifluoromethyl, hydroxy, methoxy, ethoxy, isopropoxy, amino, methylamino, ethylamino, dimethylamino, diethylamino, $(C_3$-$C_6)$-cycloalkyl and 5- or 6-membered heterocycloalkyl, wherein said $(C_3$-$C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino,
and
$R^{11}$ is hydrogen or methyl,
$R^2$ is hydrogen or fluoro,
$R^3$ is cyano,
$R^4$ is methyl, difluoromethyl or trifluoromethyl,
$R^5$ is methyl, difluoromethyl or trifluoromethyl,
and
$R^6$ is hydrogen.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

In another embodiment, the present invention relates to a process for preparing the compounds of general formula (I), wherein $R^6$ is hydrogen, characterized in that
[A] an aldehyde of formula (II)

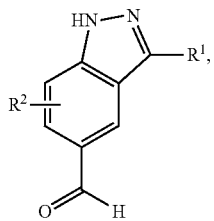

(II)

wherein $R^1$ and $R^2$ have the meanings described above, is reacted in the presence of an acid, an acid/base combination and/or a dehydrating agent with a cyanoenolate of formula (III)

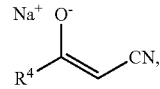

(III)

wherein $R^4$ has the meaning described above,
to give a compound of formula (IV)

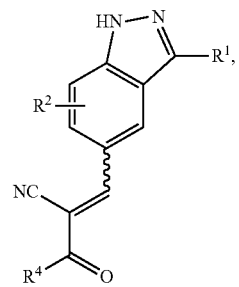

(IV)

wherein $R^1$, $R^2$ and $R^4$ have the meanings described above, and the latter is then condensed with a compound of formula (V)

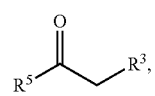

(V)

wherein $R^3$ and $R^5$ have the meanings described above,
in the presence of an ammonia source such as ammonium acetate to give the compound of formula (I-A)

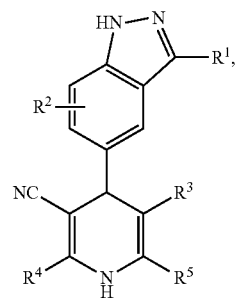

(I-A)

wherein $R^1$, $R^2$, $R^3$, $R^4$ and $R^5$ have the meanings described above,
or
[B] an aldehyde of formula (VI)

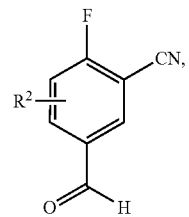

(VI)

wherein $R^2$ has the meaning described above,
is reacted in the presence of an acid, an acid/base combination and/or a dehydrating agent with a cyanoenolate of formula (III)

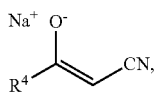 (III)

wherein R$^4$ has the meaning described above,
to give a compound of formula (VII)

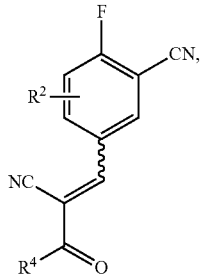 (VII)

wherein R$^2$ and R$^4$ have the meanings described above,
the latter is then condensed with a compound of formula (V)

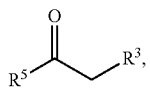 (V)

wherein R$^3$ and R$^5$ have the meanings described above,
in the presence of an ammonia source such as ammonium acetate to give a compound of formula (VIII)

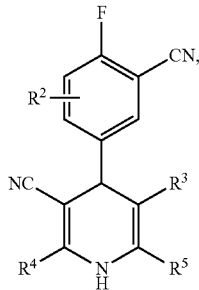 (VIII)

wherein R$^2$, R$^3$, R$^4$ and R$^5$ have the meanings described above,
subsequently the compound of formula (VIII) is treated with hydrazine to yield the 3-aminoindazole of formula (IX)

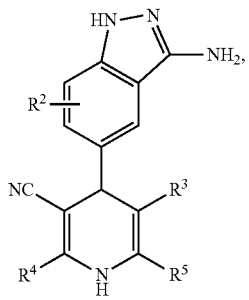 (IX)

wherein R$^2$, R$^3$, R$^4$ and R$^5$ have the meanings described above, then converted by standard methods into the N$^1$-protected derivative of formula (X)

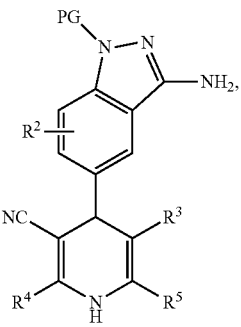 (X)

wherein R$^2$, R$^3$, R$^4$ and R$^5$ have the meanings described above, and

PG represents a suitable indazole-protecting group, preferably tert-butoxycarbonyl, 2-(trimethylsilyl)ethoxymethyl or p-methoxybenzyl, and treated with a sulfonyl chloride of formula (XI)

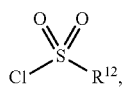 (XI)

wherein R$^{12}$ has the meaning described above, in the presence of a base to give a compound of formula (XII-A)

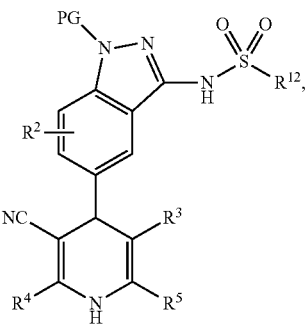 (XII-A)

wherein PG, R$^2$, R$^3$, R$^4$, R$^5$ and R$^{12}$ have the meanings described above, optionally followed by N-alkylation with a compound of formula (XIII)

R$^{114}$—Z (XIII), wherein

R$^{114}$ represents (C$_1$-C$_6$)-alkyl and

Z represents a leaving group such as halogen, mesylate, triflate or tosylate, in the presence of a base to afford a compound of formula (XII-B)

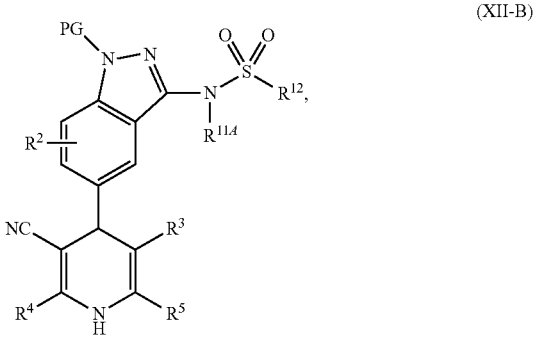

(XII-B)

wherein PG, $R^2$, $R^3$, $R^4$, $R^5$, $R^{11A}$ and $R^{12}$ have the meanings described above, and finally the resulting compounds of formula (XII-A) and (XII-B), respectively, are deprotected by standard procedures to give the compound of formula (I-B)

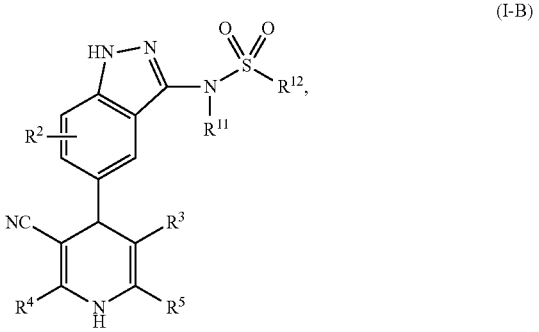

(I-B)

wherein $R^2$, $R^3$, $R^4$, $R^5$, $R^{11}$ and $R^{12}$ have the meanings described above, optionally followed, where appropriate, by (i) separating the compounds (I-A) and (I-B) thus obtained into their respective enantiomers and/or diastereomers, preferably using chromatographic methods, and/or (ii) converting the compounds (I-A) and (I-B) into their respective hydrates, solvates, salts and/or hydrates or solvates of the salts by treatment with the corresponding solvents and/or acids or bases.

Process steps (II)+(III)→(IV), (IV)+(V)→(I-A), (VI)+(III)→(VII) and (VII)+(V)→(VIII) are generally carried out in an inert solvent at a temperature range from +20° C. to the boiling point of the solvent under atmospheric pressure.

Inert solvents suitable for this purpose are, for example, alcohols such as methanol, ethanol, n-propanol, isopropanol, n-butanol or tert-butanol, hydrocarbons such as hexane, cyclohexane, benzene, toluene or xylene, halohydrocarbons such as dichloromethane, trichloromethane, tetrachloromethane, trichloroethane, 1,2-dichloroethane, chlorobenzene or chlorotoluene, ethers such as tetrahydrofuran, 1,4-dioxane or 1,2-dimethoxyethane, or other solvents such as acetonitrile, pyridine or acetic acid. It is likewise possible to use mixtures of these solvents. Reactions (II)+(III)→(IV) and (VI)+(III)→(VII) are preferably performed in dichloromethane, toluene, ethanol or isopropanol at the respective reflux temperature under atmospheric pressure, and reactions (IV)+(V)→(I-A) and (VII)+(V)→(VIII) are preferably carried out in ethanol or isopropanol also at reflux temperature under atmospheric pressure.

Reactions (II)+(III)→(IV) and (VI)+(IQ)→(VII) can advantageously take place in the presence of an acid, of an acid/base combination and/or of a dehydrating agent such as, for example, molecular sieves. Examples of suitable acids are acetic acid, trifluoroacetic acid, methanesulfonic acid or p-toluenesulfonic acid; suitable bases are in particular piperidine or pyridine.

Suitable ammonia sources for reactions (IV)+(V)→(I-A) and (VII)+(V)→(VIII) are, for example, ammonium formate, ammonium acetate, ammonium chloride or ammonium hydrogen-sulfate; preference is given to ammonium acetate [for the synthesis of 1,4-dihydropyridines in general, see, for example, D. M. Stout, A. I. Meyers, Chem. Rev. 1982, 82, 223-243; H. Meier et al., Liebigs Ann. Chem. 1977, 1888; H. Meier et al., ibid. 1977, 1895; H. Meier et al., ibid. 1976, 1762; F. Bossert et al., Angew. Chem. 1981, 93, 755].

The 3-aminoindazole formation in process step (VIII)→(IX) is generally carried out employing an excess of hydrazine or hydrazine hydrate in an alcoholic solvent such as methanol, ethanol, n-propanol, isopropanol, n-butanol or tert-butanol, or in a mixture thereof with water at a temperature range from +20° C. to the boiling point of the solvent under atmospheric pressure. Hydrazine salts may also be used for the conversion in the presence of an auxiliary amine base such as triethylamine, N-methylmorpholine, N-methylpiperidine or N,N-diisopropylethylamine.

Introduction and removal of the indazole-protecting group PG in process steps (IX)→(X) and (XII-A)/(XII-B)→(I-B), respectively, is generally carried out by standard methods well known in the art [see, for example, T. W. Greene and P. G. M. Wuts, Protective Groups in Organic Synthesis, Wiley, New York, 1999; M. Bodanszky and A. Bodanszky, The Practice of Peptide Synthesis, Springer-Verlag, Berlin, 1984]. Preferably used as protecting group in the above process is tert-butoxycarbonyl (Boc), 2-(trimethylsilyl)ethoxymethyl (SEM) or p-methoxybenzyl (PMB). The removal of these groups is preferably carried out by reacting with a strong acid such as hydrogen chloride, hydrogen bromide or trifluoroacetic acid in an inert solvent such as water, dioxane, dichloromethane or acetic acid; it is also possible, where appropriate, for the removal to be carried out without an additional inert solvent. When using the SEM group for indazole protection, cleavage may alternatively be accomplished by treatment with a fluoride source such as potassium fluoride or tetrabutylammonium fluoride in an inert solvent such as tetrahydrofuran.

Inert solvents for process steps (X)+(XI)→(XII-A) and (XII-A)+(XIII)→(XII-B) are, for example, ethers such as diethyl ether, methyl tert-butyl ether, 1,4-dioxane, tetrahydrofuran or 1,2-dimethoxyethane, hydrocarbons such as benzene, toluene, xylene, hexane or cyclohexane, halo-hydrocarbons such as dichloromethane, trichloromethane, tetrachloromethane, 1,2-dichloroethane, trichloroethane, tetrachloroethane, chlorobenzene or chlorotoluene, or other solvents such as N,N-dimethylformamide (DMF), dimethyl sulfoxide (DMSO), N,N'-dimethylpropylene urea (DMPU), N-methylpyrrolidinone (NMP), pyridine or acetonitrile. It is also possible to use mixtures of said solvents. Dichloromethane, tetrahydrofuran, dimethylformamide or mixtures thereof are preferably employed.

Bases suitable for process steps (X)+(XI)→(XII-A) and (XII-A)+(XIII)→(XII-B) are in particular alkali metal or alkaline earth metal carbonates such as lithium, sodium, potassium, calcium or cesium carbonate, alkali metal hydrides such as sodium or potassium hydride, sterically hindered alkali alkoxides such as sodium or potassium tert-butoxide, sterically hindered alkali amides such as lithium, sodium or potassium bis(trimethylsilyl)amide or lithium diisopropylamide, or organic amines such as triethylamine, N-methylmorpholine, N-methylpiperidine, N,N-diisopropylethylamine or pyridine. Potassium carbonate, cesium carbonate, sodium hydride or triethylamine is preferably used.

The reactions (X)+(XI)→(XII-A) and (XII-A)+(XIII)→(XII-B) are generally performed under atmospheric pressure in a temperature range from −20° C. to +120° C., preferably at 0° C. to +80° C.

In the alkylation step (XII-A)+(XIII)→(XII-B), temporary protection of the dihydropyridine nitrogen by, for example, an acetyl group may be advantageous in some cases to avoid double N-alkylation (unless intended otherwise, compare preparation methods [α] and [D] described below).

Compounds of the invention having the formula (I-C)

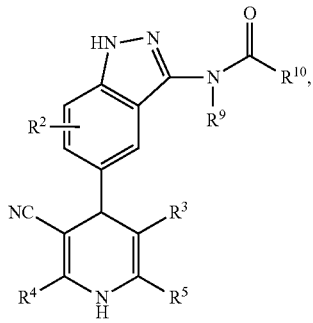

(I-C)

wherein $R^2$, $R^3$, $R^4$, $R^5$, $R^9$ and $R^{10}$ have the meanings described above,
can be prepared in analogy to the reaction sequence (X)→(XII-A)→(XII-B)→(I-B) described above by acylating the compound of formula (X) with a carboxylic acid chloride of formula (XIV)

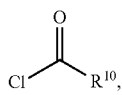

(XIV)

wherein $R^{10}$ has the meaning described above,
in the presence of a base to yield a compound of formula (XV-A)

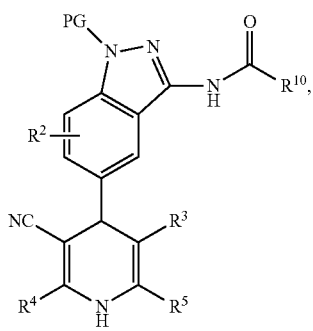

(XV-A)

wherein PG, $R^2$, $R^3$, $R^4$, $R^5$ and $R^{10}$ have the meanings described above,
followed by N-alkylation with a compound of formula (XVI)

$R^9$—Z  (XVI), wherein $R^9$ and Z have the meanings described above,
in the presence of a base to give a compound of formula (XV-B)

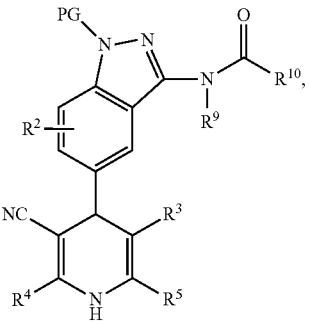

(XV-B)

wherein PG, $R^2$, $R^3$, $R^4$, $R^5$, $R^9$ and $R^{10}$ have the meanings described above,
and subsequent removal of the protecting group PG using standard procedures.

To steps (X)+(XIV)→(XV-A) and (XV-A)+(XVI)→(XV-B), the reaction parameters such as solvents, bases and temperatures described for reactions (X)+(XI)→(XII-A) and (XIII-A)+(XIII)→(XII-B) are applied analogously.

In the alkylation step (XV-A)+(XVI)→(XV-B), temporary protection of the dihydropyridine nitrogen by, for example, an acetyl group may again be advantageous to avoid double N-alkylation (unless intended otherwise, compare preparation methods [C] and [D] described below).

Compounds of formula (I), wherein $R^6$ is $(C_1-C_4)$-alkyl or cyclopropyl, can be prepared

[C] from the compound of formula (I-A) by first converting the latter by standard methods into the indazole-protected derivative of formula (XVII)

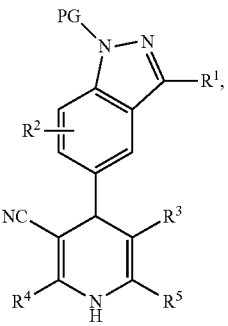

(XVII)

wherein PG, $R^1$, $R^2$, $R^3$, $R^4$ and $R^5$ have the meanings described above,
followed by N-alkylation with a compound of formula (XVIII)

$R^{6A}$—Z  (XVIII), wherein Z has the meaning described above,
and
$R^{6A}$ represents $(C_1-C_4)$-alkyl or cyclopropyl,
in the presence of a base to afford a compound of formula (XIX)

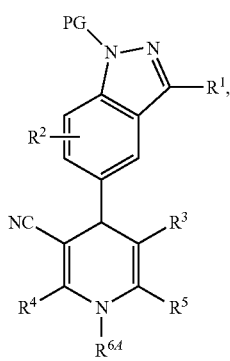

(XIX)

wherein PG, $R^1$, $R^2$, $R^3$, $R^4$, $R^5$ and $R^{6A}$ have the meanings described above,
and subsequent removal of the protecting group PG using standard procedures to give the compound of formula (I-D)

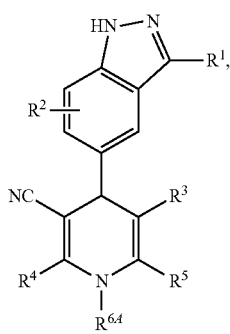

(I-D)

wherein $R^1$, $R^2$, $R^3$, $R^4$, $R^5$ and $R^{6A}$ have the meanings described above, or

[D] from the compound of formula (VIII) by N-alkylation with the compound of formula (XVIII)

$R^{6A}$—Z  (XVIII), wherein $R^{6A}$ and Z have the meanings described above,
in the presence of a base to afford a compound of formula (XX)

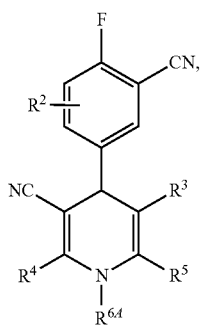

(XX)

wherein $R^2$, $R^3$, $R^4$, $R^5$ and $R^{6A}$ have the meanings described above, followed by further transformations analogous to the reaction sequences (VIII)→(X)→(I-B) and (X)→(I-C) described above to give the compound of formula (I-E)

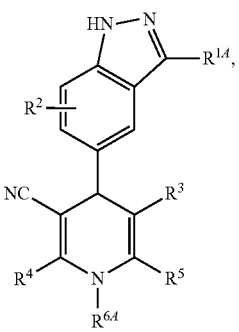

(I-E)

wherein $R^2$, $R^3$, $R^4$, $R^5$ and $R^{6A}$ have the meanings described above,
and
$R^{1A}$ represents a group of the formula —$NR^9$—C(=O)—$R^{10}$ or —$NR^{11}$—$SO_2$—$R^{12}$ as defined above.

For steps (XVII)+(XVIII)→(XIX) and (VIII)+(XVIII)→(XX), the reaction parameters such as solvents, bases and temperatures described for reaction (XII-A)+(XIII)→(XII-B) are employed similarly.

Compounds of formula (I), wherein $R^3$ is cyano and both $R^4$ and $R^5$ represent cyclopropyl or an identical ($C_1$-$C_4$)-alkyl residue [i.e. compounds of formula (I) having a symmetrical 1,4-dihydropyridine substructure], can alternatively be prepared

[E] by condensing the aldehyde of formula (II) in the presence of an acid with two equivalents of the compound (XXI)

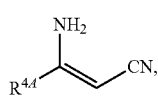

(XXI)

wherein
$R^{4A}$ represents ($C_1$-$C_4$)-alkyl or cyclopropyl,
to give the compound of formula (I-F)

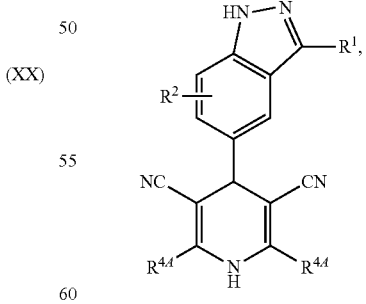

(I-F)

wherein $R^1$, $R^2$ and $R^{4A}$ have the meanings described above, or

[F] by condensing the aldehyde of formula (VI) in the presence of an acid with two equivalents of the compound (XXI)

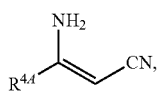

wherein $R^{4A}$ has the meaning described above,
to yield a compound of formula (XXII)

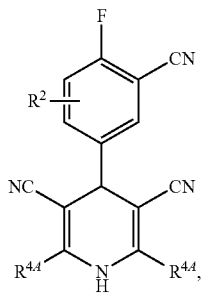

wherein $R^2$ and $R^{4A}$ have the meanings described above,
which is then subjected to further transformations analogous to the reaction sequences (VIII)→(X)→(I-B) and (X)→(I-C) described above to give the compound of formula (I-G)

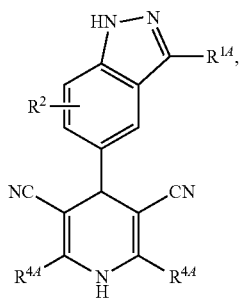

wherein $R^2$ and $R^{4A}$ have the meanings described above, and
$R^{1A}$ represents a group of the formula —NR$^9$—C(=O)—R$^{10}$ or —NR$^{11}$—SO$_2$—R$^{12}$ as defined above.

Process steps (II)+(XXI)→(I-F) and (VI)+(XXI)→(XXII) are usually performed in protic organic solvents like alcohols, such as methanol, ethanol, n-propanol, isopropanol, n-butanol or tert-butanol, or acetic acid. It is likewise possible to use mixtures of these solvents. Examples of suitable acid catalysts for said reactions are acetic acid, trifluoroacetic acid, methanesulfonic acid and p-toluenesulfonic acid. Preferably, acetic acid is simultaneously used as solvent and acid catalyst.

The reactions (II)+(XXI)→(I-F) and (VI)+(XXI)→(XXII) are generally carried out at a temperature range from +20° C. to +120° C., preferably from +65° C. to +120° C., under atmospheric pressure.

Derivatives of the compounds of formula (I-F) and (I-G) that are alkylated at the dihydropyridine nitrogen with an $R^{6A}$ residue, as defined above, can be obtained by subjecting the compound of formula (I-F) or (XXII), respectively, to similar transformations as described in process variants [C] and [D].

The compounds of formula (II) are known from the literature or can be prepared from readily available starting materials by adaptation of standard methods described in the literature [see, for example, G. Luo et al., *J. Org. Chem.* 71, 5392 (2006), and procedures described in WO 2007/124288-A1, WO 2005/056550-A2, US 2005/0227968-A1 and EP 1 510 516-A1]. In one synthetic route, the parent indazolyl aldehyde of formula (XXIII)

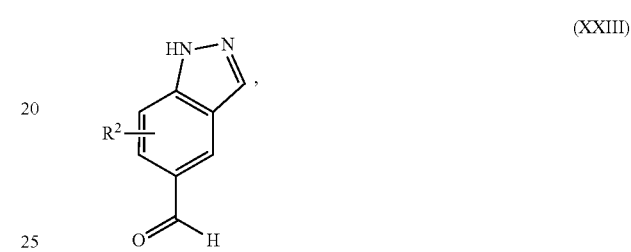

wherein $R^2$ has the meaning described above,
is first halogenated in 3-position and converted into the di-protected derivative of formula (XXIV)

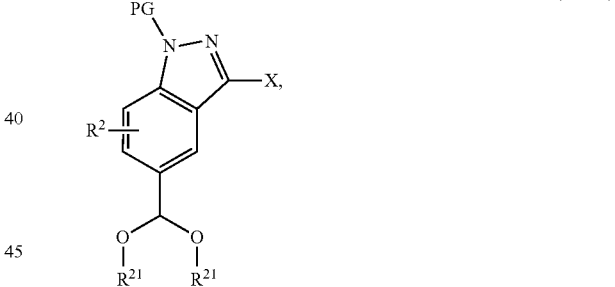

wherein PG and $R^2$ have the meanings described above,
X represents chloro, bromo or iodo,
and
$R^{21}$ represents (C$_1$-C$_4$)-alkyl, or both $R^{21}$ residues together form a —(CH$_2$)$_2$— or —(CH$_2$)$_3$— bridge, using standard procedures, and the compound of formula (XXIV) is then coupled by means of a suitable transition metal catalyst, preferably employing copper or palladium catalysts, with a compound of formula (XXV)

$$R^{1B}—H \qquad (XXV),$$

wherein
$R^{1B}$ represents an N-, O- or S-linked $R^1$ residue of the formula —NR$^7$R$^8$, —OR$^{13}$ or —S(=O)$_n$—R$^{14}$, respectively, as defined above, to yield a compound of formula (XXVI)

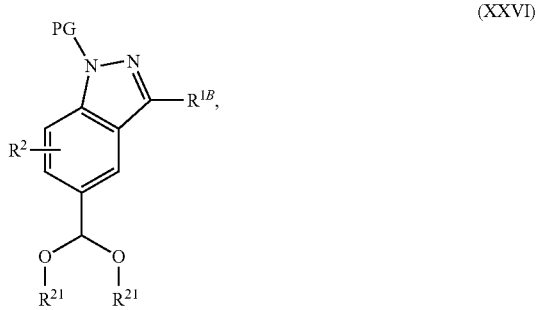

(XXVI)

wherein PG, $R^{1B}$, $R^2$ and $R^{21}$ have the meanings described above, and finally the protecting groups are sequentially or simultaneously removed using standard methods to give the 3-substituted indazolyl aldehyde of formula (II-A)

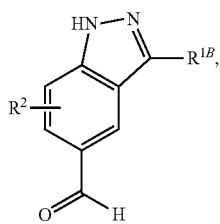

(II-A)

wherein $R^{1B}$ and $R^2$ have the meanings described above.

Inert solvents suitable for process step (XXIV)+(XXV)→(XXVI) include, for example, aromatic hydrocarbons such as benzene, toluene and xylene, ethers such as diethyl ether, diisopropyl ether, methyl tert-butyl ether, 1,2-dimethoxyethane, tetrahydrofuran, 1,4-dioxane and bis-(2-methoxyethyl)-ether, or dipolar-aprotic solvents such as acetonitrile, dimethylsulfoxide (DMSO), N,N-dimethylformamide (DMF), N,N-dimethylacetamide (DMA), N-methylpyrrolidinone (NMP) and N,N'-dimethylpropylene urea (DMPU). It is also possible to use mixtures of these solvents. Preferred solvents are toluene, tetrahydrofuran, 1,4-dioxane, N,N-dimethylformamide and mixtures thereof.

The coupling reaction (XXIV)+(XXV)→(XXVI) is carried out with the aid of a transition metal catalyst. Suitable for this purpose are in particular copper catalysts such as copper (I) iodide, and palladium catalysts such as palladium on activated charcoal, palladium(II) acetate, bis(dibenzylideneacetone)-palladium(0), tris(dibenzylideneacetone)-dipalladium(0), tetrakis(triphenylphosphine)-palladium(0), bis(triphenylphosphine)-palladium(II) chloride, bis(acetonitrile)-palladium(II) chloride or [1,1'-bis(diphenylphosphino)ferrocene]-palladium(II) chloride, optionally in combination with additional phosphane ligands such as, for example, dicyclohexyl[2',4',6'-tris(1-methyl-ethyl)biphenyl-2-yl]phosphane (XPHOS) or 4,5-bis(diphenylphosphino)-9,9-dimethylxanthene (Xantphos) [see, for example, J. Hassan et al., *Chem. Rev.* 102, 1359-1469 (2002)].

Process step (XXIV)+(XXV)→(XXVI) is usually performed at a temperature range from +20° C. to +200° C., preferably from +80° C. to +180° C., at atmospheric pressure. However, it is also possible to run this reaction at elevated pressure or at reduced pressure (for example in a range from 0.5 to 5 bar). Furthermore, said reaction can advantageously be carried out by means of concomitant microwave irradiation.

The compounds of the formulae (H), (V), (VI), (XI), (XIII), (XIV), (XVI), (XVIII), (XXI), (XXIII) and (XXV) are either commercially available, known from the literature, or can be prepared from readily available starting materials employing standard methods described in the literature.

The preparation of the compounds of the invention can be illustrated by means of the following synthesis schemes 1-4. More detailed procedures are presented below in the experimental section describing the Examples.

Scheme 1

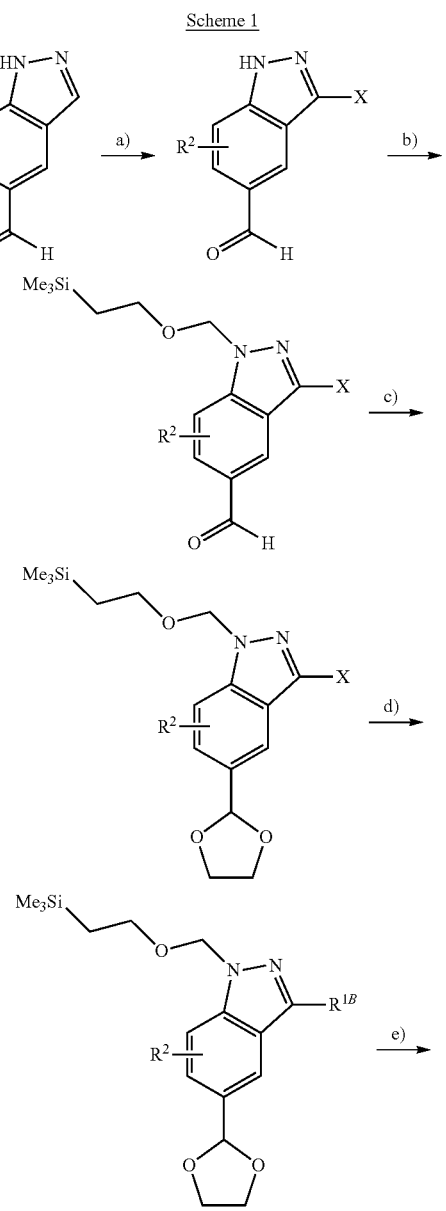

-continued
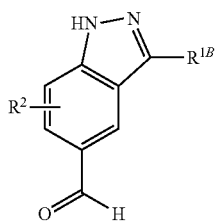
[a]: NCS (X = Cl) or NBS (X = Br) or I₂/aq. NaOH (X = I); b): Me₃SiCH₂CH₂OCH₂Cl, Cs₂CO₃; c): HOCH₂CH₂OH, cat. p-TsOH; d): R^{1B}=H, Cu(I) or Pd(0) catalyst; e): aq. HCl].
Scheme 2
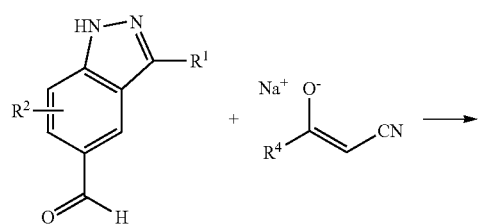
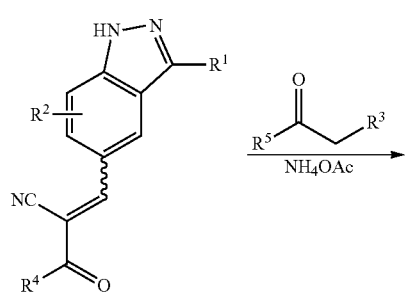
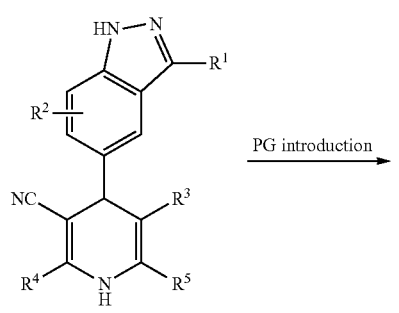
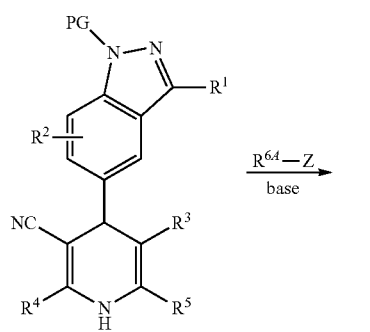
-continued
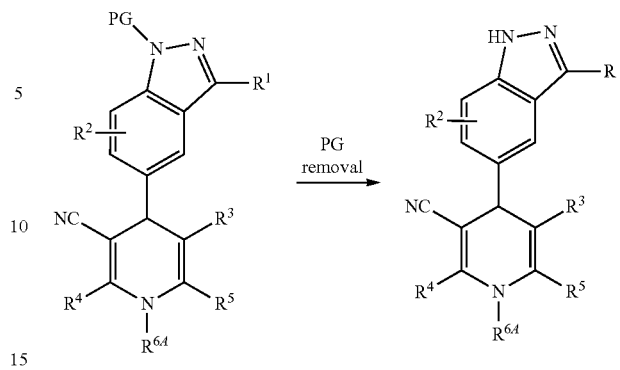
Scheme 3
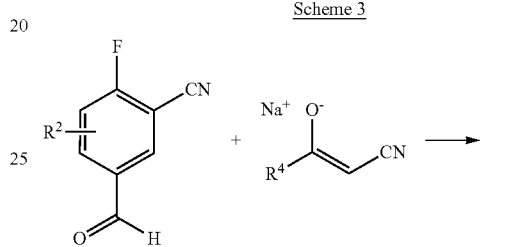
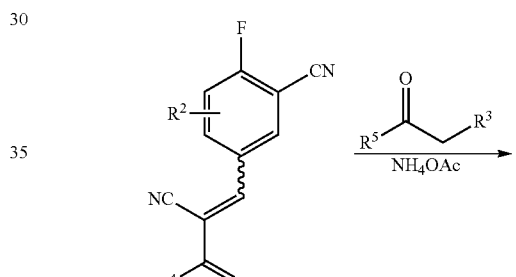
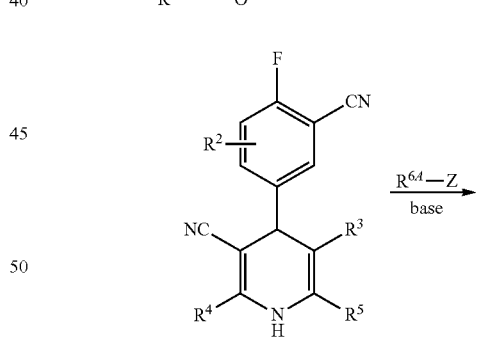
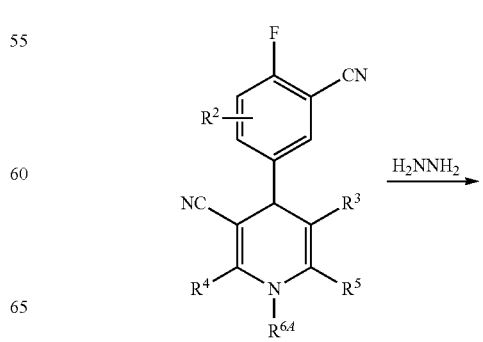

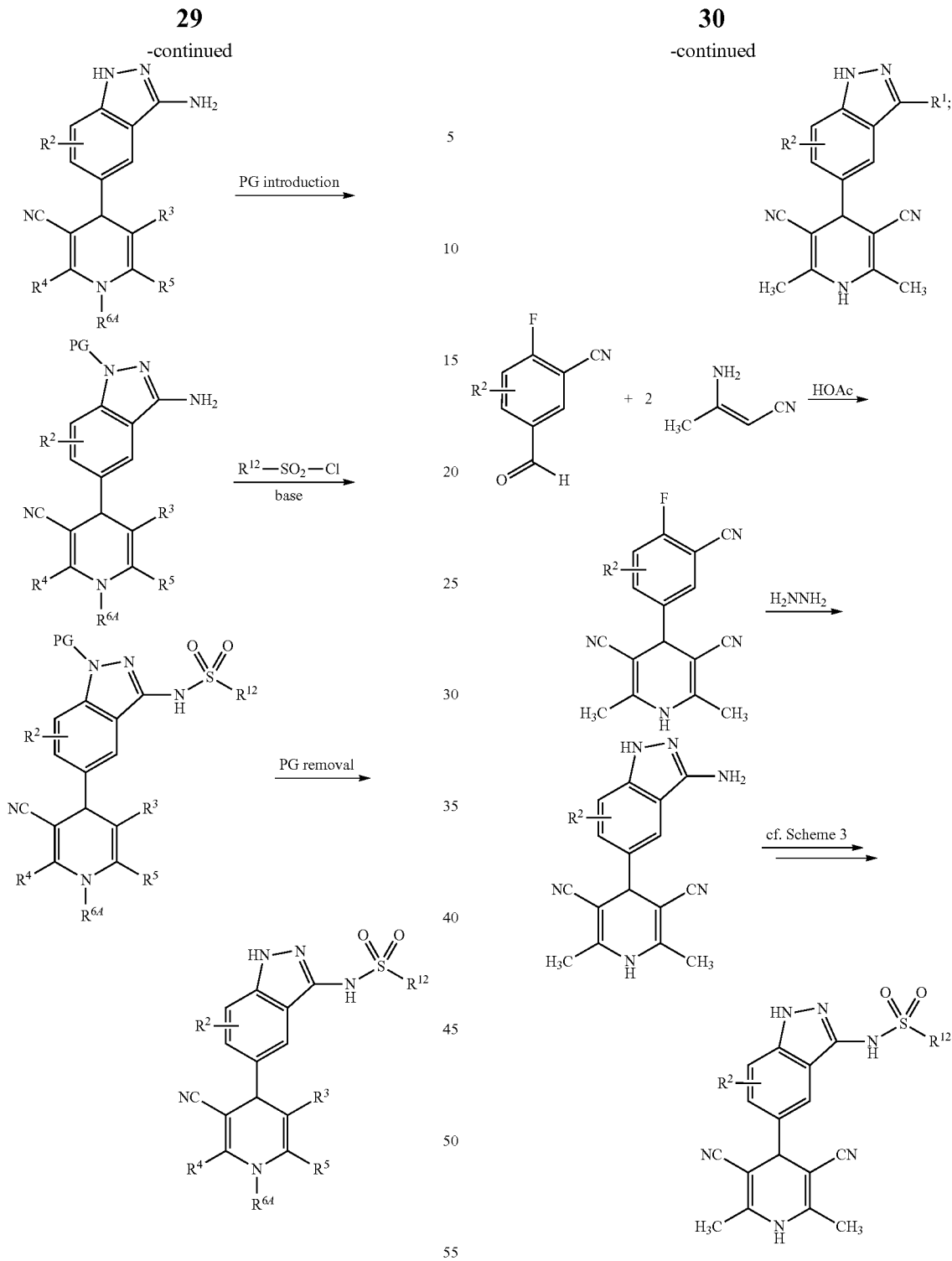

Methods of Use

The compounds of the present invention may be used to inhibit the activity or expression of receptor tyrosine kinases, particularly of the c-Met receptor tyrosine kinase. Therefore, the compounds of formula (I) are expected to be valuable as therapeutic agents. Accordingly, in another embodiment, the present invention provides a method of treating disorders relating to or mediated by c-Met kinase activity in a patient in need of such treatment, comprising administering to the patient an effective amount of a compound of formula (I) as Scheme 4

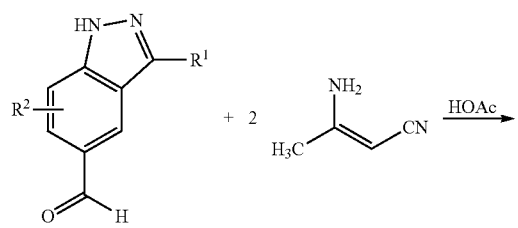

defined above. In certain embodiments, the disorders relating to c-Met kinase activity are cell proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by c-Met" shall include diseases associated with or implicating c-Met activity, for example the hyperactivity of c-Met, and conditions that accompany with these diseases. Examples of "disorders relating to or mediated by c-Met" include disorders resulting from overstimulation of c-Met due to abnormally high amount of c-Met or mutations in c-Met, or disorders resulting from abnormally high amount of c-Met activity due to abnormally high amount of c-Met or mutations in c-Met.

The term "hyperactivity of c-Met" refers to either c-Met expression in cells which normally do not express c-Met or c-Met activity by cells which normally do not possess active c-Met or increased c-Met expression leading to unwanted cell proliferation or mutations leading to constitutive activation of c-Met.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof, Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors (for example, EGFR inhibitors), mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other coadministered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

| Abbreviations and Acronyms: | |
|---|---|
| aq. | aqueous (solution) |
| Boc | tert-butoxycarbonyl |
| br. s | broad singlet (NMR) |
| cat. | catalytic |
| conc. | concentrated |
| d | doublet (NMR) |
| DCI | direct chemical ionization (MS) |
| dd | doublet of doublets (NMR) |
| DMF | N,N-dimethylformamide |
| DMSO | dimethylsulfoxide |

| Abbreviations and Acronyms: | |
|---|---|
| DMSO-$d_6$ | dimethylsulfoxide-$d_6$ |
| equiv. | equivalent(s) |
| ESI | electro-spray ionization (MS) |
| Et | ethyl |
| h | hour(s) |
| $^1$H-NMR | proton nuclear magnetic resonance spectrometry |
| HOAc | acetic acid |
| HPLC | high performance/high pressure liquid chromatography |
| LC-MS | liquid chromatography-coupled mass spectrometry |
| m | multiplet (NMR) |
| Me | methyl |
| MeOH | methanol |
| min | minute(s) |
| MS | mass spectrometry |
| m/z | mass-to-charge ratio |
| NBS | N-bromosuccinimide |
| NCS | N-chlorosuccinimide |
| OAc | acetate |
| of th. | of theory (chemical yield) |
| p-TsOH | para-toluene sulfonic acid |
| q | quartet (NMR) |
| $R_f$ | TLC retention factor |
| RP | reverse phase (HPLC) |
| rt | room temperature |
| $R_t$ | retention time (HPLC) |
| s | singlet (NMR) |
| SEM | 2-(trimethylsilyl)ethoxymethyl |
| sept | septet (NMR) |
| tBu | tert-butyl |
| TFA | trifluoroacetic acid |
| THF | tetrahydrofuran |
| TLC | thin layer chromatography |
| t | triplet (NMR) |
| v/v | volume-to-volume ratio |
| w/v | weight-to-volume ratio |
| w/w | weight-to-weight ratio |

LC-MS Methods:

Method 1:

Instrument: Micromass Quattro Premier with HPLC Waters HPLC Acquity; column: Thermo Hypersil GOLD 1.9µ, 50 mm×1 mm; eluent A: 1 L water+0.5 mL 50% formic acid, eluent B: 1 L acetonitrile+0.5 mL 50% formic acid; gradient: 0.0 min 90% A→0.1 min 90% A→1.5 min 10% A→2.2 min 10% A; oven: 50° C.; flow rate: 0.33 mL/min; UV detection: 210 nm.

Method 2:

Instrument: Micromass Quattro Micro with HPLC Agilent 1100 Series; column: Thermo Hypersil GOLD 3µ, 20 mm×4 mm; eluent A: 1 L water+0.5 mL 50% formic acid, eluent B: 1 L acetonitrile+0.5 mL 50% formic acid; gradient: 0.0 min 100% A→3.0 min 10% A→4.0 min 10% A→4.01 min 100% A (flow rate 2.5 mL/min)→5.00 min 100% A; oven: 50° C.; flow rate: 2 mL/min; UV detection: 210 nm.

Method 3:

Instrument: Micromass ZQ with HPLC HP 1100 Series; UV DAD; column: Phenomenex Gemini 3µ, 30 mm×3.00 mm; eluent A: 1 L water+0.5 mL 50% formic acid, eluent B: 1 L acetonitrile+0.5 mL 50% formic acid; gradient: 0.0 min 90% A→2.5 min 30% A→3.0 min 5% A→4.5 min 5% A; flow rate: 0.0 min 1 mL/min, 2.5 min/3.0 min/4.5 min 2 mL/min; oven: 50° C.; UV detection: 210 nm.

Method 4:

Instrument: Micromass ZQ with HPLC Waters Alliance 2795; column: Phenomenex Synergi 2.5µ MAX-RP 100A Mercury 20 mm×4 mm; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.

Method 5:
Instrument: Waters Acquity SQD HPLC system; column: Waters Acquity HPLC HSS T3 1.8μ 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; flow rate: 0.40 mL/min; oven: 50° C.; UV detection: 210-400 nm.
Starting Materials and Intermediates:

Example 1A 4-(3-Cyano-4-fluorophenyl)-2,6-dimethyl-1,4-dihydropyridine-3,5-dicarbonitrile

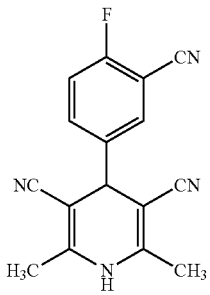

30 g (201.2 mmol) 2-fluoro-5-formylbenzonitrile and 35 g (431.6 mmol) 3-aminocrotononitrile were dissolved in acetic acid (500 ml) and heated to 90° C. After 4 h, the reaction mixture was cooled to rt, concentrated, neutralized with a saturated aqueous solution of sodium bicarbonate, and extracted with ethyl acetate. The organic extracts were combined, dried over sodium sulfate and concentrated under reduced pressure. The remaining solid was dissolved in ethyl acetate, and hexane was added. The precipitate was filtered off to afford the title compound (45 g, 80% of th.) as a pale yellow solid.

$^1$H-NMR (400 MHz, DMSO-$d_6$): δ=9.61 (br. s, 1H), 7.97 (dd, 1H), 7.48 (dd, 1H), 7.35 (dd, 1H), 4.64 (s, 1H), 2.01 (s, 6H) ppm.

Example 2A 4-(3-Amino-1H-indazol-5-yl)-2,6-dimethyl-1,4-dihydropyridine-3,5-dicarbonitrile

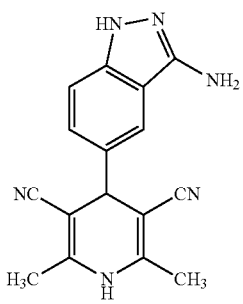 [SMILES: CC1=C(C#N)C(c2ccc3[nH]nc(N)c3c2)C(C#N)=C(C)N1]

A mixture of 9.5 g (34.1 mmol) 4-(3-cyano-4-fluorophenyl)-2,6-dimethyl-1,4-dihydropyridine-3,5-dicarbonitrile (Example 1A) and 10 g (312 mmol) hydrazine hydrate in n-butyl alcohol (75 ml) was stirred at 80° C. for 5 h. The mixture was cooled and concentrated under reduced pressure. Saturated aqueous sodium bicarbonate solution was added to the residue, and the mixture was extracted with ethyl acetate. The organic phases were combined, dried over sodium sulfate, and concentrated under reduced pressure to afford the title compound (5.6 g, 57% of th.) as a pale yellow solid.

$^1$H-NMR (300 MHz, DMSO-$d_6$): δ=11.39 (br. s, 1H), 9.47 (br. s, 1H), 7.50 (m, 1H), 7.20 (d, 1H), 7.11 (dd, 1H), 5.34 (br. s, 2H), 4.34 (s, 1H), 2.01 (s, 6H) ppm.

Example 3A

Tert-Butyl 3-amino-5-(3,5-dicyano-2,6-dimethyl-1,4-dihydropyridin-4-yl)-1H-indazole-1-carboxylate

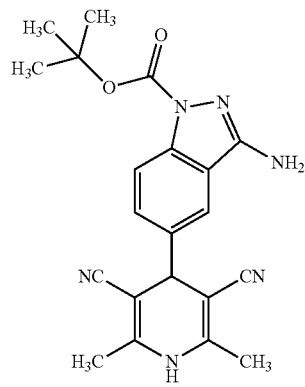 [SMILES: CC1=C(C#N)C(c2ccc3c(c2)c(N)nn3C(=O)OC(C)(C)C)C(C#N)=C(C)N1]

A mixture of 5.0 g (17.2 mmol) 4-(3-amino-1H-indazol-5-yl)-2,6-dimethyl-1,4-dihydropyridine-3,5-dicarbonitrile (Example 2A), 3.7 ml (27 mmol) triethylamine, 0.5 g (4.1 mmol) 4-N,N-dimethylaminopyridine and 5.6 g (77.5 mmol) di-tert-butyldicarbonate in anhydrous THF (750 ml) was stirred over night at room temperature. The reaction mixture was partitioned between ethyl acetate and water, and the separated organic extract was washed with saturated aqueous sodium chloride solution, concentrated under reduced pressure to a residual volume of 40 ml, and cooled with stirring in an ice bath. The resulting precipitate was filtered off, washed with a small amount of cold ethyl acetate, and dried under vacuum to afford the title compound (4.4 g, 66% of th.) as a pale yellow solid.

$^1$H-NMR (DMSO-$d_6$, 300 MHz): δ=9.53 (br. s, 1H), 7.91 (d, 1H), 7.71 (m, 1H), 7.41 (dd, 1H), 6.34 (br. s, 2H), 4.47 (s, 1H), 2.02 (s, 6H), 1.55 (s, 9H) ppm.

Example 4A

3-Iodo-1H-indazole-5-carbaldehyde

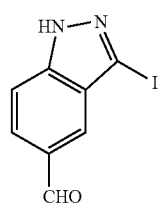 [SMILES: O=Cc1ccc2[nH]nc(I)c2c1]

20 g (137 mmol) 1H-indazole-5-carbaldehyde [preparation described in US 2005/0227968-A1 (Intermediate 1)], dissolved in 1,4-dioxane (640 ml), were treated with a solution of sodium hydroxide (82 g, 2053 mmol) in water (640 ml). Then, 43.2 g (170 mmol) iodine were added, and the mixture was stirred at room temperature for 1 h. Subsequently, a second batch of 43.2 g (170 mmol) iodine was added, and the mixture was again stirred at room temperature for 1 h. The mixture was concentrated under reduced pressure yielding a solid precipitate. After filtration, the precipitate was washed with water and dried under high vacuum over phosphorous oxide in a desiccator for 12 h affording the title compound (26.6 g, 72% of th.) as a pale yellow solid.

$^1$H-NMR (400 MHz, DMSO-$d_6$): δ=9.81 (s, 1H), 7.74 (d, 1H), 7.40 (d, 1H), 7.32 (dd, 1H) ppm.

Example 5A

3-Iodo-1-{[2-(trimethylsilyl)ethoxy]methyl}-1H-indazole-5-carbaldehyde

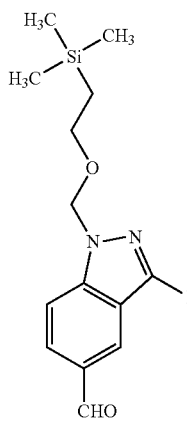

21.6 g (79.5 mmol) 3-iodo-1H-indazole-5-carbaldehyde (Example 4A), dissolved in DMF (100 ml), and 31.1 g (95.4 mmol) cesium carbonate were slowly treated with 15.9 g (95.4 mmol) 2-(trimethylsilyl)ethoxymethyl chloride at 0° C. The mixture was warmed to room temperature, and stirring was continued for 12 h. The solids were then filtered off, and the filtrate was evaporated to dryness yielding the title compound (26.4 g, 82% of th.).

$^1$H-NMR (400 MHz, DMSO-$d_6$): δ=10.22 (s, 1H), 8.26 (d, 1H), 8.09 (dd, 1H), 8.05 (d, 1H), 5.92 (s, 2H), 3.65 (t, 2H), 0.91 (t, 2H), 0.00 (s, 9H) ppm.

Example 6A 5-(1,3-Dioxolan-2-yl)-3-iodo-1-{[2-(trimethylsilyl)ethoxy]methyl}-1H-indazole

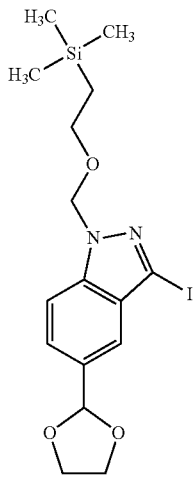 [SMILES: C[Si](C)(C)CCOCn1nc(I)c2cc(C3OCCO3)ccc21]

6.11 g (15.2 mmol) 3-iodo-1-{[2-(trimethylsilyl)ethoxy]methyl}-1H-indazole-5-carbaldehyde (Example 5A), 2.82 g (45.6 mmol) ethylene glycol and a trace amount of p-toluene sulfonic acid in toluene (100 ml) were heated to reflux overnight using a Dean-Stark trap. After cooling, the mixture was extracted twice with saturated aqueous sodium bicarbonate solution and washed with brine. The organic layer was dried with sodium sulfate, filtered and evaporated to dryness. The remaining substance was purified by preparative RP-HPLC (acetonitrile/water gradient) yielding 3.94 g (58% of th.) of the pure title compound.

$^1$H-NMR (400 MHz, DMSO-$d_6$): δ=7.90 (d, 1H), 7.69 (dd, 1H), 7.63 (s, 2H), 5.87 (s, 2H), 4.23 (m, 2H), 4.09 (m, 2H), 3.62 (t, 2H), 0.89 (t, 2H), 0.00 (s, 9H) ppm.

Example 7A 3-(Benzylsulfanyl)-5-(1,3-dioxolan-2-yl)-1-{[2-(trimethylsilyl)ethoxy]methyl}-1H-indazole

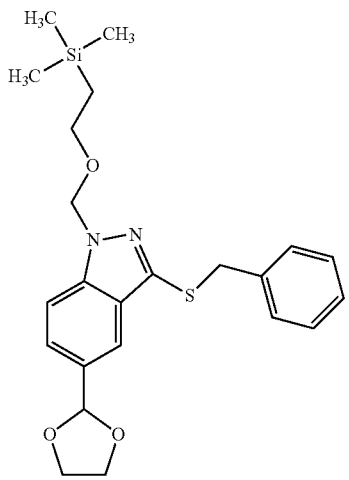 [SMILES: C[Si](C)(C)CCOCn1nc(SCc2ccccc2)c2cc(C3OCCO3)ccc21]

Representative procedure for indazol-3-yl thioether formation:

A flask containing 100 mg (0.224 mmol) 5-(1,3-dioxolan-2-yl)-3-iodo-1-{[2-(trimethylsilyl)-ethoxy]methyl}-1H-indazole (Example 6A) and 6.4 mg (0.011 mmol) 4,5-bis(diphenylphosphino)-9,9-dimethylxanthene (Xantphos) in 1,4-dioxane (6 ml) was evacuated and re-filled with argon gas for three times. Subsequently, 78 μl (0.448 mmol) N,N-diisopropylethylamine, 25 mg (0.202 mmol) phenylmethanethiol and 5 mg (0.006 mmol) tris(dibenzylideneacetone)-dipalladium (Pd$_2$dba$_3$) were added, and the mixture was heated to 100° C. for 3 h under argon atmosphere. After cooling, the reaction mixture was filtered, and the filtrate was purified by preparative RP-HPLC (acetonitrile/water+0.05% TFA gradient) to give 69 mg of a product mixture containing the title compound. This mixture was used in the next step without further purification.

LC-MS (method 2): R$_t$=2.95 min; MS (ESIpos): m/z=443 (M+H)$^+$.

Example 8A 3-(Benzylsulfanyl)-1H-indazole-5-carbaldehyde

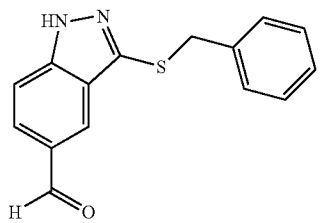 [SMILES: O=Cc1ccc2[nH]nc(SCc3ccccc3)c2c1]

Representative procedure for 2-(trimethylsilyl)ethoxymethyl (SEM) group removal using hydrochloric acid:

The product mixture obtained in Example 7A was dissolved in ethanol (4 ml), treated with 3 N hydrochloric acid (1 ml) and heated to 90° C. for 4 h. After this time, 3 N hydrochloric acid (0.2 ml) was again added, and heating was continued for 3 h. The mixture was evaporated to dryness, and the crude product thus obtained was used in the next step without further purification.

LC-MS (method 2): R$_t$=2.10 min; MS (ESIpos): m/z=269 (M+H)$^+$.

Example 9A 5-(1,3-Dioxolan-2-yl)-3-(methylsulfonyl)-1-{[2-(trimethylsilyl)ethoxy]methyl}-1H-indazole

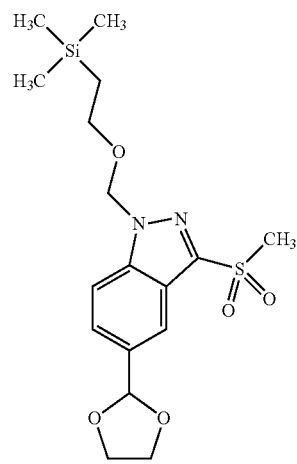 [SMILES: C[Si](C)(C)CCOCn1nc(S(C)(=O)=O)c2cc(C3OCCO3)ccc21]

Representative procedure for copper(I)-mediated coupling of indazol-3-yl iodides with sulfinates:

To a microwave-flask containing 100 mg (0.224 mmol) 5-(1,3-dioxolan-2-yl)-3-iodo-1-{[2-(trimethylsilyl)ethoxy]methyl}-1H-indazole (Example 6A) and 68 mg (0.672 mmol) sodium methane-sulfinate in DMF (4 ml) were added 128 mg (0.672 mmol) copper(I) iodide. The flask was filled with argon, sealed and heated to 180° C. for 1 h using microwave irradiation. After cooling, the reaction mixture was filtered, and the filtrate was purified by preparative RP-HPLC (acetonitrile/water+0.05% TFA gradient) to give 55 mg of a product mixture containing the title compound. This mixture was used in the next step without further purification.

LC-MS (method 2): R$_t$=2.39 min; MS (ESIpos): m/z=399 (M+H)$^+$.

Example 10A 3-(Methylsulfonyl)-1H-indazole-5-carbaldehyde

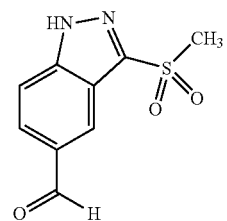

The title compound was prepared from Example 9A in analogy to the procedure described in Example 8A. The crude product thus obtained was used in the next step without further purification.

LC-MS (method 2): R$_t$=1.23 min; MS (ESIpos): m/z=225 (M+H)$^+$.

Example 11A

3-Ethoxy-1-{[2-(trimethylsilyl)ethoxy]methyl}-1H-indazole-5-carbaldehyde

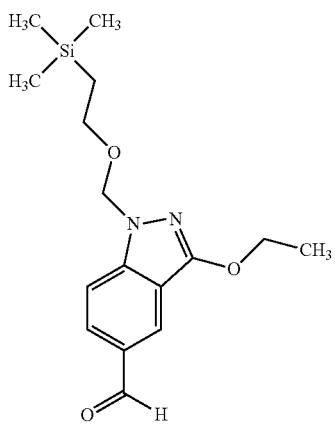 [SMILES: CCOc1nn(COCC[Si](C)(C)C)c2ccc(C=O)cc12]

Representative procedure for copper(I)-catalyzed coupling of indazol-3-yl iodides with aliphatic alcohols:

To a microwave-flask containing 117 mg (0.263 mmol) 5-(1,3-dioxolan-2-yl)-3-iodo-1-{[2-(trimethylsilyl)ethoxy]methyl}-1H-indazole (Example 6A), 171 mg (0.525 mmol) cesium carbonate and 12 mg (0.053 mmol) 3,4,7,8-tetramethyl-1,10-phenanthroline in ethanol (1 ml) were added 5 mg (0.026 mmol) copper(I) iodide. The flask was sealed and heated to 140° C. for 2 h using microwave irradiation. After this time, the primary reaction product 5-(1,3-dioxolan-2-yl)-3-ethoxy-1-{[2-(trimethylsilyl)ethoxy]methyl}-1H-indazole could be detected by LC-MS from the crude product mixture [LC-MS (method 1): $R_t$=1.51 min; MS (ESIpos): m/z=365 (M+H)$^+$]. The reaction mixture was filtered, and the filtrate was purified by preparative RP-HPLC (acetonitrile/water+0.05% TFA gradient) to afford 55 mg (65% of th.) of the title compound.

LC-MS (method 2): $R_t$=2.75 min; MS (ESIpos): m/z=321 (M+H)$^+$ $^1$H-NMR (400 MHz, DMSO-$d_6$): δ=10.10 (s, 1H), 8.40 (s, 1H), 8.00 (d, 1H), 7.88 (d, 1H), 5.72 (s, 2H), 4.55 (q, 2H), 3.64 (t, 2H), 1.54 (t, 2H), 0.91 (t, 2H), 0.00 (s, 9H) ppm.

Example 12A

3-Ethoxy-1H-indazole-5-carbaldehyde

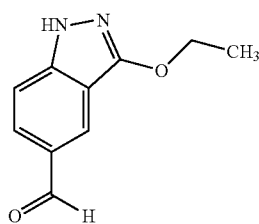

The title compound was prepared from Example 11A in analogy to the procedure described in Example 8A. The crude product thus obtained was used in the next step without further purification.

LC-MS (method 2): $R_t$=1.60 min; MS (ESIpos): m/z=191 (M+H)$^+$.

Example 13A

Tert-Butyl 5-(3,5-dicyano-2,6-dimethyl-1,4-dihydropyridin-4-yl)-3-{[(4-fluorobenzyl)sulfonyl]-amino}-1H-indazole-1-carboxylate

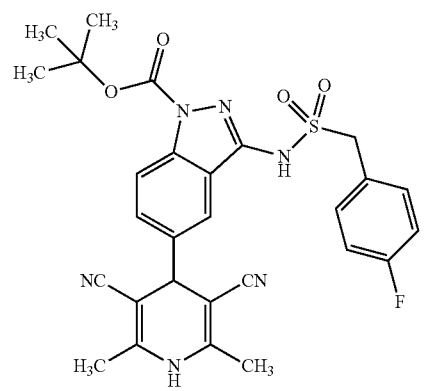 [SMILES: CC1=C(C#N)C(c2ccc3c(c2)c(NS(=O)(=O)Cc2ccc(F)cc2)nn3C(=O)OC(C)(C)C)C(C#N)=C(C)N1]

To 100 mg (0.256 mmol) tert-butyl 3-amino-5-(3,5-dicyano-2,6-dimethyl-1,4-dihydropyridin-4-yl)-1H-indazole-1-carboxylate (Example 3A) in dichloromethane (4 ml) were added 160 mg (0.77 mmol) (4-fluorophenyl)methanesulfonyl chloride and 0.11 ml (0.77 mmol) triethylamine. The mixture was stirred at reflux for 12 h. Then, further batches of 160 mg (0.77 mmol) (4-fluorophenyl)-methanesulfonyl chloride and 0.11 ml (0.77 mmol) triethylamine were added, and the mixture was again stirred at reflux for 1 h. After concentration under reduced pressure, the residue was dissolved in ethyl acetate and washed with brine. The aqueous layer was re-extracted with ethyl acetate, and the combined organic layers were washed with brine, dried over sodium sulfate, filtered, and concentrated under reduced pressure. The residue was purified by preparative RP-HPLC (acetonitrile/water gradient) to give 28 mg (19% of th.) of the title compound.

LC-MS (method 3): $R_t$=2.47 min; MS (ESIpos): m/z=563 (M+H)$^+$.

Example 14A 5-(1,3-Dioxolan-2-yl)-3-(phenylsulfonyl)-1-{[2-(trimethylsilyl)ethoxy]methyl}-1H-indazole

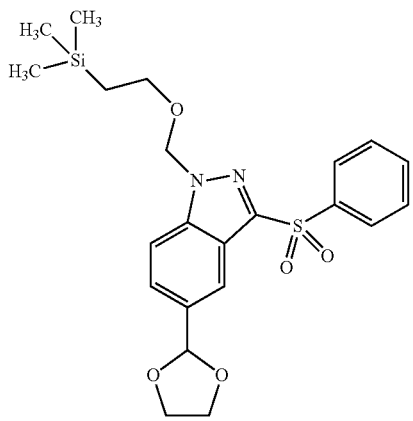 [SMILES: C[Si](C)(C)CCOCn1nc(S(=O)(=O)c2ccccc2)c2cc(C3OCCO3)ccc21]

The title compound was prepared following the procedure described for Example 9A using 150 mg (0.336 mmol) 5-(1,3-dioxolan-2-yl)-3-iodo-1-{[2-(trimethylsilyl)ethoxy]methyl}-1H-indazole (Example 6A) and 164 mg (1.01 mmol) sodium benzenesulfinate. After cooling, the reaction mixture was filtered, and the filtrate was purified by preparative RP-HPLC (acetonitrile/water+0.05% TFA gradient) to give 55 mg of a product mixture containing the title compound. This mixture was used in the next step without further purification.

LC-MS (method 2): $R_t$=2.66 min; MS (ESIpos): m/z=461 (M+H)$^+$.

Example 15A 3-(Phenylsulfonyl)-1H-indazole-5-carbaldehyde

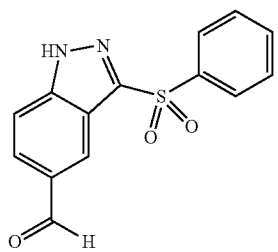 [SMILES: O=Cc1ccc2[nH]nc(S(=O)(=O)c3ccccc3)c2c1]

The title compound was prepared from Example 14A in analogy to the procedure described in Example 8A employing 6 N hydrochloric acid. The crude product (38 mg) was used in the next step without further purification.

LC-MS (method 2): $R_t$=1.77 min; MS (ESIpos): m/z=287 (M+H)$^+$.

Example 16A 3-(Cyclopropylmethoxy)-1-{[2-(trimethylsilyl)ethoxy]methyl}-1H-indazole-5-carbaldehyde

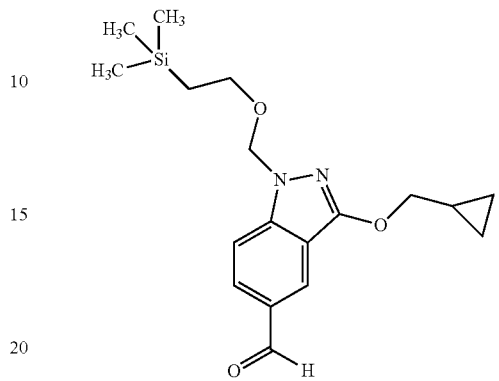

The title compound was prepared in close analogy to the procedure described in Example 11A using 166 mg (0.372 mmol) 5-(1,3-dioxolan-2-yl)-3-iodo-1-{[2-(trimethylsilyl)ethoxy]methyl}-1H-indazole (Example 6A) and 4 ml cyclopropylmethanol (instead of ethanol). The reaction mixture was filtered, and the filtrate was purified by preparative RP-HPLC (acetonitrile/water+0.05% TFA gradient) to afford 53 mg (57% of th.) of the title compound.

LC-MS (method 2): $R_t$=2.86 min; MS (ESIpos): m/z=273 [M-Si(CH$_3$)$_3$]$^+$ $^1$H-NMR (400 MHz, DMSO-d$_6$): δ=10.00 (s, 1H), 8.34 (s, 1H), 7.90 (d, 1H), 7.77 (d, 1H), 5.61 (s, 2H), 4.21 (d, 2H), 3.53 (t, 2H), 1.36 (m, 1H), 0.80 (t, 2H), 0.61 (m, 2H), 0.40 (m, 2H), –0.10 (s, 9H) ppm.

Example 17A 3-(Cyclopropylmethoxy)-1H-indazole-5-carbaldehyde

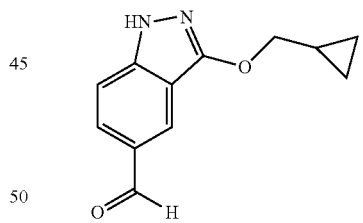

Representative procedure for 2-(trimethylsilyl)ethoxymethyl (SEM) group removal using tetrabutylammonium fluoride (TBAF):

68 mg (0.196 mmol) 3-(Cyclopropylmethoxy)-1-{[2-(trimethylsilyl)ethoxy]methyl}-1H-indazole-5-carbaldehyde (Example 16A) in THF (3 ml) were treated with 0.95 ml (0.95 mmol) of a 1 M solution of tetrabutylammonium fluoride in THF and heated to 50° C. for 5 h. After cooling, the reaction mixture was extracted with saturated aqueous sodium bicarbonate solution and ethyl acetate. The combined organic phases were washed with brine, dried over sodium sulfate, filtered and evaporated to dryness. The remaining solid was purified by preparative RP-HPLC (acetonitrile/water+0.05% TFA gradient) to afford 19 mg (44% of th.) of the title compound.

LC-MS (method 2): $R_t$=1.83 min; MS (ESIpos): m/z=217 (M+H)$^+$.

Example 18A

Tert-Butyl 3-{bis[(2-methylpropyl)sulfonyl]amino}-5-(3,5-dicyano-2,6-dimethyl-1,4-dihydropyridin-4-yl)-1H-indazole-1-carboxylate

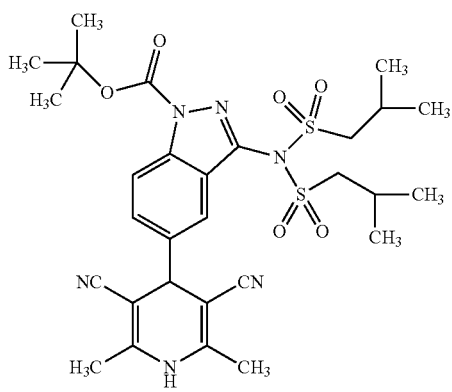 [SMILES: CC1=C(C#N)C(c2ccc3c(c2)c(N(S(=O)(=O)CC(C)C)S(=O)(=O)CC(C)C)nn3C(=O)OC(C)(C)C)C(C#N)=C(C)N1]

To 200 mg (0.512 mmol) tert-butyl 3-amino-5-(3,5-dicyano-2,6-dimethyl-1,4-dihydropyridin-4-yl)-1H-indazole-1-carboxylate (Example 3A) in dichloromethane (4 ml) were added 241 mg (1.54 mmol) 2-methylpropane-1-sulfonyl chloride and 0.21 ml (1.54 mmol) triethylamine. The mixture was stirred at room temperature for 12 h and then concentrated under reduced pressure. The residue was dissolved in ethyl acetate and washed with saturated aqueous sodium hydrogencarbonate solution. The organic layer was washed with brine, dried over sodium sulfate, filtered, and concentrated under reduced pressure. The crude product thus obtained was used for the next step without further purification.

LC-MS (method 1): $R_t$=1.47 min; MS (ESIpos): m/z=631 (M+H)$^+$.

Example 19A

Tert-Butyl 5-(3,5-dicyano-2,6-dimethyl-1,4-dihydropyridin-4-yl)-3-{[(3-ethoxy-3-oxopropyl)-sulfonyl]amino}-1H-indazole-1-carboxylate

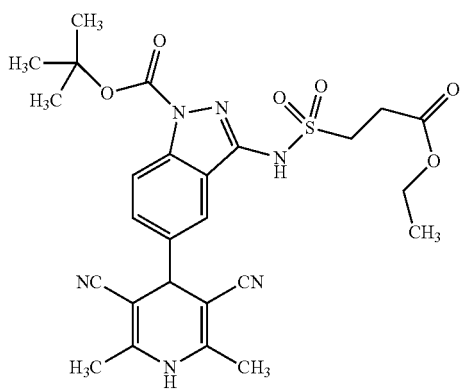 [SMILES: CCOC(=O)CCS(=O)(=O)Nc1nn(C(=O)OC(C)(C)C)c2ccc(C3C(C#N)=C(C)NC(C)=C3C#N)cc12]

To 200 mg (0.512 mmol) tert-butyl 3-amino-5-(3,5-dicyano-2,6-dimethyl-1,4-dihydropyridin-4-yl)-1H-indazole-1-carboxylate (Example 3A) in dichloromethane (4 ml) were added 309 mg (1.54 mmol) ethyl 3-(chlorosulfonyl)propanoate and 0.21 ml (1.54 mmol) triethylamine. The mixture was stirred at room temperature for 12 h and then concentrated under reduced pressure. The residue was dissolved in ethyl acetate, and the solution was washed with saturated aqueous sodium hydrogencarbonate solution, dried over sodium sulfate, filtered, and concentrated under reduced pressure. The crude product was purified by preparative RP-HPLC (acetonitrile/water gradient) to yield 41 mg (14% of th.) of the title compound.

LC-MS (method 1): $R_t$=1.19 min; MS (ESIpos): m/z=555 (M+H)$^+$ $^1$H-NMR (400 MHz, DMSO-d$_6$): δ=11.31 (s, 1H), 9.61 (s, 1H), 8.02 (d, 1H), 7.90 (s, 1H), 7.59 (d, 1H), 4.59 (s, 1H), 4.02 (q, 2H), 3.85 (t, 2H), 2.87 (t, 2H), 2.06 (s, 6H), 1.65 (s, 9H), 1.14 (t, 3H) ppm.

Example 20A

Tert-Butyl 5-(3,5-dicyano-2,6-dimethyl-1,4-dihydropyridin-4-yl)-3-[(propylsulfonyl)amino]-1H-indazole-1-carboxylate

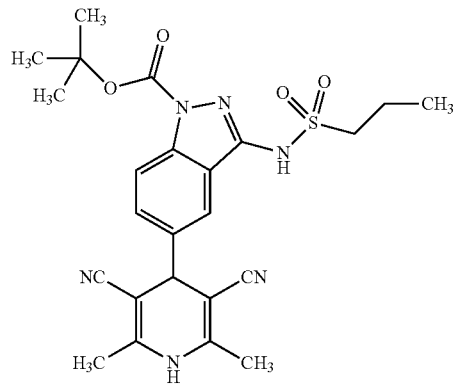 [SMILES: CCCS(=O)(=O)Nc1nn(C(=O)OC(C)(C)C)c2ccc(C3C(C#N)=C(C)NC(C)=C3C#N)cc12]

To 200 mg (0.512 mmol) tert-butyl 3-amino-5-(3,5-dicyano-2,6-dimethyl-1,4-dihydropyridin-4-yl)-1H-indazole-1-carboxylate (Example 3A) in dichloromethane (4 ml) were added 219 mg (1.54 mmol) propane-1-sulfonyl chloride and 0.21 ml (1.54 mmol) triethylamine. The mixture was stirred at room temperature for 12 h and then concentrated under reduced pressure. The residue was dissolved in ethyl acetate and washed with saturated aqueous sodium hydrogencarbonate solution. The organic layer was washed with brine, dried over sodium sulfate, filtered, and concentrated under reduced pressure. The crude product was purified by preparative RP-HPLC (acetonitrile/water gradient) to give 28 mg (11% of th.) of the title compound.

LC-MS (method 3): $R_t$=2.31 min; MS (ESIpos): m/z=497 (M+H)$^+$.

Example 21A 5-(1,3-Dioxolan-2-yl)-3-methoxy-1-{[2-(trimethylsilyl)ethoxy]methyl}-1H-indazole

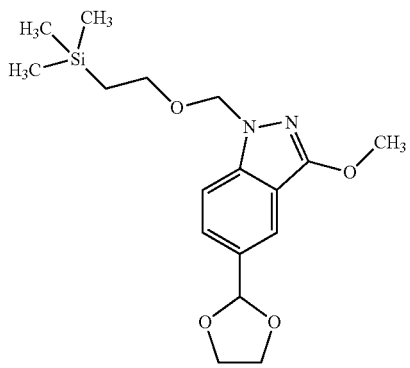

To a microwave-flask containing 300 mg (0.672 mmol) 5-(1,3-dioxolan-2-yl)-3-iodo-1-{[2-(trimethylsilyl)ethoxy]methyl}-1H-indazole (Example 6A), 438 mg (1.344 mmol) cesium carbonate and 32 mg (0.134 mmol) 3,4,7,8-tetramethyl-1,10-phenanthroline in methanol (4 ml) were added 13 mg (0.067 mmol) copper(I) iodide. The flask was placed in an ultrasonic bath, and argon was bubbled through for a period of five minutes. The flask was then sealed and heated to 140° C. for 2 h using microwave irradiation. The reaction mixture was filtered over celite which was washed with acetonitrile. The filtrates of a total of seven reactions at this scale were combined and purified by preparative RP-HPLC (acetonitrile/water gradient) to afford 940 mg (57% of th.) of the title compound.

LC-MS (method 2): =2.53 min; MS (ESIpos): m/z=351 (M+H)$^+$ $^1$H-NMR (400 MHz, DMSO-d$_6$): δ=7.77 (br. s, 1H), 7.73 (d, 1H), 7.59 (dd, 1H), 5.91 (s, 1H), 5.67 (s, 2H), 4.20-4.17 (m, 2H), 4.11 (s, 3H), 4.07-4.04 (m, 2H), 3.61 (t, 2H), 0.89 (t, 2H), 0.01 (s, 9H) ppm.

Example 22A

3-Methoxy-1H-indazole-5-carbaldehyde

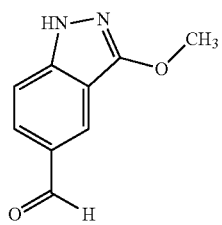

Representative procedure for 2-(trimethylsilyl)ethoxymethyl (SEM) group removal using fluoride anion:

To 940 mg (2.682 mmol) 5-(1,3-dioxolan-2-yl)-3-methoxy-1-{[2-(trimethylsilyl)ethoxy]methyl}-1H-indazole (Example 21A) and 805 mg (13.41 mmol) ethane-1,2-diamine in THF (50 ml) were added 12.98 ml (12.98 mmol) tetrabutylammonium fluoride solution (1.0 M in THF). The reaction mixture was heated to 50° C. for 3 h. After this time, 12.98 ml (12.98 mmol) tetrabutylammonium fluoride solution (1.0 M in THF) were added again, and heating was continued for further 12 h until conversion was complete. The mixture was partitioned between ethyl acetate and saturated aqueous sodium bicarbonate solution. The layers were separated, and the aqueous layer was washed twice with ethyl acetate. The combined organic layers were washed with brine and dried over sodium sulfate. After filtration, the solvent was evaporated, and the remaining solid was purified by chromatography on silica gel (cyclohexane/ethyl acetate gradient) to afford 556 mg (94% of th.) of the intermediate compound 5-(1,3-dioxolan-2-yl)-3-methoxy-1H-indazole [LC-MS (method 2): R$_t$=1.44 min; MS (ESIpos): m/z=211 (M+H)$^+$]. This material was dissolved in ethanol (37 ml), treated with 1 N hydrochloric acid (9.4 ml) and heated to 90° C. for 30 minutes. After this time, the mixture was evaporated to dryness, and the crude aldehyde thus obtained was used in the next step without further purification.

LC-MS (method 2): R$_t$=1.40 min; MS (ESIpos): m/z=177 (M+H)$^+$.

Example 23A 5-(1,3-Dioxolan-2-yl)-3-isopropoxy-1-{[2-(trimethylsilyl)ethoxy]methyl}-1H-indazole

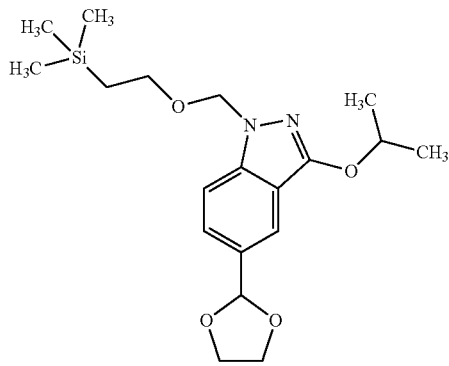 [SMILES: CC(C)Oc1nn(COCC[Si](C)(C)C)c2ccc(C3OCCO3)cc12]

The title compound was prepared from 300 mg (0.672 mmol) 5-(1,3-dioxolan-2-yl)-3-iodo-1-{[2-(trimethylsilyl)ethoxy]methyl}-1H-indazole (Example 6A) in analogy to the procedure described in Example 21A. The crude product was purified by preparative RP-HPLC (acetonitrile/water gradient) to afford 124 mg (48% of th.) of the title compound.

LC-MS (method 2): R$_t$=2.80 min; MS (ESIpos): m/z=379 (M+H)$^+$.

Example 24A

3-Isopropoxy-1H-indazole-5-carbaldehyde

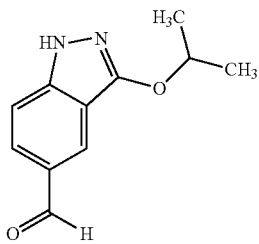

The title compound was prepared from Example 23A in close analogy to the procedure described in Example 22A.

LC-MS (method 2): $R_t$=1.74 min; MS (ESIpos): m/z=205 (M+H)$^+$.

Example 25A 5-(1,3-Dioxolan-2-yl)-3-isobutoxy-1-{[2-(trimethylsilyl)ethoxy]methyl}-1H-indazole

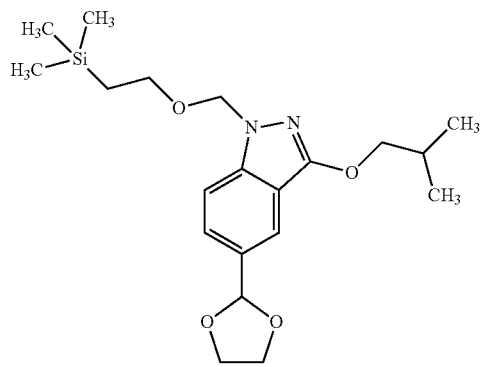 [SMILES: CC(C)COc1nn(COCC[Si](C)(C)C)c2ccc(C3OCCO3)cc12]

The title compound was prepared from 300 mg (0.672 mmol) 5-(1,3-dioxolan-2-yl)-3-iodo-1-{[2-(trimethylsilyl)ethoxy]methyl}-1H-indazole (Example 6A) in analogy to the procedure described in Example 21A. The crude product was purified by preparative RP-HPLC (acetonitrile/water gradient) to afford 129 mg (48% of th.) of the title compound.

Example 26A

3-Isobutoxy-1H-indazole-5-carbaldehyde

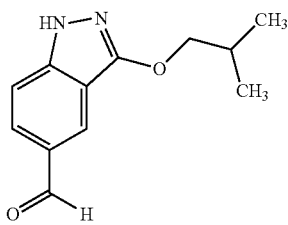 [SMILES: CC(C)COc1n[nH]c2ccc(C=O)cc12]

The title compound was prepared from Example 25A in close analogy to the procedure described in Example 22A.

Example 27A 3-(Cyclobutylmethoxy)-5-(1,3-dioxolan-2-yl)-1-{[2-(trimethylsilyl)ethoxy]methyl}-1H-indazole

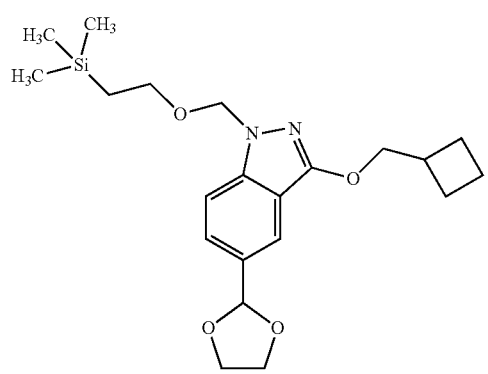 [SMILES: C[Si](C)(C)CCOCn1nc(OCC2CCC2)c2cc(C3OCCO3)ccc21]

The title compound was prepared from 300 mg (0.672 mmol) 5-(1,3-dioxolan-2-yl)-3-iodo-1-{[2-(trimethylsilyl)ethoxy]methyl}-1H-indazole (Example 6A) in analogy to the procedure described in Example 21A. The crude product was purified by preparative RP-HPLC (acetonitrile/water gradient) to afford 146 mg (53% of th.) of the title compound.

Example 28A 3-(Cyclobutylmethoxy)-1H-indazole-5-carbaldehyde

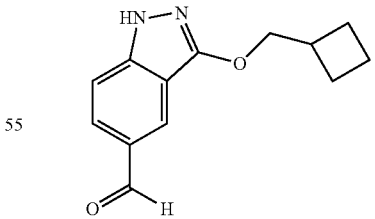

The title compound was prepared from Example 27A in close analogy to the procedure described in Example 22A.

LC-MS (method 2): $R_t$=2.04 min; MS (ESIpos): m/z=231 (M+H)$^+$.

Example 29A 5-(1,3-Dioxolan-2-yl)-3-propoxy-1-{[2-(trimethylsilyl)ethoxy]methyl}-1H-indazole

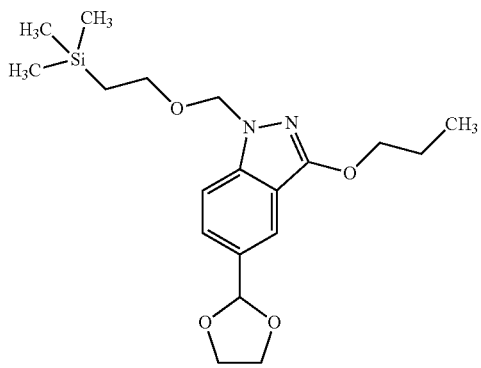 [SMILES: CCCOc1nn(COCC[Si](C)(C)C)c2ccc(C3OCCO3)cc12]

The title compound was prepared from 300 mg (0.672 mmol) 5-(1,3-dioxolan-2-yl)-3-iodo-1-{[2-(trimethylsilyl)ethoxy]methyl}-1H-indazole (Example 6A) in analogy to the procedure described in Example 21A. The crude product was purified by preparative RP-HPLC (acetonitrile/water gradient) to afford 139 mg (54% of th.) of the title compound.

Example 30A

3-Propoxy-1H-indazole-5-carbaldehyde

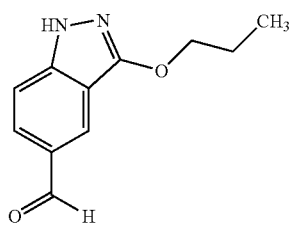

The title compound was prepared from Example 29A in close analogy to the procedure described in Example 22A.

LC-MS (method 2): $R_t$=1.79 min; MS (ESIpos): m/z=205 (M+H)$^+$.

Example 31A 5-(1,3-Dioxolan-2-yl)-3-(2-isopropoxyethoxy)-1-{[2-(trimethylsilyl)ethoxy]methyl}-1H-indazole

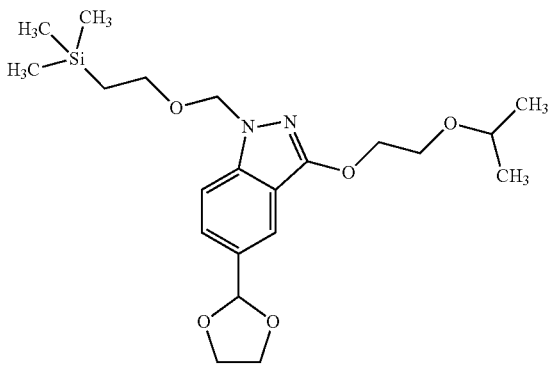 [SMILES: CC(C)OCCOc1nn(COCC[Si](C)(C)C)c2ccc(C3OCCO3)cc12]

The title compound was prepared from 6.00 g (13.44 mmol) 5-(1,3-dioxolan-2-yl)-3-iodo-1-{[2-(trimethylsilyl)ethoxy]methyl}-1H-indazole (Example 6A) in analogy to the procedure described in Example 21A. The crude product was purified by preparative RP-HPLC (acetonitrile/water gradient) to afford 2.33 g (41% of th.) of the title compound.

Example 32A 3-(2-Isopropoxyethoxy)-1H-indazole-5-carbaldehyde

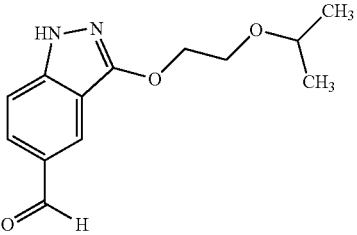 [SMILES: CC(C)OCCOc1n[nH]c2ccc(C=O)cc12]

The title compound was prepared from Example 31A in close analogy to the procedure described in Example 22A.

Example 33A 5-(1,3-Dioxolan-2-yl)-3-[2-(morpholin-4-yl)ethoxy]-1-{[2-(trimethylsilyl)ethoxy]methyl}-1H-indazole

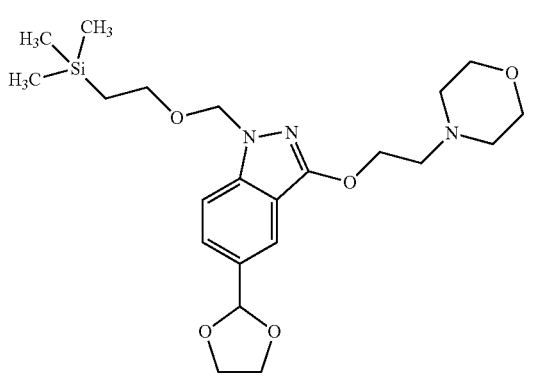 [SMILES: C[Si](C)(C)CCOCn1nc(OCCN2CCOCC2)c2cc(C3OCCO3)ccc21]

The title compound was prepared from 300 mg (0.672 mmol) 5-(1,3-dioxolan-2-yl)-3-iodo-1-{[2-(trimethylsilyl)ethoxy]methyl}-1H-indazole (Example 6A) in analogy to the procedure described in Example 21A. The procedure was modified by using 5 equivalents of 2-(morpholin-4-yl)ethanol as the alcohol reactant and by switching to toluene as solvent. After treating the mixture in a microwave oven at 140° C. for 2 h, the same amounts of catalyst and ligand were added again, and the mixture was refluxed for further 7 days using conventional heating. The crude product was purified by preparative RP-HPLC (acetonitrile/water gradient) to afford 93 mg (30% of th.) of the title compound.

LC-MS (method 2): $R_t$=1.74 min; MS (ESIpos): m/z=450 $(M+H)^+$.

Example 35A 5-(1,3-Dioxolan-2-yl)-3-[2-(piperidin-1-yl)ethoxy]-1-{[2-(trimethylsilyl)ethoxy]methyl}-1H-indazole

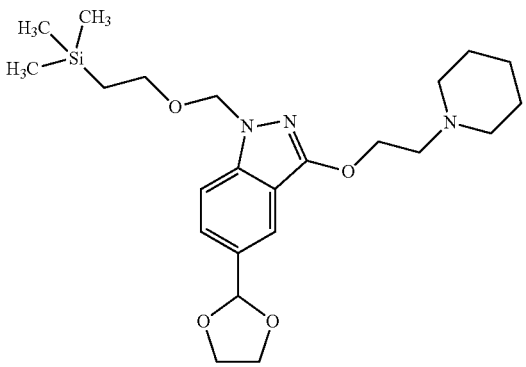

The title compound was prepared from 600 mg (1.344 mmol) 5-(1,3-dioxolan-2-yl)-3-iodo-1-{[2-(trimethylsilyl)ethoxy]methyl}-1H-indazole (Example 6A) in analogy to the procedure described in Example 21A. The procedure was modified by using 5 equivalents of 2-(piperidin-1-yl)ethanol as the alcohol reactant and by switching to toluene as solvent. Instead of using microwave irradiation, the reaction mixture was refluxed for 5 days employing conventional heating. During this time, the same amounts of catalyst and ligand were added again on day 3. The crude product thus obtained was purified by chromatography on silica gel (cyclohexane/ethyl acetate gradient) to afford 244 mg (32% of th.) of the title compound.

LC-MS (method 2): $R_t$=1.85 min; MS (ESIpos): m/z=448 $(M+H)^+$.

Example 34A

3-[2-(Morpholin-4-yl)ethoxy]-1H-indazole-5-carbaldehyde

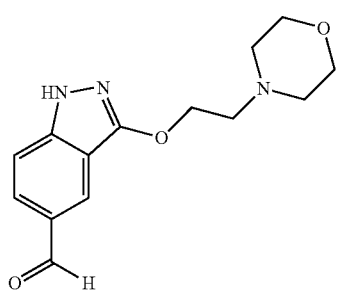 [SMILES: O=Cc1ccc2[nH]nc(OCCN3CCOCC3)c2c1]

The title compound was prepared from Example 33A in close analogy to the procedure described in Example 22A.

LC-MS (method 2): $R_t$=0.94 min; MS (ESIpos): m/z=276 $(M+H)^+$.

Example 36A

3-[2-(Piperidin-1-yl)ethoxy]-1H-indazole-5-carbaldehyde

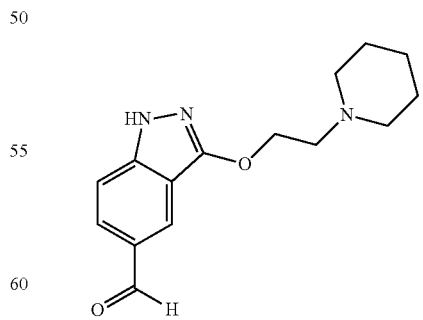

The title compound was prepared from Example 35A in close analogy to the procedure described in Example 22A.

LC-MS (method 2): $R_t$=1.05 min; MS (ESIpos): m/z=274 $(M+H)^+$.

Example 37A 5-(1,3-Dioxolan-2-yl)-3-[2-(1H-pyrazol-1-yl)ethoxy]-1-{[2-(trimethylsilyl)ethoxy]methyl}-1H-indazole

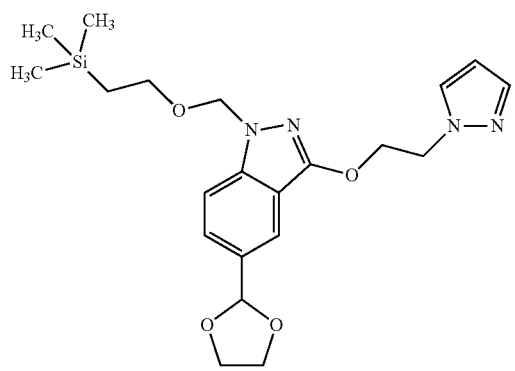 [SMILES: C[Si](C)(C)CCOCn1nc(OCCn2cccn2)c2cc(C3OCCO3)ccc21]

The title compound was prepared from 300 mg (0.672 mmol) 5-(1,3-dioxolan-2-yl)-3-iodo-1-([2-(trimethylsilyl)ethoxy]methyl)-1H-indazole (Example 6A) in analogy to the procedure described in Example 21A. The procedure was modified by using 5 equivalents of 2-(1H-pyrazol-1-yl)-ethanol as the alcohol reactant and by switching to toluene as solvent. The reaction mixture was heated to 140° C. for 2 h using microwave irradiation, after which time the same amounts of catalyst and ligand were added again. This cycle was repeated one more time. The crude product thus obtained was purified by preparative RP-HPLC (acetonitrile/water gradient) to afford 153 mg (52% of th.) of the title compound.

Example 38A

3-[2-(1H-Pyrazol-1-yl)ethoxy]-1H-indazole-5-carbaldehyde

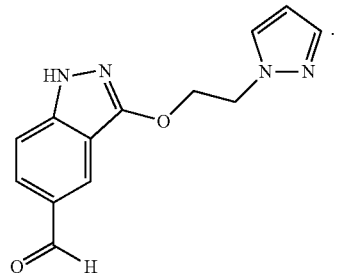 [SMILES: O=Cc1ccc2[nH]nc(OCCn3cccn3)c2c1]

The title compound was prepared from Example 37A in close analogy to the procedure described in Example 22A.

LC-MS (method 2): $R_t$=1.52 min; MS (ESIpos): m/z=257 (M+H)$^+$.

Example 39A 3-(3,5-Difluorophenoxy)-5-(1,3-dioxolan-2-yl)-1-{[2-(trimethylsilyl)ethoxy]methyl}-1H-indazole

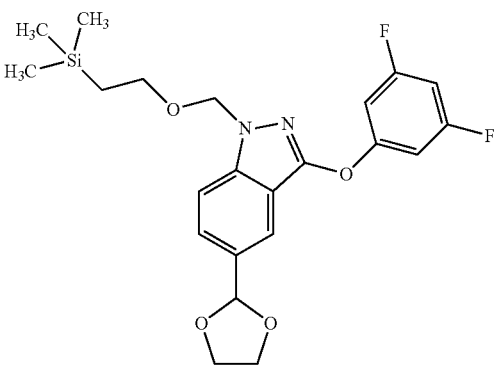 [SMILES: C[Si](C)(C)CCOCn1nc(Oc2cc(F)cc(F)c2)c2cc(C3OCCO3)ccc21]

To a microwave-flask containing 300 mg (0.672 mmol) 5-(1,3-dioxolan-2-yl)-3-iodo-1-{[2-(trimethylsilyl)ethoxy]methyl}-1H-indazole (Example 6A), 438 mg (1.344 mmol) cesium carbonate and 19 mg (0.134 mmol) N,N-dimethylglycine hydrochloride in 1,4-dioxane (3 ml) were added 131 mg (1.008 mmol) 3,5-difluorophenol and 13 mg (0.067 mmol) copper(I) iodide. The flask was placed in an ultrasonic bath, and argon was bubbled through for a period of five minutes. The flask was then sealed and heated to 140° C. for 2 h using microwave irradiation. After this time, the same amounts of N,N-dimethylglycine hydrochloride and copper (I) iodide were added again, and heating was continued for further 2 h. This procedure was repeated one more time. Then, the reaction mixture was filtered, and the filtrate was purified by preparative RP-HPLC (acetonitrile/water+0.05% TFA gradient) to afford 43 mg (14% of th.) of the title compound.

Example 40A 3-(3,5-Difluorophenoxy)-1H-indazole-5-carbaldehyde

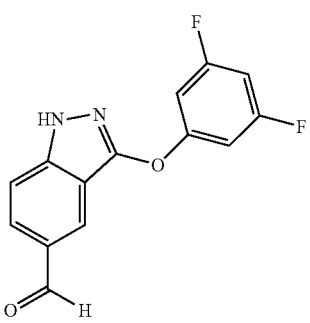 [SMILES: O=Cc1ccc2[nH]nc(Oc3cc(F)cc(F)c3)c2c1]

The title compound was prepared from Example 39A in close analogy to the procedure described in Example 22A.

LC-MS (method 2): $R_t$=2.11 min; MS (ESIpos): m/z=275 (M+H)$^+$.

Example 41A

4-{[5-(1,3-Dioxolan-2-yl)-1-{[2-(trimethylsilyl)ethoxy]methyl}-1H-indazol-3-yl]sulfanyl}-N,N-diethylaniline

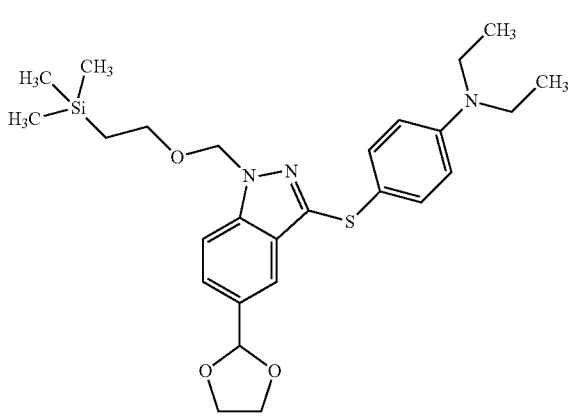 [SMILES: CCN(CC)c1ccc(Sc2nn(COCC[Si](C)(C)C)c3ccc(C4OCCO4)cc23)cc1]

The title compound was prepared from 1.00 g (2.24 mmol) 5-(1,3-dioxolan-2-yl)-3-iodo-1-{[2-(trimethylsilyl)ethoxy]methyl}-1H-indazole (Example 6A) in analogy to the procedure described in Example 7A. The crude product was purified by silica gel chromatography (cyclohexane/ethyl acetate gradient) to afford 1.08 g (96% of th.) of the title compound.

LC-MS (method 2): $R_t$=2.81 min; MS (ESIpos): m/z=500 (M+H)$^+$.

Example 42A

3-{[4-(Diethylamino)phenyl]sulfanyl}-1H-indazole-5-carbaldehyde

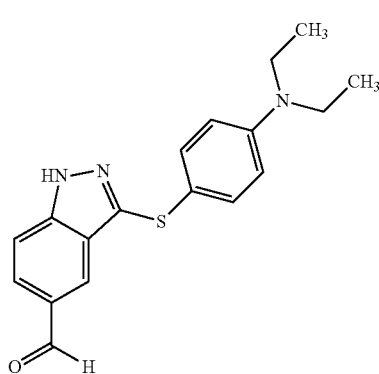 [SMILES: CCN(CC)c1ccc(Sc2n[nH]c3ccc(C=O)cc23)cc1]

The title compound was prepared from Example 41A in analogy to the procedure described in Example 8A. The crude product thus obtained was used in the next step without further purification.

Example 43A

3-Chloro-1H-indazole-5-carbaldehyde

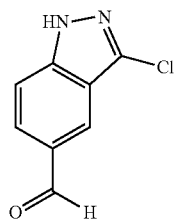 [SMILES: O=Cc1ccc2[nH]nc(Cl)c2c1]

To a solution of 4.0 g (27.4 mmol) 1H-indazole-5-carbaldehyde [preparation described in US 2005/0227968-A1 (Intermediate 1)] in acetonitrile (116 ml) were added 4.2 g (31.5 mmol) N-chlorosuccinimide at room temperature. The resulting solution was stirred under reflux for 12 h. The mixture was then concentrated under reduced pressure yielding a solid precipitate. This material was triturated with water, filtered, and dried under high vacuum for 12 h to give the title compound (4.8 g, 97% of th.) as a white solid.

$^1$H-NMR (400 MHz, DMSO-d$_6$): δ=13.76 (s, 1H), 10.06 (s, 1H), 8.37 (s, 1H), 7.92 (d, 1H), 7.72 (d, 1H) ppm.

Example 44A

3-Chloro-5-(1,3-dioxan-2-yl)-1H-indazole

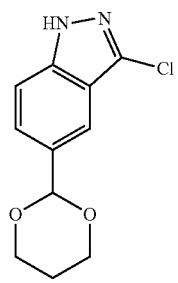 [SMILES: Clc1n[nH]c2ccc(C3OCCCO3)cc12]

2.2 g (12.2 mmol) 3-chloro-1H-indazole-5-carbaldehyde (Example 43A), 4.64 g (60.9 mmol) propane-1,3-diol and a trace amount of p-toluene sulfonic acid in toluene (60 ml) were heated to reflux for 12 h using a Dean-Stark trap. After cooling, the mixture was concentrated under reduced pressure. The residue was dissolved in ethyl acetate and washed with water. The organic layer was dried with sodium sulfate, filtered and evaporated to dryness. The remaining solid (2.76 g, 91% of th.) was used in the next step without further purification.

LC-MS (method 4): $R_t$=1.45 min; MS (ESIpos): m/z=239 (M+H)$^+$ $^1$H-NMR (400 MHz, DMSO-d$_6$): δ=13.32 (s, 1H), 7.66 (s, 1H), 7.58-7.46 (m, 2H), 5.64 (s, 1H), 4.16 (m, 2H), 3.97 (m, 2H), 2.02 (m, 1H), 1.47 (m, 1H) ppm.

Example 45A

3-Chloro-5-(1,3-dioxan-2-yl)-1-{[2-(trimethylsilyl)ethoxy]methyl}-1H-indazole

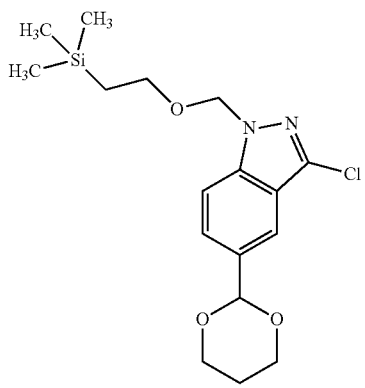 [SMILES: C[Si](C)(C)CCOCn1nc(Cl)c2cc(C3OCCCO3)ccc21]

To a solution of 2.7 g (11.3 mmol) 3-chloro-5-(1,3-dioxan-2-yl)-1H-indazole (Example 44A) in anhydrous THF (60 ml) were added 1.31 g (13.6 mmol) sodium tert-butoxide at room temperature. The solution was cooled to 0° C., and 2.26 g (13.6 mmol) 2-(trimethylsilyl)ethoxymethyl chloride were added at this temperature. The resulting mixture was stirred at 0° C. for 1 h and then concentrated under reduced pressure. The residue was dissolved in ethyl acetate and washed with water and with brine. The organic layer was dried with sodium sulfate, filtered and evaporated to dryness. The residue was purified by flash chromatography (silica gel; cyclohexane/ethyl acetate 5:1 v/v) to give 1.73 g (41% of th.) of the title compound.

LC-MS (method 1): $R_t$=1.56 min; MS (ESIpos): m/z=369 (M+H)$^+$ $^1$H-NMR (400 MHz, DMSO-d$_6$): δ=7.80 (d, 1H), 7.70 (s, 1H), 7.59 (dd, 1H), 5.72 (s, 2H), 5.66 (s, 1H), 4.17 (m, 2H), 3.97 (m, 2H), 3.52 (t, 2H), 2.02 (m, 1H), 1.47 (m, 1H), 0.79 (t, 2H), 0.1 (s, 9H) ppm.

Example 46A 5-(1,3-Dioxan-2-yl)-N-(2-methoxyethyl)-N-methyl-1-{[2-(trimethylsilyl)ethoxy]methyl}-1H-indazol-3-amine

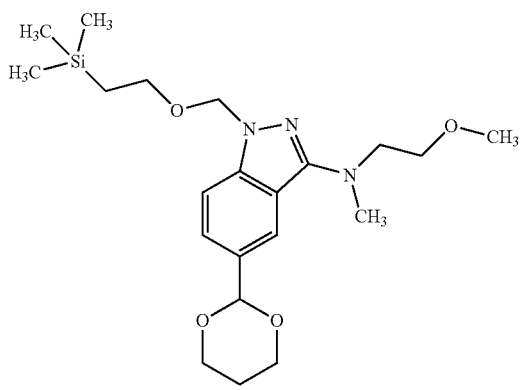

To a degassed solution of 400 mg (1.08 mmol) 3-chloro-5-(1,3-dioxan-2-yl)-1-{[2-(trimethylsilyl)-ethoxy]methyl}-1H-indazole (Example 45A) and 135 mg (1.52 mmol) 2-methoxy-N-methylethanamine in anhydrous THF (11 ml) were added under inert gas atmosphere 103 mg (0.22 mmol) 2-(dicyclohexylphosphino)-2',4',6'-triisopropyl-1,1'-biphenyl (XPhos), 50 mg (0.054 mmol) tris(di-benzylideneacetone)dipalladium(0) (Pd$_2$dba$_3$) and 5.42 ml (5.42 mmol) lithium hexamethyldisilazide solution (1 M in THF). The resulting mixture was stirred under reflux for 12 h. After cooling to room temperature and concentration under reduced pressure, the remaining solid was dissolved in ethyl acetate (20 ml). The solution was washed with water and with brine, dried over sodium sulfate and concentrated under reduced pressure. The crude product was purified by preparative RP-HPLC (acetonitrile/water gradient, final mixture 90:10 v/v) to yield the title compound as a white solid (246 mg, 42% of th.).

LC-MS (method 1): $R_t$=1.47 min; MS (ESIpos): m/z=422 (M+H)$^+$.

Example 47A 5-(1,3-Dioxan-2-yl)-N-(2-methoxyethyl)-N-methyl-1H-indazol-3-amine

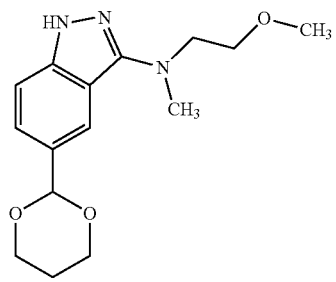 [SMILES: COCCN(C)c1n[nH]c2ccc(C3OCCCO3)cc12]

To a solution of 245 mg (0.583 mmol) 5-(1,3-dioxan-2-yl)-N-(2-methoxyethyl)-N-methyl-1-{[2-(trimethylsilyl)ethoxy]methyl}-1H-indazol-3-amine (Example 46A) in anhydrous THF (12 ml) were added 8.5 ml (8.5 mmol) tetrabutylammonium fluoride solution (1 M in THF) and ethane-1,2-diamine (200 μl). The solution was stirred at 50° C. for 3 h. After addition of further 8.5 ml tetrabutylammonium fluoride solution (1 M in THF), stirring at 50° C. was continued for 24 h. After cooling, the mixture was concentrated under reduced pressure. The residue was dissolved in ethyl acetate and washed with saturated aqueous sodium hydrogencarbonate solution and with water. The organic layer was dried with sodium sulfate, filtered and evaporated to dryness. The remaining solid (200 mg, 87% of th.) was used in the next step without further purification.

LC-MS (method 1): $R_t$=0.83 min; MS (ESIpos): m/z=292 (M+H)$^+$.

Example 48A

3-[(2-Methoxyethyl)(methyl)amino]-1H-indazole-5-carbaldehyde

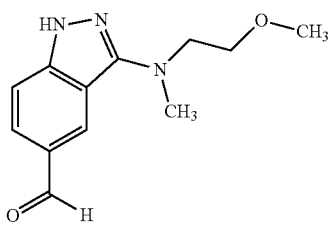 [SMILES: COCCN(C)c1n[nH]c2ccc(C=O)cc12]

To a solution of 170 mg (0.583 mmol) 5-(1,3-dioxan-2-yl)-N-(2-methoxyethyl)-N-methyl-1H-indazol-3-amine (Example 47A) in ethanol (10 ml) were added 1.9 ml (5.83 mmol) 3 M hydrochloric acid, and the solution was heated to 90° C. for 30 min. After cooling, the mixture was concentrated under reduced pressure. The remaining material (135 mg, 99% of th.) was used in the next step without further purification.

LC-MS (method 5): $R_t$=0.71 min; MS (ESIpos): m/z=234 (M+H)$^+$.

Example 49A 5-(1,3-Dioxan-2-yl)-N-(3-methoxypropyl)-N-methyl-1-{[2-(trimethylsilyl)ethoxy]methyl}-1H-indazol-3-amine

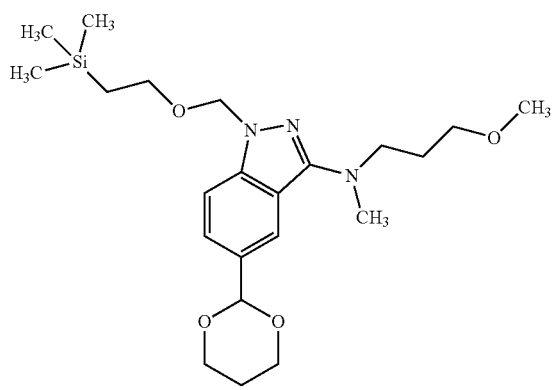

To a degassed solution of 400 mg (1.08 mmol) 3-chloro-5-(1,3-dioxan-2-yl)-1-{[2-(trimethylsilyl)-ethoxy]methyl}-1H-indazole (Example 45A) and 135 mg (1.52 mmol) 3-methoxy-N-methyl-propanamine in anhydrous THF (11 ml) were added under inert gas atmosphere 103 mg (0.22 mmol) 2-(dicyclohexylphosphino)-2',4',6'-triisopropyl-1,1'-biphenyl (XPhos), 50 mg (0.054 mmol) tris(dibenzylideneacetone)dipalladium(0) (Pd$_2$dba$_3$) and 5.42 ml (5.42 mmol) lithium hexamethyldisilazide solution (1 M in THF). The resulting mixture was stirred under reflux for 12 h. After cooling to room temperature and concentration under reduced pressure, the remaining solid was dissolved in ethyl acetate (20 ml). The solution was washed with water and with brine, dried over sodium sulfate and concentrated under reduced pressure. The crude product was purified by preparative RP-HPLC (acetonitrile/water gradient, final mixture 90:10 v/v) to yield the title compound as a white solid (187 mg, 24% of th.).

LC-MS (method 5): $R_t$=1.35 min; MS (ESIpos): m/z=436 (M+H)$^+$.

Example 50A 5-(1,3-Dioxan-2-yl)-N-(3-methoxypropyl)-N-methyl-1H-indazol-3-amine

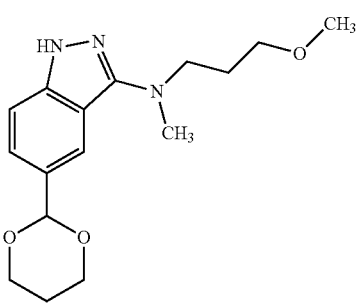 [SMILES: COCCCN(C)c1n[nH]c2ccc(C3OCCCO3)cc12]

To a solution of 187 mg (0.429 mmol) 5-(1,3-dioxan-2-yl)-N-(3-methoxypropyl)-N-methyl-1-{[2-(trimethylsilyl)ethoxy]methyl}-1H-indazol-3-amine (Example 49A) in anhydrous THF (12 ml) were added 6.2 ml (6.2 mmol) tetrabutylammonium fluoride solution (1 M in THF) and ethane-1,2-diamine (145 µl). The solution was stirred at 50° C. for 3 h. After addition of further 6.2 ml tetrabutylammonium fluoride solution (1 M in THF), stirring at 50° C. was continued for 24 h. After cooling, the mixture was concentrated under reduced pressure. The residue was dissolved in ethyl acetate and washed with saturated aqueous sodium hydrogencarbonate solution and with water. The organic layer was dried with sodium sulfate, filtered and evaporated to dryness. The remaining solid (131 mg, 99% of th.) was used in the next step without further purification.

LC-MS (method 1): $R_t$=0.88 min; MS (ESIpos): m/z=306 (M+H)$^+$.

Example 51A

3-[(3-Methoxypropyl)(methyl)amino]-1H-indazole-5-carbaldehyde

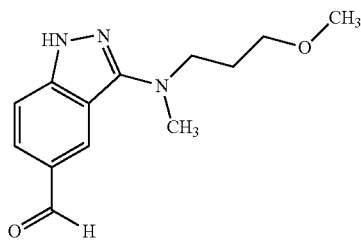 [SMILES: COCCCN(C)c1n[nH]c2ccc(C=O)cc12]

To a solution of 131 mg (0.429 mmol) 5-(1,3-dioxan-2-yl)-N-(3-methoxypropyl)-N-methyl-1H-indazol-3-amine (Example 50A) in ethanol (7.0 ml) were added 1.43 ml (4.29 mmol) 3 M hydrochloric acid, and the solution was heated to 90° C. for 30 min. After cooling, the mixture was concen-

Preparation Examples

Example 1

N-[5-(3,5-Dicyano-2,6-dimethyl-1,4-dihydropyridin-4-yl)-1H-indazol-3-yl]-2-methoxyethane-sulfonamide

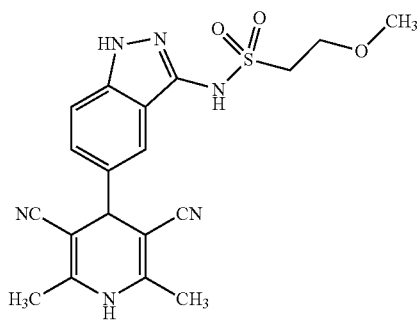

To 100 mg (0.256 mmol) tert-butyl 3-amino-5-(3,5-dicyano-2,6-dimethyl-1,4-dihydropyridin-4-yl)-1H-indazole-1-carboxylate (Example 3A) in dichloromethane (4 ml) were added 123 mg (0.77 mmol) 2-methoxyethanesulfonyl chloride and 0.11 ml (0.77 mmol) triethylamine. The mixture was stirred at room temperature for 12 h and then concentrated under reduced pressure. The residue was dissolved in ethyl acetate and washed with brine. The aqueous layer was re-extracted with ethyl acetate, and the combined organic layers were washed with brine, dried over sodium sulfate, filtered, and concentrated under reduced pressure. The residue was dissolved in dichloromethane (4 ml), and to the solution were added 0.175 ml (2.27 mmol) trifluoroacetic acid. The mixture was stirred at room temperature for 2 h and then concentrated under reduced pressure. The residue was dissolved in ethyl acetate and washed with saturated aqueous sodium bicarbonate solution. The organic layer was separated, dried over sodium sulfate, filtered, and concentrated under reduced pressure. The residue was purified by preparative RP-HPLC (acetonitrile/water gradient) to give 32 mg (30% of th.) of the title compound.

LC-MS (method 1): $R_t$=0.82 min; MS (ESIpos): m/z=413 (M+H)$^+$ $^1$H-NMR (400 MHz, DMSO-d$_6$): δ=12.84 (s, 1H), 10.4 (s, 1H), 9.55 (s, 1H), 7.63 (s, 1H), 7.50 (d, 1H), 7.32 (d, 1H), 4.51 (s, 1H), 3.84 (t, 1H), 3.61 (t, 2H), 3.32 (s, 3H), 2.05 (s, 6H) ppm.

Example 2

4-[3-(Benzylsulfanyl)-1H-indazol-5-yl]-2,6-dimethyl-1,4-dihydropyridine-3,5-dicarbonitrile

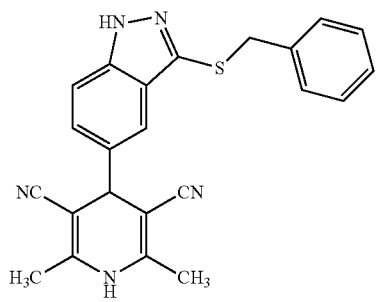 [SMILES: CC1=C(C#N)C(c2ccc3[nH]nc(SCc4ccccc4)c3c2)C(C#N)=C(C)N1]

Representative procedure for the Hantzsch reaction of indazol-5-yl carbaldehydes with 3-aminobut-2-enenitrile (formation of 2,6-dimethyl-1,4-dihydropyridine-3,5-dicarbonitriles):

The crude product obtained in Example 8A and 29.6 mg (0.361 mmol) 3-aminobut-2-enenitrile in acetic acid (4 ml) were heated to 110° C. for 1 h. After cooling, the reaction mixture was directly purified by preparative RP-HPLC (acetonitrile/water+0.05% TFA gradient) yielding 30 mg (46% of th.) of the title compound.

LC-MS (method 2): $R_t$=2.08 min; MS (ESIpos): m/z=398 (M+H)$^+$.

$^1$H-NMR (400 MHz, DMSO-d$_6$): δ=13.22 (br. s, 1H), 9.52 (s, 1H), 7.55 (d, 1H), 7.41 (br. s, 1H), 7.33-7.30 (m, 3H), 7.27-7.20 (m, 3H), 4.54 (s, 1H), 4.30 (s, 2H), 2.04 (s, 6H) ppm.

Example 3

2,6-Dimethyl-4-[3-(methylsulfonyl)-1H-indazol-5-yl]-1,4-dihydropyridine-3,5-dicarbonitrile

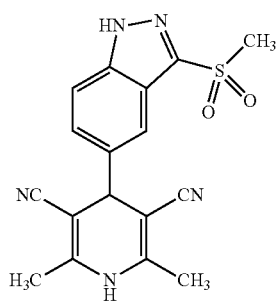 [SMILES: CC1=C(C#N)C(c2ccc3[nH]nc(S(C)(=O)=O)c3c2)C(C#N)=C(C)N1]

The title compound was prepared from Example 10A in analogy to the procedure described in Example 2 yielding 31 mg (60% of th.) after purification by RP-HPLC (acetonitrile/water+0.05% TFA gradient).

LC-MS (method 2): $R_t$=1.55 min; MS (ESIpos): m/z=354 (M+H)+

$^1$H-NMR (400 MHz, DMSO-d$_6$): δ=14.28 (s, 1H), 9.58 (s, 1H), 7.83 (s, 1H), 7.78 (d, 1H), 7.49 (dd, 1H), 4.66 (s, 1H), 3.37 (s, 3H), 2.05 (s, 6H) ppm.

Example 4

4-(3-Ethoxy-1H-indazol-5-yl)-2,6-dimethyl-1,4-dihydropyridine-3,5-dicarbonitrile

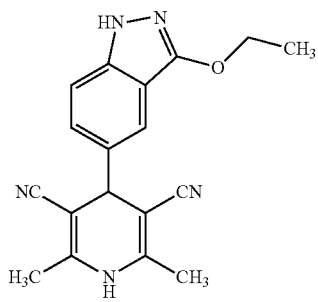 [SMILES: CCOc1n[nH]c2ccc(C3C(C#N)=C(C)NC(C)=C3C#N)cc12]

The title compound was prepared from Example 12A in analogy to the procedure described in Example 2 yielding 36 mg (65% of th.) after purification by RP-HPLC (acetonitrile/water+0.05% TFA gradient).

LC-MS (method 2): $R_t$=1.78 min; MS (ESIpos): m/z=320 (M+H)$^+$ $^1$H-NMR (400 MHz, DMSO-d$_6$): δ=11.93 (s, 1H), 9.49 (s, 1H), 7.40 (s, 1H), 7.37 (d, 1H), 7.27 (dd, 1H), 4.49 (s, 1H), 4.36 (q, 2H), 2.04 (s, 6H), 1.41 (t, 3H) ppm.

Example 5

N-[5-(3,5-Dicyano-2,6-dimethyl-1,4-dihydropyridin-4-yl)-1H-indazol-3-yl]-2-(2,5-dioxopyrrolidin-1-yl)ethanesulfonamide

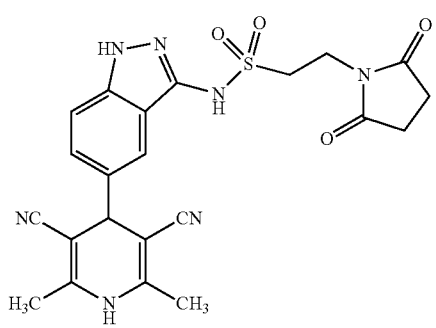 [SMILES: CC1=C(C#N)C(c2ccc3[nH]nc(NS(=O)(=O)CCN4C(=O)CCC4=O)c3c2)C(C#N)=C(C)N1]

The title compound was prepared following the procedure described for Example 1 using 100 mg (0.256 mmol) tert-butyl 3-amino-5-(3,5-dicyano-2,6-dimethyl-1,4-dihydropyridin-4-yl)-1H-indazole-1-carboxylate (Example 3A) and 173 mg (0.77 mmol) 2-(2,5-dioxopyrrolidin-1-yl)ethane-sulfonyl chloride. Yield: 20 mg (17% of th.).

LC-MS (method 1): $R_t$=0.81 min; MS (ESIpos): m/z=480 (M+H)$^+$.

$^1$H-NMR (400 MHz, DMSO-d$_6$): δ=12.84 (s, 1H), 10.4 (s, 1H), 9.55 (s, 1H), 7.63 (s, 1H), 7.50 (d, 1H), 7.32 (d, 1H), 4.51 (s, 1H), 3.84 (t, 1H), 3.61 (t, 2H), 2.5 (s, 4H), 2.05 (s, 6H) ppm.

Example 6

N-[5-(3,5-Dicyano-2,6-dimethyl-1,4-dihydropyridin-4-yl)-1H-indazol-3-yl]-1-(4-fluorophenyl)-methanesulfonamide

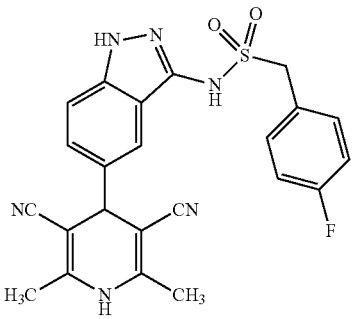 [SMILES: CC1=C(C#N)C(c2ccc3[nH]nc(NS(=O)(=O)Cc4ccc(F)cc4)c3c2)C(C#N)=C(C)N1]

28 mg (0.05 mmol) tert-butyl 5-(3,5-dicyano-2,6-dimethyl-1,4-dihydropyridin-4-yl)-3-{[(4-fluoro-benzyl)sulfonyl]amino}-1H-indazole-1-carboxylate (Example 13A), dissolved in dichloromethane (1 ml), were treated with 0.042 ml (0.55 mmol) trifluoroacetic acid. The mixture was stirred at room temperature for 2 h and then concentrated under reduced pressure. The residue was dissolved in ethyl acetate and washed with saturated aqueous sodium bicarbonate solution. The organic layer was separated, dried over sodium sulfate, filtered, and concentrated under reduced pressure. The residue was purified by preparative RP-HPLC (acetonitrile/water gradient) to give 10 mg (41% of th.) of the title compound.

LC-MS (method 1): $R_t$=1.00 min; MS (ESIpos): m/z=463 (M+H)$^+$ $^1$H-NMR (400 MHz, DMSO-d$_6$): δ=12.82 (s, 1H), 10.23 (s, 1H), 9.53 (s, 1H), 7.61 (s, 1H), 7.50-7.43 (m, 3H), 7.32 (d, 1H), 7.21 (m, 2H), 4.73 (s, 2H), 4.49 (s, 1H), 2.04 (s, 6H) ppm.

Example 7

N-[5-(3,5-Dicyano-2,6-dimethyl-1,4-dihydropyridin-4-yl)-1H-indazol-3-yl]-1-(4-chlorophenyl)-methanesulfonamide

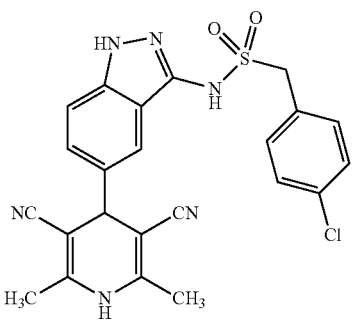 [SMILES: CC1=C(C#N)C(c2ccc3[nH]nc(NS(=O)(=O)Cc4ccc(Cl)cc4)c3c2)C(C#N)=C(C)N1]

The title compound was prepared following the procedure described for Example 6 starting from 100 mg (0.256 mmol) tert-butyl 3-amino-5-(3,5-dicyano-2,6-dimethyl-1,4-dihydropyridin-4-yl)-1H-indazole-1-carboxylate (Example 3A)

and 346 mg (1.54 mmol) (4-chlorophenyl)methane-sulfonyl chloride. Yield: 4 mg (3% of th.).

LC-MS (method 1): $R_t$=1.07 min; MS (ESIpos): m/z=479 (M+H)$^+$ $^1$H-NMR (400 MHz, DMSO-$d_6$): δ=12.83 (s, 1H), 10.28 (s, 1H), 9.53 (s, 1H), 7.61 (s, 1H), 7.52 (d, 1H), 7.46 (s, 4H), 7.33 (d, 1H), 4.74 (s, 2H), 4.49 (s, 1H), 2.05 (s, 6H) ppm.

Example 8

2,6-Dimethyl-4-[3-(phenylsulfonyl)-1H-indazol-5-yl]-1,4-dihydropyridine-3,5-dicarbonitrile

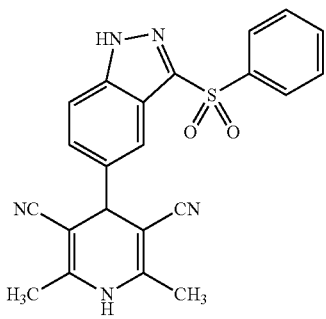 [SMILES: CC1=C(C#N)C(c2ccc3[nH]nc(S(=O)(=O)c4ccccc4)c3c2)C(C#N)=C(C)N1]

The title compound was prepared from Example 15A in close analogy to the procedure described in Example 2 yielding 39 mg (78% of th.) of product after RP-HPLC purification (acetonitrile/water+0.05% TFA gradient).

LC-MS (method 2): $R_t$=1.88 min; MS (ESIpos): m/z=416 (M+H)$^+$ $^1$H-NMR (400 MHz, DMSO-$d_6$): δ=14.31 (s, 1H), 9.59 (s, 1H), 8.00 (m, 2H), 7.90 (s, 1H), 7.75 (d, 1H), 7.70 (m, 1H), 7.60 (m, 2H), 7.48 (dd, 1H), 4.70 (s, 1H), 2.06 (s, 6H) ppm.

Example 9

4-[3-(Cyclopropylmethoxy)-1H-indazol-5-yl]-2,6-dimethyl-1,4-dihydropyridine-3,5-dicarbonitrile

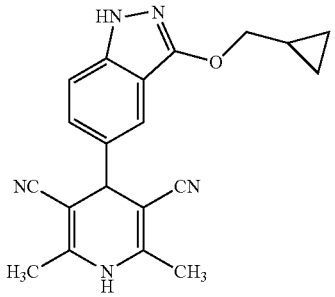 [SMILES: CC1=C(C#N)C(c2ccc3[nH]nc(OCC4CC4)c3c2)C(C#N)=C(C)N1]

The title compound was prepared from Example 17A in close analogy to the procedure described in Example 2 yielding 18 mg (62% of th.) of product after RP-HPLC purification (acetonitrile/water+0.05% TFA gradient).

LC-MS (method 2): $R_t$=1.93 min; MS (ESIpos): m/z=346 (M+H)$^+$ $^1$H-NMR (400 MHz, DMSO-$d_6$): δ=9.49 (s, 1H), 7.43 (s, 1H), 7.37 (d, 1H), 7.27 (dd, 1H), 4.50 (s, 1H), 4.14 (d, 2H), 2.04 (s, 6H), 1.35 (m, 1H), 0.59 (m, 2H), 0.38 (m, 2H) ppm.

Example 10

N-[5-(3,5-Dicyano-2,6-dimethyl-1,4-dihydropyridin-4-yl)-1H-indazol-3-yl]-2-methylpropane-1-sulfonamide

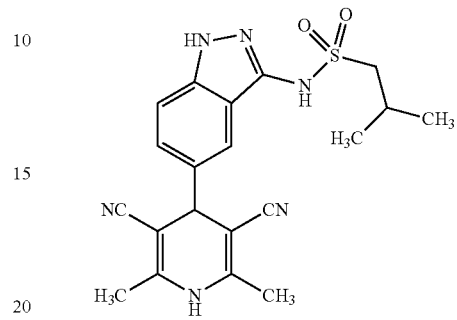

120 mg (0.19 mmol) tert-butyl 3-{bis[(2-methylpropyl)sulfonyl]amino}-5-(3,5-dicyano-2,6-dimethyl-1,4-dihydropyridin-4-yl)-1H-indazole-1-carboxylate (Example 18A) were dissolved in dichloromethane (4 ml) and treated with 0.161 ml (2.1 mmol) trifluoroacetic acid. The mixture was stirred at room temperature for 2 h and then concentrated under reduced pressure. The residue was dissolved in ethyl acetate and washed with saturated aqueous sodium bicarbonate solution. The organic layer was separated, dried over sodium sulfate, filtered, and concentrated under reduced pressure. The residue was dissolved in 1,4-dioxane (4 ml), treated with 1 M aqueous lithium hydroxide solution (0.75 ml) and stirred at room temperature for 4 h. The mixture was then concentrated under reduced pressure, and the residue was purified by preparative RP-HPLC (acetonitrile/water gradient) to give 13 mg (16% of th.) of the title compound.

LC-MS (method 1): $R_t$=0.94 min; MS (ESIpos): m/z=411 (M+H)$^+$ $^1$H-NMR (400 MHz, DMSO-$d_6$): δ=12.76 (s, 1H), 10.19 (s, 1H), 9.54 (s, 1H), 7.63 (s, 1H), 7.49 (d, 1H), 7.31 (d, 1H), 4.50 (s, 1H), 3.27 (d, 2H), 2.24 (m, 1H), 2.05 (s, 6H), 1.05 (d, 6H) ppm.

Example 11

Ethyl 3-{[5-(3,5-dicyano-2,6-dimethyl-1,4-dihydropyridin-4-yl)-1H-indazol-3-yl]sulfamoyl}-propanoate

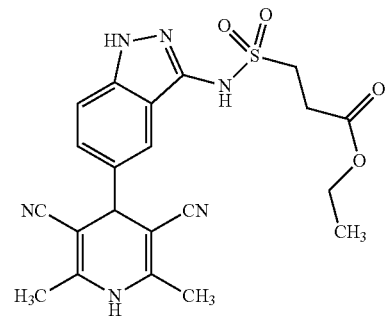 [SMILES: CCOC(=O)CCS(=O)(=O)Nc1n[nH]c2ccc(C3C(C#N)=C(C)NC(C)=C3C#N)cc12]

41 mg (0.073 mmol) tert-butyl 5-(3,5-dicyano-2,6-dimethyl-1,4-dihydropyridin-4-yl)-3-{[(3-ethoxy-3-oxopropyl)sulfonyl]amino}-1H-indazole-1-carboxylate (Example 19A) were dissolved in dichloromethane (4 ml) and treated with 0.062 ml (0.8 mmol) trifluoroacetic acid. The mixture was stirred at room temperature for 2 h and then concentrated under reduced pressure. The residue was dissolved in ethyl acetate and washed with saturated aqueous sodium bicarbonate solution. The organic layer was separated, dried over sodium sulfate, filtered, and concentrated under reduced pressure. The residue was purified by preparative RP-HPLC (acetonitrile/water gradient) to give 33 mg (98% of th.) of the title compound.

LC-MS (method 1): $R_t$=0.91 min; MS (ESIpos): m/z=455 (M+H)$^+$ $^1$H-NMR (400 MHz, DMSO-d$_6$): δ=12.81 (s, 1H), 10.35 (s, 1H), 9.54 (s, 1H), 7.61 (s, 1H), 7.50 (d, 1H), 7.31 (d, 1H), 4.51 (s, 1H), 4.07 (q, 2H), 3.64 (t, 2H), 2.84 (t, 2H), 2.05 (s, 6H), 1.17 (t, 3H) ppm.

Example 12

N-[5-(3,5-Dicyano-2,6-dimethyl-1,4-dihydropyridin-4-yl)-1H-indazol-3-yl]propane-1-sulfonamide

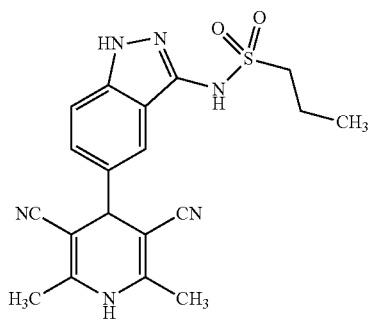 [SMILES: CCCS(=O)(=O)Nc1n[nH]c2ccc(C3C(C#N)=C(C)NC(C)=C3C#N)cc12]

57.8 mg (0.12 mmol) tert-butyl 5-(3,5-dicyano-2,6-dimethyl-1,4-dihydropyridin-4-yl)-3-[(propyl-sulfonyl)amino]-1H-indazole-1-carboxylate (Example 20A) were dissolved in dichloromethane (4 ml) and treated with 0.1 ml (1.28 mmol) trifluoroacetic acid. The mixture was stirred at room temperature for 2 h and then concentrated under reduced pressure. The residue was dissolved in ethyl acetate and washed with saturated aqueous sodium bicarbonate solution. The organic layer was separated, dried over sodium sulfate, filtered, and concentrated under reduced pressure. The residue was purified by preparative RP-HPLC (acetonitrile/water gradient) to give 13 mg (29% of th.) of the title compound.

LC-MS (method 2): $R_t$=1.65 min; MS (ESIpos): m/z=397 (M+H)+

$^1$H-NMR (400 MHz, DMSO-d$_6$): δ=12.75 (s, 1H), 10.15 (s, 1H), 9.54 (s, 1H), 7.62 (s, 1H), 7.49 (d, 1H), 7.31 (d, 1H), 4.50 (s, 1H), 3.3 (m, 2H, under H$_2$O-signal), 1.80 (m, 2H), 2.05 (s, 6H), 1.00 (t, 3H) ppm.

Example 13

4-(3-Methoxy-1H-indazol-5-yl)-2,6-dimethyl-1,4-dihydropyridine-3,5-dicarbonitrile

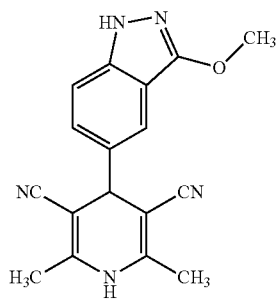

The title compound was prepared from 277 mg (1.57 mmol) of Example 22A in analogy to the procedure described in Example 2 yielding 194 mg (40% of th.) after purification by RP-HPLC (acetonitrile/water gradient).

LC-MS (method 2): $R_t$=1.66 min; MS (ESIpos): m/z=306 (M+H)$^+$ $^1$H-NMR (400 MHz, DMSO-d$_6$): δ=11.91 (s, 1H), 9.50 (s, 1H), 7.41 (s, 1H), 7.38 (d, 1H), 7.27 (dd, 1H), 4.49 (s, 1H), 4.00 (s, 3H), 2.04 (s, 6H) ppm.

Example 14

4-(3-Isopropoxy-1H-indazol-5-yl)-2,6-dimethyl-1,4-dihydropyridine-3,5-dicarbonitrile

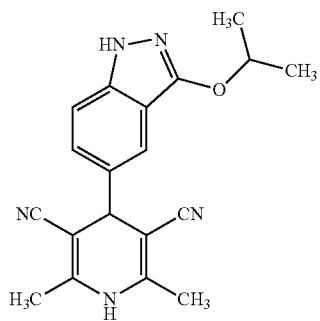 [SMILES: CC1=C(C#N)C(c2ccc3[nH]nc(OC(C)C)c3c2)C(C#N)=C(C)N1]

The title compound was prepared from 101 mg (0.495 mmol) of Example 24A in analogy to the procedure described in Example 2 yielding 58 mg (35% of th.) after purification by RP-HPLC (acetonitrile/water gradient).

LC-MS (method 2): $R_t$=1.87 min; MS (ESIpos): m/z=334 (M+H)$^+$ $^1$H-NMR (400 MHz, DMSO-d$_6$): δ=11.97 (s, 1H), 9.49 (s, 1H), 7.38 (s, 1H), 7.37 (d, 1H), 7.26 (dd, 1H), 5.04 (sept, 1H), 4.50 (s, 1H), 2.04 (s, 6H), 1.39 (d, 6I-1) ppm.

Example 15

4-(3-Isobutoxy-1H-indazol-5-yl)-2,6-dimethyl-1,4-dihydropyridine-3,5-dicarbonitrile

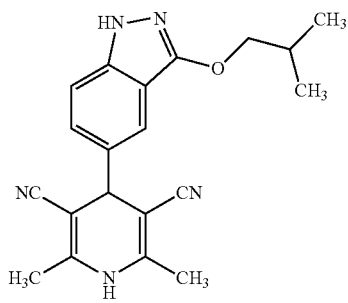 [SMILES: CC1=C(C#N)C(c2ccc3[nH]nc(OCC(C)C)c3c2)C(C#N)=C(C)N1]

The title compound was prepared from 132 mg (0.605 mmol) of Example 26A in analogy to the procedure described in Example 2 yielding 24 mg (11% of th.) after purification by RP-HPLC (acetonitrile/water gradient).

LC-MS (method 2): $R_t$=2.02 min; MS (ESIpos): m/z=348 (M+H)$^+$ $^1$H-NMR (400 MHz, DMSO-d$_6$): δ=11.93 (s, 1H), 9.50 (s, 1H), 7.42 (s, 1H), 7.39 (d, 1H), 7.27 (dd, 1H), 4.51 (s, 1H), 4.10 (d, 2H), 2.14 (m, 1H), 2.04 (s, 6H), 1.01 (d, 6H) ppm.

Example 16

4-[3-(Cyclobutylmethoxy)-1H-indazol-5-yl]-2,6-dimethyl-1,4-dihydropyridine-3,5-dicarbonitrile

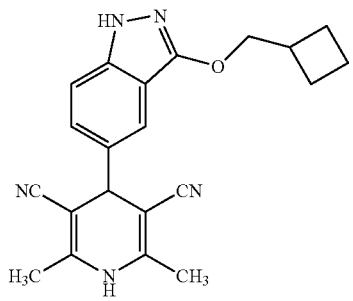 [SMILES: CC1=C(C#N)C(c2ccc3[nH]nc(OCC4CCC4)c3c2)C(C#N)=C(C)N1]

The title compound was prepared from 151 mg (0.656 mmol) of Example 28A in analogy to the procedure described in Example 2 yielding 87 mg (37% of th.) after purification by RP-HPLC (acetonitrile/water gradient).

LC-MS (method 2): $R_t$=2.06 min; MS (ESIpos): m/z=360 (M+H)$^+$ $^1$H-NMR (400 MHz, DMSO-d$_6$): δ=11.94 (s, 1H), 9.49 (s, 1H), 7.40 (s, 1H), 7.38 (d, 1H), 7.27 (dd, 1H), 4.51 (s, 1H), 4.30 (d, 2H), 2.82 (m, 1H), 2.11 (m, 2H), 2.04 (s, 6H), 1.91 (m, 4H) ppm.

Example 17

2,6-Dimethyl-4-(3-propoxy-1H-indazol-5-yl)-1,4-dihydropyridine-3,5-dicarbonitrile

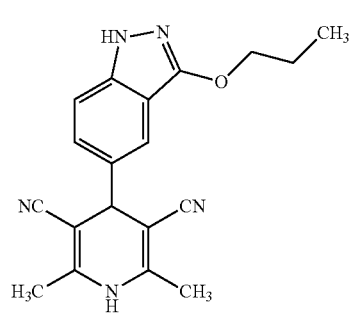 [SMILES: CCCOc1n[nH]c2ccc(C3C(C#N)=C(C)NC(C)=C3C#N)cc12]

The title compound was prepared from 141 mg (0.686 mmol) of Example 30A in analogy to the procedure described in Example 2 yielding 75 mg (32% of th.) after purification by RP-HPLC (acetonitrile/water gradient).

LC-MS (method 2): $R_t$=1.89 min; MS (ESIpos): m/z=334 (M+H)$^+$ $^1$H-NMR (400 MHz, DMSO-d$_6$): δ=11.92 (s, 1H), 9.49 (s, 1H), 7.41 (s, 1H), 7.37 (d, 1H), 7.27 (dd, 1H), 4.50 (s, 1H), 4.27 (t, 2H), 2.04 (s, 6H), 1.83 (m, 2H), 1.01 (t, 2H) ppm.

Example 18

4-[3-(2-Isopropoxyethoxy)-1H-indazol-5-yl]-2,6-dimethyl-1,4-dihydropyridine-3,5-dicarbonitrile

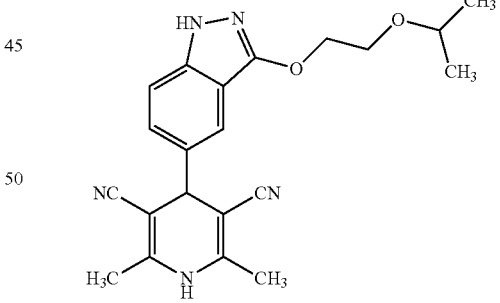

The title compound was prepared from 150 mg (0.604 mmol) of Example 32A in analogy to the procedure described in Example 2 yielding 167 mg (72% of th.) after purification by RP-HPLC (acetonitrile/water gradient).

LC-MS (method 2): $R_t$=1.86 min; MS (ESIpos): m/z=378 (M+H)$^+$ $^1$H-NMR (400 MHz, DMSO-d$_6$): δ=11.97 (s, 1H), 9.50 (s, 1H), 7.42 (s, 1H), 7.39 (d, 1H), 7.28 (dd, 1H), 4.51 (s, 1H), 4.40 (m, 2H), 3.77 (m, 2H), 3.65 (m, 1H), 2.04 (s, 6H), 1.12 (d, 6H) ppm.

Example 19

2,6-Dimethyl-4-{3-[2-(morpholin-4-yl)ethoxy]-1H-indazol-5-yl}-1,4-dihydropyridine-3,5-dicarbonitrile

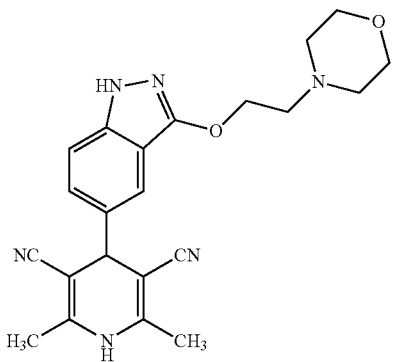 [SMILES: CC1=C(C#N)C(c2ccc3[nH]nc(OCCN4CCOCC4)c3c2)C(C#N)=C(C)N1]

The title compound was prepared from 98 mg (0.356 mmol) of Example 34A in analogy to the procedure described in Example 2 yielding 20 mg (13% of th.) after purification first by RP-HPLC (acetonitrile/water gradient) followed by silica gel chromatography (dichloromethane/methanol gradient).

LC-MS (method 2): $R_t$=1.26 min; MS (ESIpos): m/z=405 (M+H)$^+$ $^1$H-NMR (400 MHz, DMSO-d$_6$): δ=11.97 (br. s, 1H), 9.51 (s, 1H), 7.41 (s, 1H), 7.39 (d, 1H), 7.28 (d, 1H), 4.51 (s, 1H), 4.44 (m, 2H), 3.58 (m, 4H), 2.77 (m, 2H), 2.04 (s, 6H) ppm.

Example 20

2,6-Dimethyl-4-{3-[2-(piperidin-1-yl)ethoxy]-1H-indazol-5-yl}-1,4-dihydropyridine-3,5-dicarbonitrile

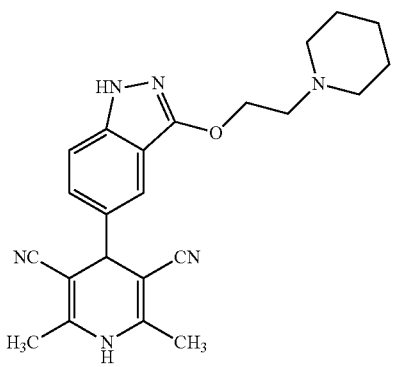 [SMILES: CC1=C(C#N)C(c2ccc3[nH]nc(OCCN4CCCCC4)c3c2)C(C#N)=C(C)N1]

The title compound was prepared from 278 mg (1.01 mmol) of Example 36A in analogy to the procedure described in Example 2 yielding 119 mg (29% of th.) after purification first by RP-HPLC (acetonitrile/water gradient) followed by silica gel chromatography (dichloromethane/methanol gradient).

LC-MS (method 2): $R_t$=1.34 min; MS (ESIpos): m/z=403 (M+H)$^+$ $^1$H-NMR (400 MHz, DMSO-d$_6$): δ=12.01 (br. s, 1H), 9.55 (s, 1H), 7.42 (s, 1H), 7.39 (d, 1H), 7.28 (d, 1H), 4.51 (s, 1H), 4.48 (m, 2H), 3.32 (m, 4H), 2.04 (s, 6H), 1.58 (m, 2H), 1.42 (m, 2H) ppm.

Example 21

2,6-Dimethyl-4-{3-[2-(1H-pyrazol-1-yl)ethoxy]-1H-indazol-5-yl}-1,4-dihydropyridine-3,5-dicarbonitrile

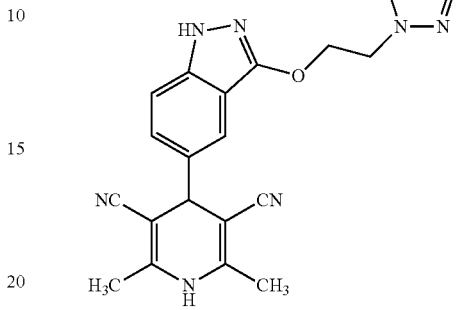

The title compound was prepared from 59 mg (0.230 mmol) of Example 38A in analogy to the procedure described in Example 2 yielding 30 mg (33% of th.) after purification by RP-HPLC (acetonitrile/water gradient).

LC-MS (method 2): $R_t$=1.70 min; MS (ESIpos): m/z=386 (M+H)$^+$ $^1$H-NMR (400 MHz, DMSO-d$_6$): δ=12.04 (br. s, 1H), 9.50 (s, 1H), 7.80 (d, 2H), 7.46 (d, 2H), 7.40 (d, 1H), 7.35 (s, 1H), 7.28 (d, 1H), 6.25 (t, 1H), 4.65 (m, 2H), 4.59 (m, 2H), 4.49 (s, 1H), 2.04 (s, 6H) ppm.

Example 22

4-[3-(3,5-Difluorophenoxy)-1H-indazol-5-yl]-2,6-dimethyl-1,4-dihydropyridine-3,5-dicarbonitrile

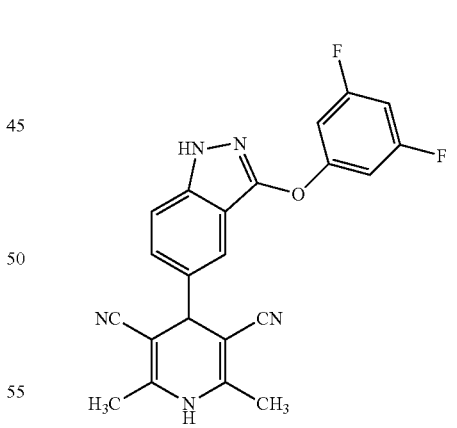

The title compound was prepared from 57 mg (0.211 mmol) of Example 40A in analogy to the procedure described in Example 2 yielding 39 mg (45% of th.) after purification by RP-HPLC (acetonitrile/water gradient).

LC-MS (method 2): $R_t$=2.11 min; MS (ESIpos): m/z=404 (M+H)$^+$ $^1$H-NMR (400 MHz, DMSO-d$_6$): δ=12.72 (s, 1H), 9.51 (s, 1H), 7.57 (d, 2H), 7.38 (d, 1H), 7.35 (s, 1H), 7.02 (m, 3H), 4.53 (s, 1H), 2.03 (s, 6H) ppm.

Example 23

4-(3-{[4-(Diethylamino)phenyl]sulfanyl}-1H-indazol-5-yl)-2,6-dimethyl-1,4-dihydropyridine-3,5-dicarbonitrile

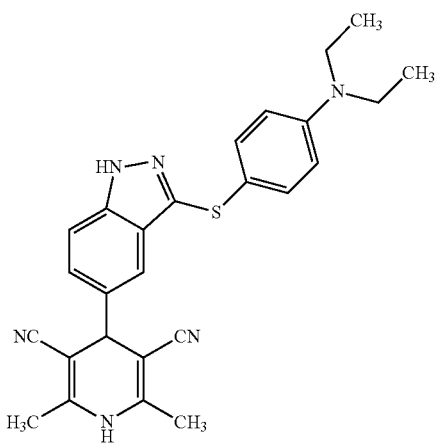 [SMILES: CCN(CC)c1ccc(Sc2n[nH]c3ccc(C4C(C#N)=C(C)NC(C)=C4C#N)cc23)cc1]

The title compound was prepared from 530 mg (1.630 mmol) of Example 42A in analogy to the procedure described in Example 2 yielding 264 mg (35% of th.) after purification by RP-HPLC (acetonitrile/water gradient).

LC-MS (method 2): $R_t$=1.67 min; MS (ESIpos): m/z=455 (M+H)$^+$ $^1$H-NMR (400 MHz, DMSO-d$_6$): δ=13.29 (s, 1H), 9.51 (s, 1H), 7.56 (d, 1H), 7.39 (s, 1H), 7.29 (m, 3H), 6.58 (d, 2H), 4.48 (s, 1H), 3.30 (m, 4H), 2.03 (s, 6H), 1.04 (t, 6H) ppm.

Example 24

2,6-Bis(difluoromethyl)-4-{3-[2-(propan-2-yloxy)ethoxy]-1H-indazol-5-yl}-1,4-dihydropyridine-3,5-dicarbonitrile

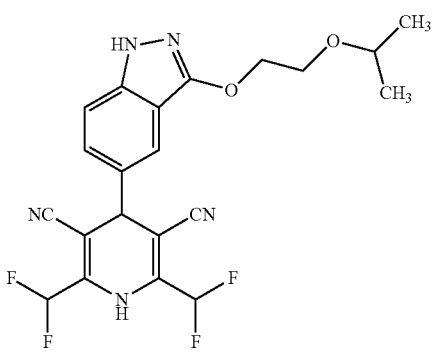 [SMILES: CC(C)OCCOc1n[nH]c2ccc(C3C(C#N)=C(C(F)F)NC(C(F)F)=C3C#N)cc12]

80 mg (0.32 mmol) 3-(2-isopropoxyethoxy)-1H-indazole-5-carbaldehyde (Example 32A), 84 mg (0.71 mmol) 3-amino-4,4-difluorobut-2-enenitrile [obtainable by Thorpe reaction of acetonitrile with 2,2-difluoroacetonitrile, cf. *Org. React.* 15, 1 (1967), *ibid.* 31, 1 (1984)] and a small amount of powdered 4 Å molecular sieve in acetic acid (310 μl) were heated to 115° C. for 1 h. After cooling to room temperature, the reaction mixture was diluted with THF and filtered. The filtrate was directly purified by preparative RP-HPLC (acetonitrile/water+0.05% TFA gradient) to give 85 mg (59% of th.) of the title compound.

LC-MS (method 5): $R_t$=0.98 min; MS (ESIpos): m/z=450 (M+H)$^+$ $^1$H-NMR (400 MHz, DMSO-d$_6$): δ=12.08 (s, 1H), 10.64 (s, 1H), 7.53 (s, 1H), 7.48 (d, 1H), 7.32 (d, 1H), 6.82 (t, 2H), 4.90 (s, 1H), 4.40 (m, 2H), 3.78 (m, 2H), 3.65 (m, 1H), 1.12 (d, 6H) ppm.

Example 25

4-{3-[(2-Methoxyethyl)(methyl)amino]-1H-indazol-5-yl}-2,6-dimethyl-1,4-dihydropyridine-3,5-dicarbonitrile

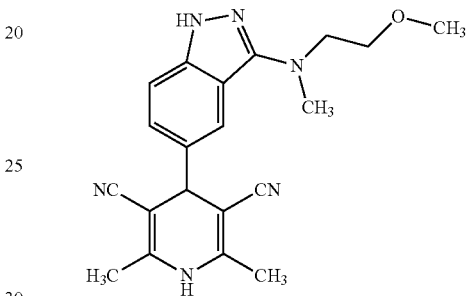

The title compound was prepared from 136 mg (0.583 mmol) 3-[(2-methoxyethyl)(methyl)amino]-1H-indazole-5-carbaldehyde (Example 48A) in analogy to the procedure described in Example 2 yielding 39 mg (17% of th.) after purification by RP-HPLC (acetonitrile/water gradient, final mixture 90:10 v/v).

LC-MS (method 5): $R_t$=0.82 min; MS (ESIpos): m/z=363 (M+H)$^+$ $^1$H-NMR (400 MHz, DMSO-d$_6$): δ=11.84 (s, 1H), 9.46 (s, 1H), 7.59 (s, 1H), 7.34 (d, 1H), 7.20 (d, 1H), 4.46 (s, 1H), 3.56 (m, 4H), 3.27 (s, 3H), 3.04 (s, 3H), 2.04 (s, 6H) ppm.

Example 26

4-{3-[(3-Methoxypropyl)(methyl)amino]-1H-indazol-5-yl}-2,6-dimethyl-1,4-dihythopyridine-3,5-dicarbonitrile

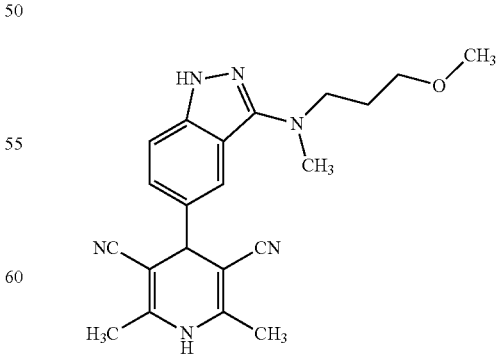

The title compound was prepared from 106 mg (0.429 mmol) 3-[(3-methoxypropyl)(methyl)-amino]-1H-indazole-5-carbaldehyde (Example 51A) in analogy to the procedure described in Example 2 yielding 17 mg (10% of th.) after purification by RP-HPLC (acetonitrile/water gradient, final mixture 90:10 v/v).

LC-MS (method 5): $R_t$=0.82 min; MS (ESIpos): m/z=377 (M+H)$^+$ $^1$H-NMR (400 MHz, DMSO-d$_6$): δ=11.85 (s, 1H), 9.49 (s, 1H), 7.58 (s, 1H), 7.35 (d, 1H), 7.20 (d, 1H), 4.45 (s, 1H), 3.48-3.38 (m, 4H), 3.23 (s, 3H), 2.96 (s, 3H), 2.04 (s, 6H), 1.89 (m, 2H) ppm.

B. EVALUATION OF BIOLOGICAL ACTIVITY

Demonstration of the activity of the compounds of the present invention may be accomplished through in vitro, ex vivo, and in vivo assays that are well known in the art. For example, to demonstrate the activity of the compounds of the present invention, the following assays may be used.

c-Met Receptor Tyrosine Kinase Activity Assay (NADH Read-Out):

Recombinant human c-Met protein (Invitrogen, Carlsbad, Calif., USA) is used. As substrate for the kinase reaction the peptide KKKSPGEYVNIEFG (JPT, Germany) is used. For the assay, 1 μL of a 51-fold concentrated solution of the test compound in DMSO is pipetted into a white 384-well microtiter plate (Greiner Bio-One, Frickenhausen, Germany). 25 μL of a solution of c-Met (final concentration 30 nM) and pyruvate kinase/lactate dehydrogenase (Roche Diagnostics, Mannheim, Germany; final concentration 8 mg/L) in assay buffer [3-(N-morpholino)propane-sulfonic acid (MOPS), 50 mM, pH 7; MgCl$_2$, 10 mM; bovine serum albumin (BSA), 0.01%; Triton X 100, 0.01%; DTT, 2 mM] are added, and the mixture is incubated for 5 min at room temperature. Then, the kinase reaction is started by the addition of 25 μL of a solution of adenosine triphosphate (ATP, final concentration 30 μM), substrate (final concentration 100 μM), nicotinamide adenine dinucleotide (NADH, final concentration 50 μM) and dithiothreitol (DTT, final concentration 2 mM) in assay buffer, and the resulting mixture is incubated for a reaction time of 100 min at 32° C.

Subsequently, the amount of phosphorylated substrate is evaluated by measurement of the decrease of NADH fluorescence. Therefore, the fluorescence emissions at 465 nm after excitation at 340 nm is measured in a fluorescence reader, e.g. Tecan Ultra (Tecan, Männedorf, Switzerland). The data are normalised (enzyme reaction without inhibitor=0% inhibition; all other assay components but no enzyme=100% inhibition). Normally, test compounds are tested on the same microtiter plate at 9 different concentrations in the range of 10 μM to 1 nM (10 μM, 3.1 μM, 1.0 μM, 0.3 μM, 0.1 μM, 0.03 μM, 0.01 μM, 0.003 μM, 0.001 μM; dilution series prepared before the assay at the level of the 51-fold concentrated stock solutions by serial 1:3 dilutions) in duplicate for each concentration, and IC$_{50}$ values are calculated using an inhouse software.

Compounds of the invention, when tested in this assay, demonstrated the ability to inhibit c-Met tyrosine kinase activity at IC$_{50}$ values of less than 10 μM, preferably at less than 1 μM.

Some representative IC$_{50}$ values are listed in the table below:

| Example No. | IC$_{50}$ [μM] |
| --- | --- |
| 2 | 0.007 |
| 3 | 0.077 |
| 12 | 0.475 |
| 13 | 0.008 |
| 24 | 0.038 |
| 25 | 0.008 | c-Met Receptor Tyrosine Kinase Homogeneous Time-Resolved Fluorescence Assay (Alternative Format):

The N-terminally His6-tagged recombinant kinase domain of the human c-Met (amino acids 960-1390), expressed in insect cells (SF21) and purified by Ni-NTA affinity chromatography and consecutive size exclusion chromatography (Superdex 200), is used. Alternatively, commercially available c-Met (Millipore) can be used. As substrate for the kinase reaction, the biotinylated poly-Glu, Tyr (4:1) copolymer (#61GT0BLC, C is Biointernational, Marcoule, France) is used.

For the assay, 50 mL of a 100-fold concentrated solution of the test compound in DMSO is pipetted into a black low-volume 384-well microtiter plate (Greiner Bio-One, Frickenhausen, Germany). 2 μL of a solution of c-Met in assay buffer [25 mM Hepes/NaOH, pH 7.5; 5 mM MgCl$_2$; 5 mM MnCl$_2$; 2 mM dithiothreitol; 0.1% (v/v) Tween 20 (Sigma); 0.1% (w/v) bovine serum albumin] are added, and the mixture is incubated for 15 mM at 22° C. to allow pre-binding of the test compound to the enzyme before the start of the kinase reaction. Then, the kinase reaction is started by the addition of 3 μL of a solution of adenosine triphosphate (ATP, 16.7 μM; final concentration in the 5 μL assay volume is 10 μM) and substrate (2.27 μg/mL, final concentration in the 5 μL assay volume is 1.36 μg/mL~30 nM) in assay buffer, and the resulting mixture is incubated for a reaction time of 30 min at 22° C. The concentration of c-Met in the assay is adjusted depending on the activity of the enzyme lot and is appropriately chosen to have the assay in the linear range; typical enzyme concentrations are in the range of about 0.03 nM (final concentration in the 5 μL assay volume). The reaction is stopped by the addition of 5 μL of a solution of HTRF detection reagents [40 nM streptavidine-XLent and 2.4 nM PT66-Eu-chelate, an europium-chelate labelled anti-phosphotyrosine antibody (Perkin-Elmer)] in an aqueous EDTA solution [100 mM EDTA, 0.2% (w/v) bovine serum albumin in 50 mM HEPES/NaOH, pH 7.5].

The resulting mixture is incubated for 1 h at 22° C. to allow the binding of the biotinylated phosphorylated peptide to the streptavidine-XLent and the PT66-Eu-chelate. Subsequently, the amount of phosphorylated substrate is evaluated by measurement of the resonance energy transfer from the PT66-Eu-chelate to the streptavidine-XLent. Therefore, the fluorescence emissions at 620 nm and 665 nm after excitation at 350 nm are measured in an HTRF reader, e.g. Rubystar (BMG Lab-technologies, Offenburg, Germany) or Viewlux (Perkin-Elmer). The ratio of the emissions at 665 nm and at 622 nm is taken as the measure for the amount of phosphorylated substrate. The data are normalised (enzyme reaction without inhibitor=0% inhibition; all other assay components but no enzyme=100% inhibition). Normally, test compounds are tested on the same micro-titer plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM; dilution series prepared before the assay at the level of the 100-fold concentrated stock solutions by serial 1:3 dilutions) in duplicate for each concentration, and IC$_{50}$ values are calculated by a 4-parameter-fit using an inhouse software.

Compounds of the invention, when tested in this assay, demonstrated the ability to inhibit c-Met tyrosine kinase activity at $IC_{50}$ values of less than 10 µM, preferably at less than 1 µM.

Some representative $IC_{50}$ values are listed in the table below:

| Example No. | $IC_{50}$ [µM] |
|---|---|
| 2 | 0.008 |
| 3 | 0.130 |
| 12 | 0.761 |
| 18 | 0.001 |
| 20 | 0.015 |
| 25 | 0.013 |

Phospho-c-Met Assay:

This is a cell based, ELISA-like assay [Meso Scale Discovery (MSD), Gaithersburg, Md., USA] using MKN-45 tumor cells (gastric carcinoma, purchased from ATCC) without growth factor stimulation. The cells are plated in full growth media (10 000 cells/well) in 96-well plates on day one. On day two, after a two-hour drug treatment in serum-free media, cells are washed and then lysed (60 µl/well using MSD recommended lysis buffer) and frozen at −80° C. Also on day two, non-specific antibody-binding sites on the MSD phospho-Met plates are blocked with MSD Blocking Solution A overnight at 4° C. On day three, frozen lysates are thawed on ice, and 25 µl of lysate is transferred to the MSD phospho-Met plate, for 1 hour with shaking, after washing once with Tris-buffered saline+0.05% Tween 20 (TBST). After removing the unbound proteins, the Sulfa-TAG anti-Met antibody from MSD is added at a final concentration of 5 nM in antibody dilution buffer (following protocol of MSD) to the plate for 1 hour with shaking. The plate is then washed with TBST buffer three times before adding 1×MSD Read Buffer. The plate is then read on the MSD Discovery Workstation instrument. Raw data, including wells with 10 µM of a reference compound (minimum signal), and DMSO wells without any drug treatment (maximum signal), are entered into the Analyze 5 program for $IC_{50}$ value determinations.

Cellular Phospho-c-Met Assay:

Human gastric adenocarcinoma cells (MKN45, purchased from ATCC) seeded on 384-well micro-titer plates (9000 cells/well) are incubated in 25 µl full growth media for 24 h at 37° C. with 5% $CO_2$. On day two, after a two-hour drug treatment in serum-reduced media containing 0.1% FCS, cells are washed and lysed. Lysates are transferred to BSA-blocked plates with prebound c-Met capture antibody [purchased from Mesoscale Discovery (MSD), Gaithersburg, Md., USA] for 1 hour with shaking, after washing once with Tris-buffered saline+0.05% Tween 20 (TBST). Following the MSD protocol, the Sulfa-TAG anti-phospho-c-Met detection antibody is added at a final concentration of 5 nM in antibody dilution buffer to the plate for 1 hour with shaking at RT. After washing the wells with Tris buffer, 1× reading buffer is added, and the plates are measured on the Sector Imager 6000 (purchased from Mesoscale). $IC_{50}$ values are calculated from dose-response curves using Marquardt-Levenberg-Fit.

In-Vitro Tumor Cell Proliferation Assay:

The adherent tumor cell proliferation assay used to test the compounds of the present invention involves a read-out called Cell Titre-Glo developed by Promega [B. A. Cunningham, "A Growing Issue: Cell Proliferation Assays. Modern kits ease quantification of cell growth", *The Scientist* 2001, 15 (13), 26; S. P. Crouch et al., "The use of ATP bioluminescence as a measure of cell proliferation and cytotoxicity", *Journal of Immunological Methods* 1993, 160, 81-88]. Generation of a luminescent signal corresponds to the amount of ATP present, which is directly proportional to the number of metabolically active (proliferating) cells.

H460 cells (lung carcinoma, purchased from ATCC) are plated in 96-well plates at 3000 cells/well in complete media with 10% fetal calf serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titre-Glo Luminescent® assay kit, the cells are lysed, and 100 µl of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$ values, a linear regression analysis can be used to determine the drug concentration which results in a 50% inhibition of cell proliferation using this assay format. This protocol can be applied to different cell lines of interest, which include, but not limited to, CAKI-1, MNK-45, GTL-16, HCC2998, K562, H441, K812, MEG01, SUP15 and HCT116.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile I.V. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for I.V. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxy-methylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:

1. A compound of formula (I)

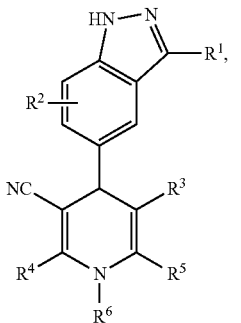

wherein $R^1$ is a group of the formula —$NR^7R^8$, —$NR^9$—$C(=O)$—$R^{10}$, —$NR^{11}$—$SO_2$—$R^{12}$, —$OR^{13}$, —$S(=O)_n$—$R^{14}$ or —$SO_2$—$NR^{15}R^{16}$, wherein n is 0, 1 or 2, $R^7, R^8, R^{10}, R^{12}, R^{13}$ and $R^{14}$ are independently selected from the group consisting of $(C_1$-$C_6)$-alkyl, $(C_3$-$C_7)$-cycloalkyl, phenyl, 4- to 7-membered heterocycloalkyl and 5- to 10-membered heteroaryl, wherein (i) said $(C_3$-$C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1$-$C_4)$-alkyl, oxo, hydroxy, difluoromethoxy, trifluoromethoxy, $(C_1$-$C_4)$-alkoxy, amino, mono-$(C_1$-$C_4)$-alkylamino, di-$(C_1$-$C_4)$-alkylamino and $(C_3$-$C_6)$-cycloalkyl, and (ii) said $(C_1$-$C_6)$-alkyl is optionally substituted with one, two or three substituents independently selected from the group consisting of fluoro, trifluoromethyl, hydroxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, aminocarbonyl, mono-$(C_1$-$C_4)$-alkylaminocarbonyl, di-$(C_1$-$C_4)$-alkylaminocarbonyl, $(C_3$-$C_7)$-cycloalkyl, phenyl, 4- to 7-membered heterocycloalkyl and 5- to 10-membered heteroaryl, wherein said $(C_3$-$C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1$-$C_4)$-alkyl, oxo, hydroxy, difluoromethoxy, trifluoromethoxy, $(C_1$-$C_4)$-alkoxy, amino, mono-$(C_1$-$C_4)$-alkylamino, di-$(C_1$-$C_4)$-alkylamino and $(C_3$-$C_6)$-cycloalkyl, $R^9$ is $(C_1$-$C_6)$-alkyl, $R^{11}$ is hydrogen or $(C_1$-$C_6)$-alkyl, or $R^{11}$ and $R^{12}$ are joined and, taken together with the nitrogen atom and $SO_2$ group to which they are attached, form a heterocyclic moiety of the formula

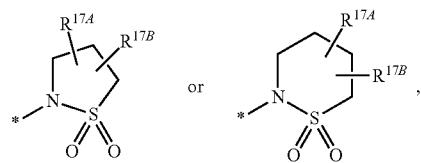

wherein * denotes the point of attachment to the indazole moiety, and $R^{17A}$ and $R^{17B}$ are independently selected from the group consisting of hydrogen, fluoro and $(C_1$-$C_4)$-alkyl, $R^{15}$ and $R^{16}$ are independently selected from the group consisting of hydrogen, $(C_1$-$C_6)$-alkyl, $(C_3$-$C_7)$-cycloalkyl, phenyl, 4- to 7-membered heterocycloalkyl and 5- to 10-membered heteroaryl, wherein (i) said $(C_3$-$C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1$-$C_4)$-alkyl, oxo, hydroxy, difluoromethoxy, trifluoromethoxy, $(C_1$-$C_4)$-alkoxy, amino, mono-$(C_1$-$C_4)$-alkylamino, di-$(C_1$-$C_4)$-alkylamino and $(C_3$-$C_6)$-cycloalkyl, and (ii) said $(C_1$-$C_6)$-alkyl is optionally substituted with one, two or three substituents independently selected from the group consisting of fluoro, trifluoromethyl, hydroxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, aminocarbonyl, mono-$(C_1$-$C_4)$-alkylaminocarbonyl, di-$(C_1$-$C_4)$-alkylaminocarbonyl, $(C_3$-$C_7)$-cycloalkyl, phenyl, 4- to 7-membered heterocycloalkyl and 5- to 10-membered heteroaryl, wherein said $(C_3$-$C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1$-$C_4)$-alkyl, oxo, hydroxy, difluoromethoxy, trifluoromethoxy, $(C_1$-$C_4)$-alkoxy, amino, mono-$(C_1$-$C_4)$-alkylamino, di-$(C_1$-$C_4)$-alkylamino and $(C_3$-$C_6)$-cycloalkyl, or $R^{15}$ and $R^{16}$ are joined and, taken together with the nitrogen atom to which they are attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^2$ is hydrogen, fluoro, chloro or methyl, $R^3$ is cyano or a group of the formula —C(=O)—OR$^{18}$ or —C(=O)—NR$^{19}$R$^{20}$, wherein $R^{18}$ is $(C_1-C_6)$-alkyl optionally substituted with $(C_3-C_7)$-cycloalkyl, or is $(C_4-C_7)$-cycloalkyl, and $R^{19}$ and $R^{20}$ are independently selected from the group consisting of hydrogen, $(C_1-C_6)$-alkyl and $(C_3-C_7)$-cycloalkyl, wherein said $(C_1-C_6)$-alkyl is optionally substituted with $(C_3-C_7)$-cycloalkyl, $R^4$ is $(C_1-C_4)$-alkyl optionally substituted with up to three fluoro atoms, or is cyclopropyl or amino, $R^5$ is $(C_1-C_6)$-alkyl optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocycloalkyl, wherein (i) said $(C_1-C_4)$-alkoxy substituent is optionally further substituted with a residue selected from the group consisting of hydroxy, $(C_1-C_4)$-alkoxy, amino, mono-$(C_1-C_4)$-alkylamino, di-$(C_1-C_4)$-alkylamino and 4- to 7-membered heterocycloalkyl, and (ii) said mono-$(C_1-C_4)$-alkylamino and di-$(C_1-C_4)$-alkylamino substituents are optionally further substituted with one or two residues selected from the group consisting of hydroxy and $(C_1-C_4)$-alkoxy, or $R^5$ is selected from the group consisting of $(C_3-C_7)$-cycloalkyl, phenyl and 5- or 6-membered heteroaryl each of which is optionally substituted with one or two substituents independently selected from the group consisting of fluoro, chloro, difluoromethyl, trifluoromethyl, $(C_1-C_4)$-alkyl, hydroxy, difluoromethoxy, trifluoromethoxy, $(C_1-C_4)$-alkoxy, amino, mono-$(C_1-C_4)$-alkylamino and di-$(C_1-C_4)$-alkylamino, and $R^6$ is hydrogen, $(C_1-C_4)$-alkyl or cyclopropyl.

2. The compound of formula (I) according to claim 1, wherein $R^1$ is a group of the formula —NR$^7$R$^8$, —NR$^9$—C(=O)—R$^{10}$, —NR$^{11}$—SO$_2$—R$^{12}$, —OR$^{13}$, —S(=O)$_n$—R$^{14}$ or —SO$_2$—NR$^{15}$R$^{16}$, wherein n is 0 or 2, $R^7$ is $(C_1-C_4)$-alkyl optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino, $R^8$, $R^{10}$, $R^{12}$, $R^{13}$ and $R^{14}$ are each selected from the group consisting of $(C_1-C_6)$-alkyl, $(C_3-C_6)$-cycloalkyl, phenyl, 4- to 6-membered heterocycloalkyl and 5- or 6-membered heteroaryl, wherein (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl, wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, $R^9$ is $(C_1-C_4)$-alkyl, $R^{11}$ is hydrogen or $(C_1-C_4)$-alkyl, or $R^{11}$ and $R^{12}$ are joined and, taken together with the nitrogen atom and SO$_2$ group to which they are attached, form a heterocyclic moiety of the formula

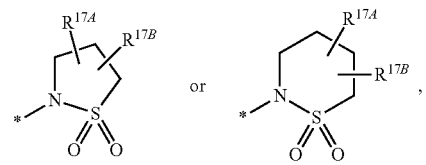

wherein * denotes the point of attachment to the indazole moiety, and $R^{17A}$ and $R^{17B}$ are independently hydrogen or methyl, $R^{15}$ is hydrogen or $(C_1-C_4)$-alkyl optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino, $R^{16}$ is selected from the group consisting of hydrogen, $(C_1-C_6)$-alkyl, $(C_3-C_6)$-cycloalkyl, phenyl, 4- to 6-membered heterocycloalkyl and 5- or 6-membered heteroaryl, wherein (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, and (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$- alkylaminocarbonyl, $(C_3-C_6)$-cycloalkyl, phenyl, 4- to 6-membered heterocycloalkyl and 5- or 6-membered heteroaryl,
wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
or
$R^{15}$ and $R^{16}$ are joined and, taken together with the nitrogen atom to which they are attached, form a 4- to 6-membered heterocycloalkyl ring, which may contain a second ring heteroatom selected from N, O and S, and which is optionally substituted with one or two substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino, $R^2$ is hydrogen, fluoro or chloro, $R^3$ is cyano or a group of the formula —C(=O)—OR$^{18}$ or —C(=O)—NR$^{19}$R$^{20}$, wherein
$R^{18}$ is $(C_1-C_4)$-alkyl,
and
$R^{19}$ and $R^{20}$ are independently selected from the group consisting of hydrogen and $(C_1-C_4)$-alkyl, $R^4$ is $(C_1-C_4)$-alkyl optionally substituted with up to three fluoro atoms, or is amino, $R^5$ is $(C_1-C_6)$-alkyl optionally substituted with up to three fluoro atoms or with one or two substituents independently selected from the group consisting of hydroxy, $(C_1-C_4)$-alkoxy, amino, mono-$(C_1-C_4)$-alkylamino, di-$(C_1-C_4)$-alkylamino, $(C_3-C_6)$-cycloalkyl and 4- to 6-membered heterocycloalkyl, wherein
(i) said $(C_1-C_4)$-alkoxy substituent is optionally further substituted with a residue selected from the group consisting of hydroxy, $(C_1-C_4)$-alkoxy, amino, mono-$(C_1-C_4)$-alkylamino, di-$(C_1-C_4)$-alkylamino and 4- to 6-membered heterocycloalkyl,
and
(ii) said mono-$(C_1-C_4)$-alkylamino and di-$(C_1-C_4)$-alkylamino substituents are optionally further substituted with one or two residues selected from the group consisting of hydroxy and $(C_1-C_4)$-alkoxy,
or
$R^5$ is selected from the group consisting of $(C_3-C_6)$-cycloalkyl, phenyl and 5- or 6-membered heteroaryl each of which is optionally substituted with one or two substituents independently selected from the group consisting of fluoro, chloro, difluoromethyl, trifluoromethyl, $(C_1-C_4)$-alkyl, hydroxy, $(C_1-C_4)$-alkoxy, mono-$(C_1-C_4)$-alkylamino and di-$(C_1-C_4)$-alkylamino,
and
$R^6$ is hydrogen or $(C_1-C_4)$-alkyl.

3. The compound of formula (I) according to claim 1, wherein
$R^1$ is a group of the formula —NR$^7$R$^8$, —NR$^9$—C(=O)—R$^{10}$, —NR$^{11}$—SO$_2$—R$^{12}$, —OR$^{13}$, —S(=O)$_n$—R$^{14}$ or —SO$_2$—NR$^{15}$R$^{16}$, wherein
n is 0 or 2,
$R^7$ is $(C_1-C_4)$-alkyl optionally substituted with hydroxy, methoxy, ethoxy, amino, methylamino, ethylamino, dimethylamino or diethylamino, $R^8$, $R^{10}$, $R^{12}$, $R^{13}$ and $R^{14}$ are each selected from the group consisting of $(C_1-C_4)$-alkyl, $(C_3-C_6)$-cycloalkyl and 5- or 6-membered heterocycloalkyl, wherein
(i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
and
(ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl,
wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, $R^9$ is methyl or ethyl, $R^{11}$ is hydrogen, methyl or ethyl, or $R^{11}$ and $R^{12}$ are joined and, taken together with the nitrogen atom and SO$_2$ group to which they are attached, form a heterocyclic moiety of the formula

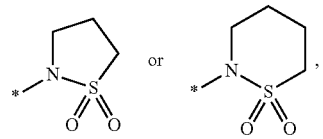 [SMILES: *N1CCCS1(=O)=O ; *N1CCCCS1(=O)=O]

wherein * denotes the point of attachment to the indazole moiety, $R^{15}$ is hydrogen or $(C_1-C_4)$-alkyl optionally substituted with hydroxy, methoxy, ethoxy, amino, methylamino, ethylamino, dimethylamino or diethylamino, $R^{16}$ is selected from the group consisting of hydrogen, $(C_1-C_4)$-alkyl, $(C_3-C_6)$-cycloalkyl and 5- or 6-membered heterocycloalkyl, wherein
(i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
and
(ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl,
wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^{15}$ and $R^{16}$ are joined and, taken together with the nitrogen atom to which they are attached, form a 5- or 6-membered heterocycloalkyl ring, which may contain a second ring heteroatom selected from N and O, and which is optionally substituted with one or two substituents independently selected from the group consisting of methyl, ethyl, oxo, hydroxy, methoxy, ethoxy, amino, methylamino, ethylamino, dimethylamino and diethylamino, $R^2$ is hydrogen or fluoro, $R^3$ is cyano, $R^4$ is methyl, trifluoromethyl or amino, $R^5$ is $(C_1-C_4)$-alkyl optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino and 5- or 6-membered heterocycloalkyl, wherein (i) said $(C_1-C_4)$-alkoxy substituent is optionally further substituted with a residue selected from the group consisting of methoxy, ethoxy, amino, methylamino, ethylamino, dimethylamino and diethylamino, and (ii) said mono-$(C_1-C_4)$-alkylamino and di-$(C_1-C_4)$-alkylamino substituents are optionally further substituted with one or two residues selected from the group consisting of hydroxy, methoxy and ethoxy, or $R^5$ is $(C_3-C_6)$-cycloalkyl or 5- or 6-membered heteroaryl each of which is optionally substituted with one or two substituents independently selected from the group consisting of fluoro, methyl, ethyl, methylamino, ethylamino, dimethylamino and diethylamino, and $R^6$ is hydrogen or methyl.

4. The compound of formula (I) according to claim 1, wherein $R^1$ is a group of the formula —$NR^7R^8$, —$NR^{11}$—$SO_2$—$R^{12}$, —$OR^{13}$ or —$S(=O)_n$—$R^{14}$, wherein n is 0 or 2, $R^7$ is $(C_1-C_4)$-alkyl optionally substituted with hydroxy, methoxy, ethoxy, amino, methylamino, ethylamino, dimethylamino or diethylamino, $R^8$, $R^{12}$, $R^{13}$ and $R^{14}$ are each selected from the group consisting of $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of fluoro, trifluoromethyl, hydroxy, methoxy, ethoxy, isopropoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, and $R^{11}$ is hydrogen or methyl, $R^2$ is hydrogen or fluoro, $R^3$ is cyano, $R^4$ is methyl, difluoromethyl or trifluoromethyl, $R^5$ is methyl, difluoromethyl or trifluoromethyl, and $R^6$ is hydrogen.

5. A process for preparing a compound of formula (I) as defined in claim 1, wherein $R^6$ is hydrogen, characterized in that

[A] an aldehyde of formula (II)

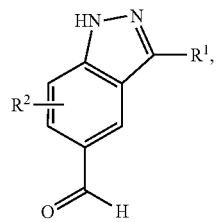

(II)

wherein $R^1$ and $R^2$ have the meanings indicated in claim 1, is reacted in the presence of an acid, an acid/base combination and/or a dehydrating agent with a cyanoenolate of formula (III)

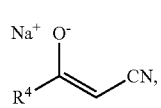

(III)

wherein $R^4$ has the meaning indicated in claim 1, to give a compound of formula (IV)

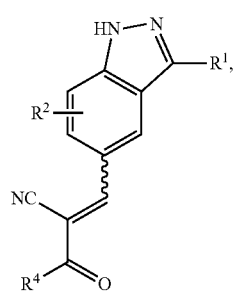

(IV)

wherein $R^1$, $R^2$ and $R^4$ have the meanings described above, and the latter is then condensed with a compound of formula (V)

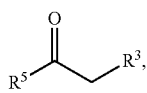

(V)

wherein $R^3$ and $R^5$ have the meanings indicated in claim 1,
in the presence of an ammonia source to give a compound of formula (I-A)

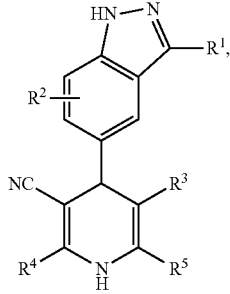

(I-A)

wherein $R^1$, $R^2$, $R^3$, $R^4$ and $R^5$ have the meanings described above, or

[B] an aldehyde of formula (VI)

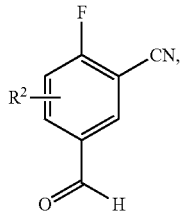

(VI)

wherein $R^2$ has the meaning indicated in claim 1,
is reacted in the presence of an acid, an acid/base combination and/or a dehydrating agent with a cyanoenolate of formula (III)

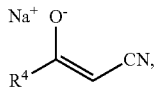

(III)

wherein $R^4$ has the meaning indicated in claim 1,
to give a compound of formula (VII)

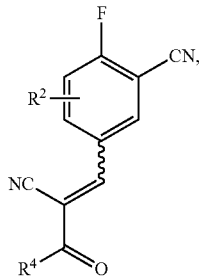

(VII)

wherein $R^2$ and $R^4$ have the meanings described above, the latter is then condensed with a compound of formula (V)

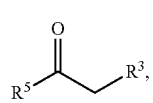

(V)

wherein $R^3$ and $R^5$ have the meanings indicated in claim 1,
in the presence of an ammonia source to give a compound of formula (VIII)

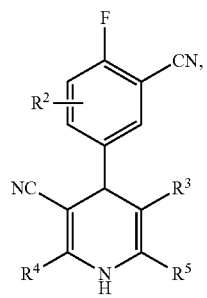

(VIII)

wherein $R^2$, $R^3$, $R^4$ and $R^5$ have the meanings described above, subsequently the compound of formula (VIII) is treated with hydrazine to yield a 3-aminoindazole of formula (IX)

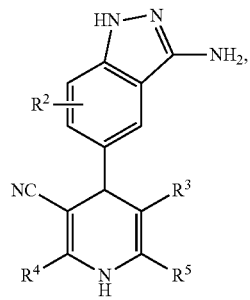

(IX)

wherein $R^2$, $R^3$, $R^4$ and $R^5$ have the meanings described above, which is converted into the $N^1$-protected derivative of formula (X)

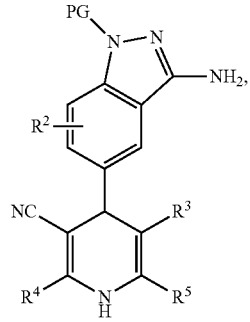

(X)

wherein $R^2$, $R^3$, $R^4$ and $R^5$ have the meanings described above, and

PG represents a suitable indazole-protecting group,
and treated with a sulfonyl chloride of formula (XI)

(XI)

wherein $R^{12}$ has the meaning indicated in claim 1,
in the presence of a base to give a compound of formula (XII-A)

(XII-A)

wherein PG, $R^2$, $R^3$, $R^4$, $R^5$ and $R^{12}$ have the meanings described above,
which is optionally followed by N-alkylation with a compound of formula (XIII)

$R^{11A}$—Z  (XIII), wherein
$R^{11A}$ represents $(C_1-C_6)$-alkyl
and
Z represents a leaving group
in the presence of a base to afford a compound of formula (XII-B)

(XII-B)

wherein PG, $R^2$, $R^3$, $R^4$, $R^5$, $R^{11A}$ and $R^{12}$ have the meanings described above,
and the resulting compound of formula (XII-A) or (XII-B) is deprotected to give a compound of formula (I-B)

(I-B)

wherein $R^2$, $R^3$, $R^4$, $R^5$, $R^{11}$ and $R^{12}$ have the meanings described above,
optionally followed by (i) separating the compound (I-A) or (I-B) into its respective enantiomers and/or diastereomers, and/or (ii) converting the compound (I-A) or (I-B) into a hydrate, solvate, salt and/or hydrate or solvate of a salt by treatment with the corresponding solvents and/or acids or bases.

6. The process of claim 5, wherein PG is tert-butoxycarbonyl, 2-(trimethylsilyl)ethoxymethyl or p-methoxybenzyl.

7. The process of claim 5, wherein Z is halogen, mesylate, triflate or tosylate.

8. A pharmaceutical composition comprising a compound as defined in claim 1, and a pharmaceutically acceptable excipient.

9. The pharmaceutical composition of claim 8 further comprising one or more additional therapeutic agents.

10. The pharmaceutical composition of claim 9, wherein the additional therapeutic agent is an anti-tumor agent.

11. A method of treating or preventing a cell proliferative disorder, comprising administering to a mammal in need thereof a therapeutically effective amount of one or more compounds as defined in claim 1.

12. The method of claim 11, wherein the cell proliferative disorder is a cancer.

13. The method of claim 12, wherein the cancer is a cancer of the breast, respiratory tract, brain, reproductive organs, digestive tract, urinary tract, eye, liver, skin, head or neck, thyroid, parathyroid, or a distant metastasis of a solid tumor.

14. The method of claim 12, wherein the compound as defined in claim 1 is administered in conjunction with surgery or radiation therapy.

15. A method of treating or preventing a cell proliferative disorder, comprising administering to a mammal in need thereof a therapeutically effective amount of a pharmaceutical composition as defined in claim 9.

16. The method of claim 15, wherein the cell proliferative disorder is a cancer of the breast, respiratory tract, brain, reproductive organs, digestive tract, urinary tract, eye, liver, skin, head or neck, thyroid, parathyroid, or a distant metastasis of a solid tumor.

17. The method of claim 15, wherein the pharmaceutical composition as defined in claim 10 is administered in conjunction with surgery or radiation therapy.

18. A method of treating or preventing a cell proliferative disorder, comprising administering to a mammal in need thereof a therapeutically effective amount of a pharmaceutical composition as defined in claim 10.

19. The method of claim 18, wherein the cell proliferative disorder is a cancer of the breast, respiratory tract, brain, reproductive organs, digestive tract, urinary tract, eye, liver, skin, head or neck, thyroid, parathyroid, or a distant metastasis of a solid tumor.

20. The method of claim 18, wherein the pharmaceutical composition as defined in claim 10 is administered in conjunction with surgery or radiation therapy.

* * * * *